(12) United States Patent
Ericsson

(10) Patent No.: US 12,227,797 B2
(45) Date of Patent: Feb. 18, 2025

(54) SPATIAL ANALYSIS OF A PLANAR BIOLOGICAL SAMPLE

(71) Applicant: MOLECULENT AB, Saltsjöbaden (SE)

(72) Inventor: Olof John Ericsson, Saltsjöbaden (SE)

(73) Assignee: MOLECULENT AB, Solna (SE)

( * ) Notice: Subject to any disclaimer, the term of this patent is extended or adjusted under 35 U.S.C. 154(b) by 0 days.

(21) Appl. No.: 18/569,594

(22) PCT Filed: Jun. 23, 2022

(86) PCT No.: PCT/IB2022/055849
§ 371 (c)(1),
(2) Date: Dec. 12, 2023

(87) PCT Pub. No.: WO2022/269543
PCT Pub. Date: Dec. 29, 2022

(65) Prior Publication Data
US 2024/0287587 A1 Aug. 29, 2024

Related U.S. Application Data

(60) Provisional application No. 63/257,456, filed on Oct. 19, 2021, provisional application No. 63/214,701, filed on Jun. 24, 2021.

(51) Int. Cl.
*C12Q 1/68* (2018.01)
*C12Q 1/6806* (2018.01)
*C12Q 1/6841* (2018.01)

(52) U.S. Cl.
CPC ......... *C12Q 1/6841* (2013.01); *C12Q 1/6806* (2013.01)

(58) Field of Classification Search
CPC .................................................. C12Q 1/6841
See application file for complete search history.

(56) References Cited

U.S. PATENT DOCUMENTS 6,465,175 B2  10/2002  Horn et al.
2004/0081979 A1  4/2004  Knezevic et al.
(Continued)

FOREIGN PATENT DOCUMENTS

WO  WO 2010/081114 A2  7/2010
WO  WO 2011/150316 A1  12/2011
(Continued)

OTHER PUBLICATIONS

Asp et al., "Spatially Resolved Transcriptomes—Next Generation Tools for Tissue Exploration", BioEssays, 2020, 42: 1900221, 16 pages.
(Continued)

*Primary Examiner* — Kenneth R Horlick
(74) *Attorney, Agent, or Firm* — James S. Keddie; Bozicevic, Field & Francis LLP

(57) ABSTRACT

Provided herein, among other things, is method for analyzing a planar biological sample. In some embodiments, the method may comprise: contacting an oligonucleotide or a conjugate comprising the same with a planar biological sample under conditions by which the oligonucleotide or conjugate specifically binds to sites in or on the sample; performing one or more steps to release and/or extend the oligonucleotide in situ, to produce a reporter probe; transferring the reporter probe from the sample to a planar support that does not comprise an array of oligonucleotides, in a way that preserves the spatial relationship of the reporter probe in the sample; and detecting the reporter probe on the support.

22 Claims, 17 Drawing Sheets

Specification includes a Sequence Listing.

(56) References Cited

U.S. PATENT DOCUMENTS

| | | | |
|---|---|---|---|
| 2014/0066318 A1* | 3/2014 | Frisen | C12Q 1/6853 506/3 |
| 2014/0274775 A1 | 9/2014 | Glezer et al. | |
| 2018/0057873 A1 | 3/2018 | Zhou et al. | |
| 2018/0245142 A1* | 8/2018 | So | C12Q 1/6816 |
| 2020/0277663 A1 | 9/2020 | Ramachandran Iyer et al. | |
| 2021/0230681 A1 | 7/2021 | Patterson et al. | |

FOREIGN PATENT DOCUMENTS

| | | |
|---|---|---|
| WO | WO 2012/057689 A1 | 5/2012 |
| WO | WO 2018/160397 A1 | 9/2018 |
| WO | WO 2020/160044 A1 | 8/2020 |
| WO | WO 2020/180645 A1 | 9/2020 |
| WO | WO 2020/198071 A1 | 10/2020 |
| WO | WO 2021/092433 A2 | 5/2021 |
| WO | WO 2021/168287 A1 | 8/2021 |
| WO | WO 2022/087273 A1 | 4/2022 |

OTHER PUBLICATIONS

Borm et al., "Scalable in situ single-cell profiling by electrophoretic capture of mRNA", bioRxiv, preprint doi: https://doi.org/10.1101/2022.01.12.476082, 2022, 32 pages.

Goransson et al., "A single molecule array for digital targeted molecular analyses", Nucleic Acids Research, 2008, 37(1): e7, 9 pages.

Hosokawa et al., "Size-Selective Microcavity Array for Rapid and Efficient Detection of Circulating Tumor Cells", Analytical Chemistry, 2010, 82(15): 6629-6635.

Jordi, "Development of Proximity Ligation Assay variants for single cell proteomics", thesis submitted to attain the degree of Doctor of Sciences of EZH Zurich, 2020, ETH Library, Diss. ETH Nr. 26148, 147 pages.

Matsunaga et al., "High-Efficiency Single-Cell Entrapment and Fluorescence in Situ Hybridization Analysis Using a Poly(dimethylsiloxane) Microfluidic Device Integrated with a Black Poly(ethylene terephthalate) Micromesh", Analytical Chemistry, 2008, 80(13): 5139-5145.

Merritt et al., "High multiplex, digital spatial profiling of proteins and RNA in fixed tissue using genomic detection methods", bioRxiv preprint doi: https://doi.org/10.1101/559021, 2019, 50 pages.

Nagendran et al., "Automated cell-type classification in intact tissues by single-cell molecular profiling", eLife, Jul. 2018: e30510, 19 pages.

Oguchi et al., "Development of a sequencing system for spatial decoding of DNA barcode molecules at single-molecule resolution", Communications Biology, Mar. 2020: 788, https://doi.org/10.1038/s42003-020-01499-8, 13 pages.

Ouyang et al., "MicroRNA Detection Specificity: Recent Advances and Future Perspective", Analytical Chemistry, 2019, 91: 3179-3186.

Piwosz et al., "CARD-FISH in the Sequencing Era: Opening a New Universe of Protistan Ecology", Frontiers in Microbiology, Mar. 2021, vol. 12, Article 640066, 24 pages.

Rodriques et al., "Slide-seq: A Scalable Technology for Measuring Genome-Wide Expression at High Spatial Resolution", Science, 2019, 363(6434): 1463-1467.

Soderberg et al., "Characterizing proteins and their interactions in cells and tissues using the in situ proximity ligation assay", Methods, 2008, 45: 227-232.

Tang et al., "Microfluidic device with integrated microfilter of conical-shaped holes for high efficiency and high purity capture of circulating tumor cells", Scientific Reports, Apr. 2014: 6052, 7 pages.

Wang et al., "A Novel in Situ RNA Analysis Platform for Formalin-Fixed, Paraffin-Embedded Tissues", The Journal of Molecular Diagnostics, 2012, 14(1): 22-29.

Zhang et al., "Direct Visualization of Single-Nucleotide Variation in mtDNA Using a CRISPR/Cas9-Mediated Proximity Ligation Assay", Journal of the American Chemical Society, 2018, 140: 11293-11301.

Zinggeler et al., "Biophysical Insights on the Enrichment of Cancer Cells from Whole Blood by (Affinity) Filtration", Scientific Reports, Sep. 2019: 1246, 11 pages.

Credle et al., "Multiplexed analysis of fixed tissue RNA using Ligation in situ Hybridization", Nucleic Acids Research, 2017, 45(14): e128, 9 pages.

* cited by examiner

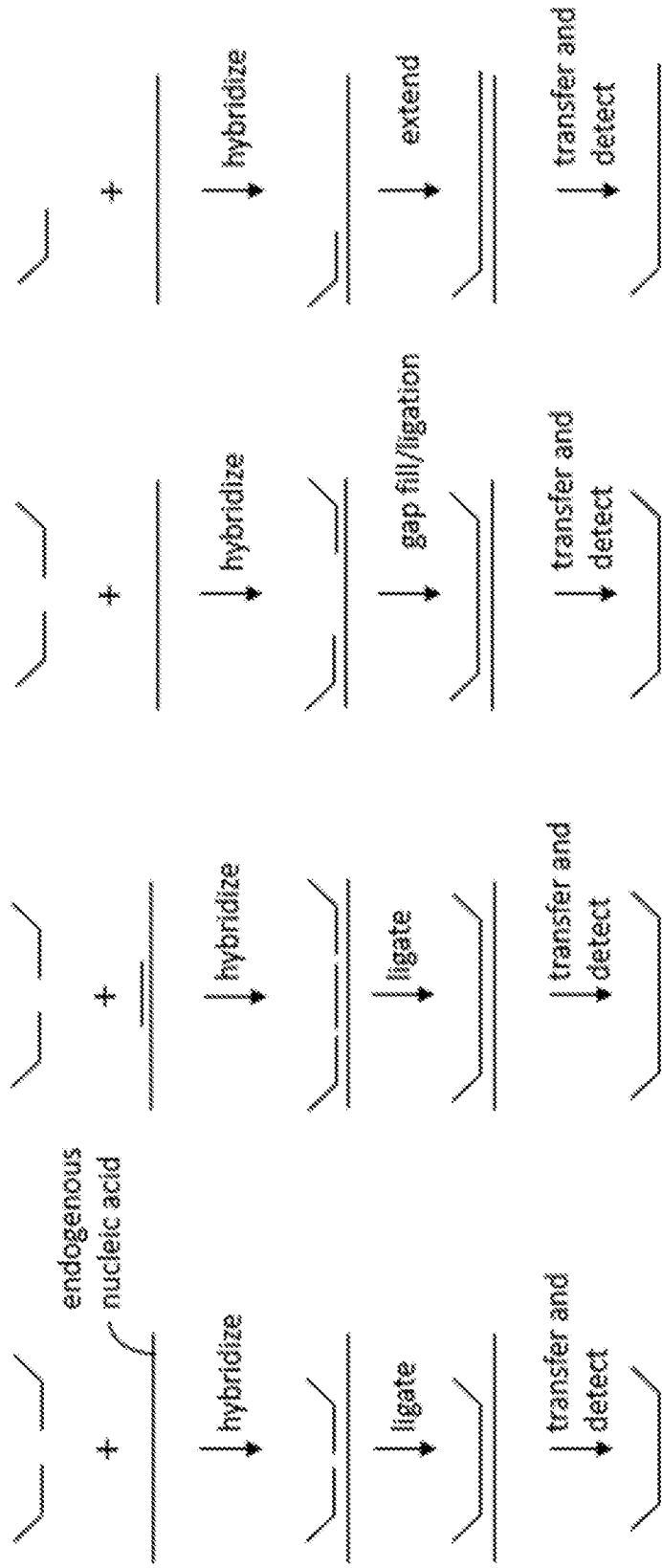

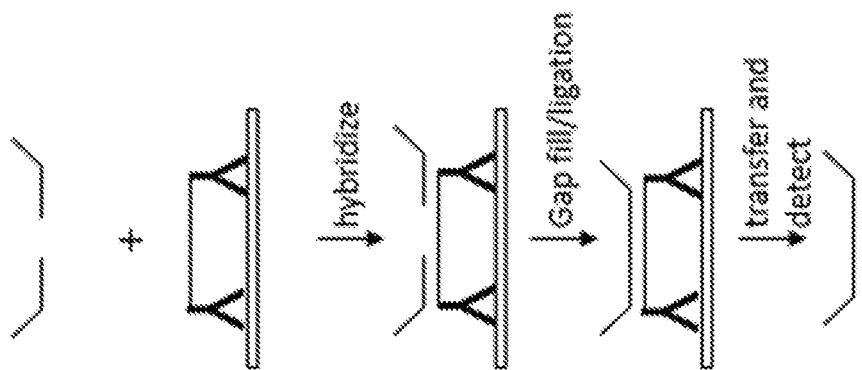
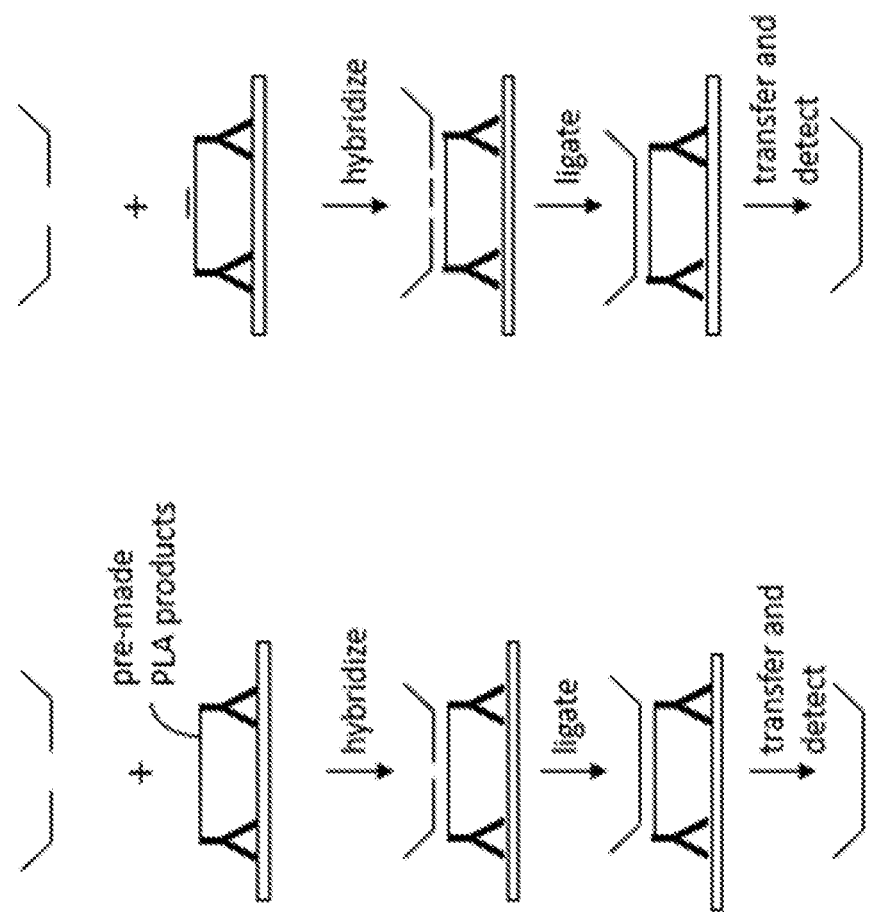

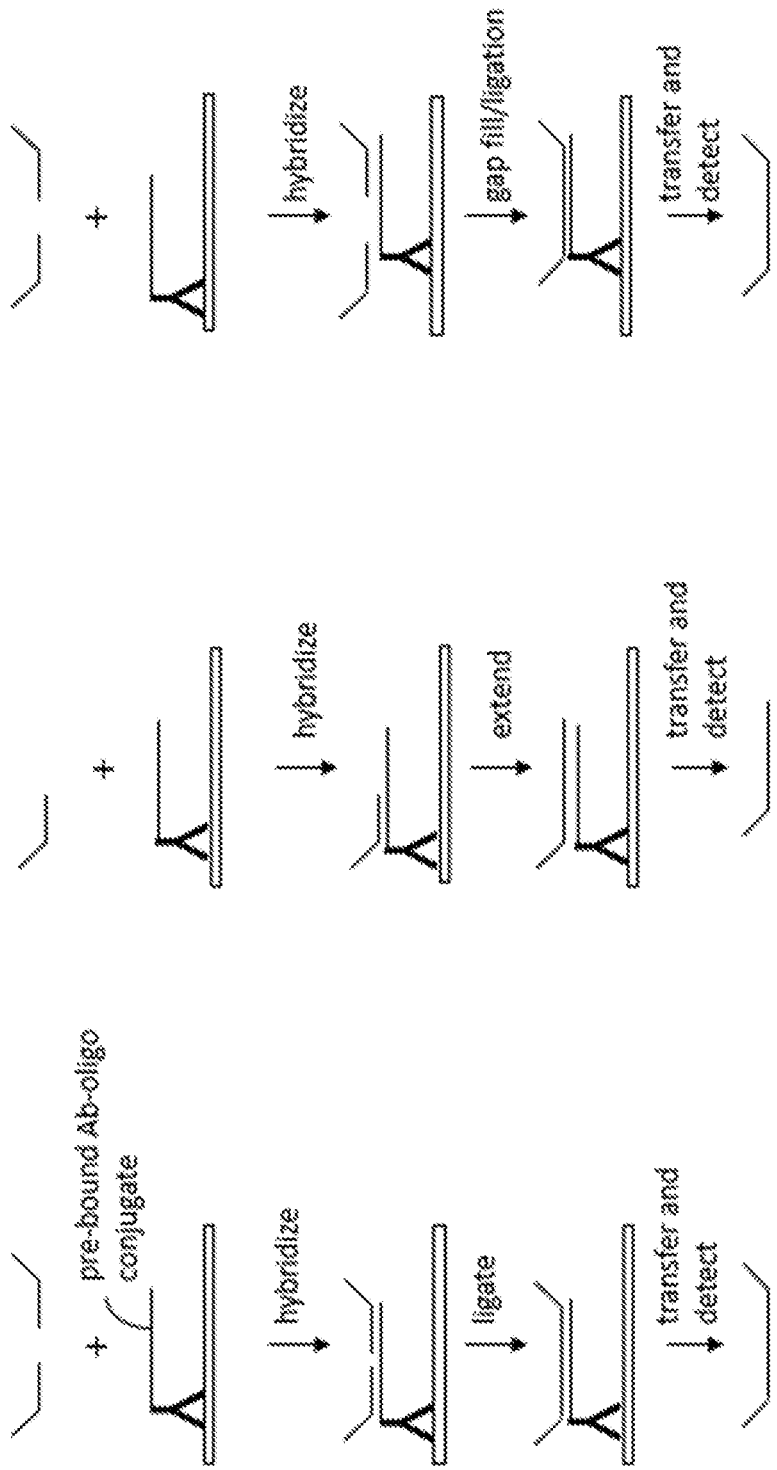

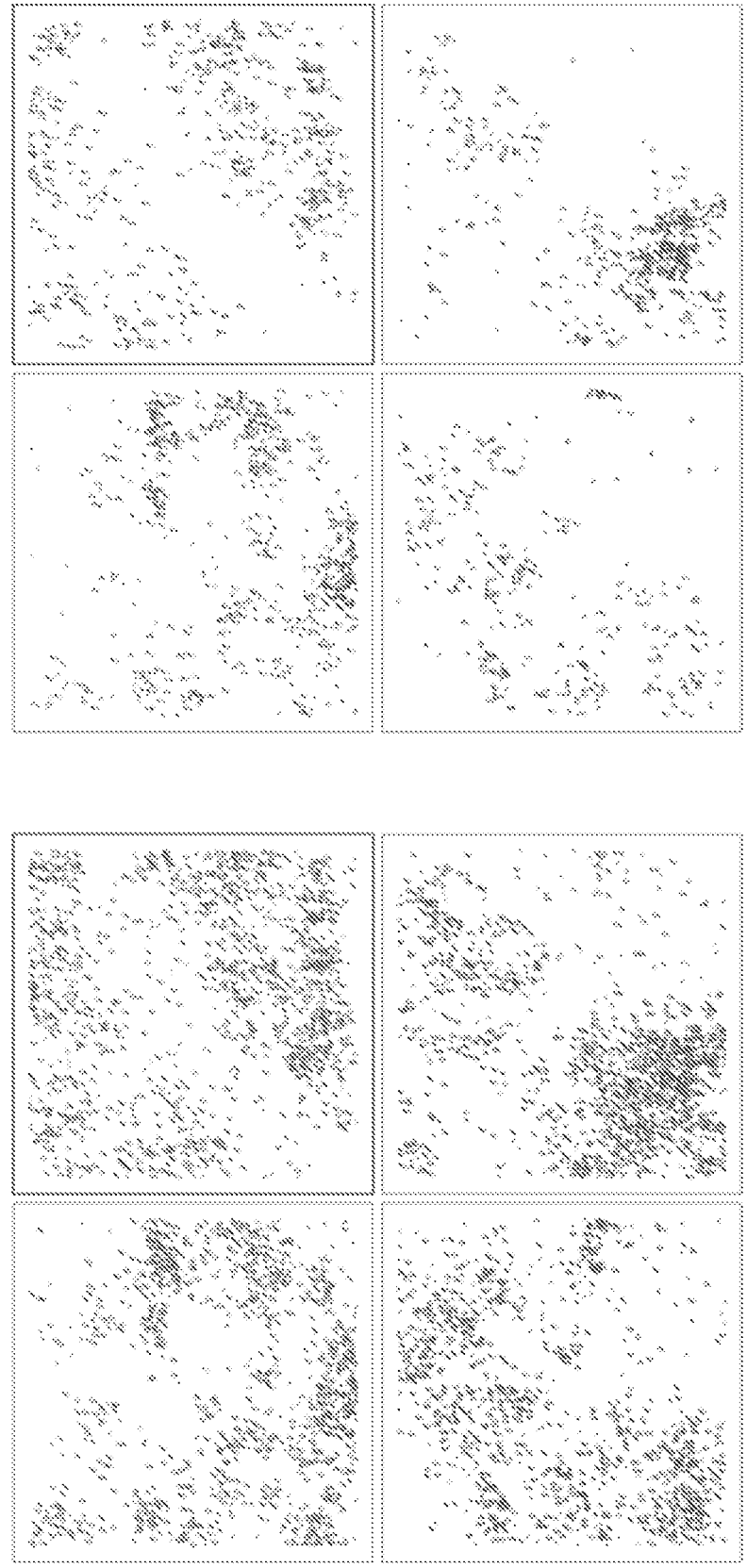

reference reporter molecule locations spots c0o-detected with system1 and 2

```
                        SEQUENCE LISTING

<160> NUMBER OF SEQ ID NOS: 5

<210> SEQ ID NO 1
<211> LENGTH: 36
<212> TYPE: DNA
<213> ORGANISM: artificial sequence
<220> FEATURE:
<223> OTHER INFORMATION: synthetic oligonucleotide

<400> SEQUENCE: 1
tttuuucgtu tacgaccucu aaggccacga uagcgt                            36

<210> SEQ ID NO 2
<211> LENGTH: 36
<212> TYPE: DNA
<213> ORGANISM: artificial sequence
<220> FEATURE:
<223> OTHER INFORMATION: synthetic oligonucleotide

<400> SEQUENCE: 2
atgcuaaccg cagaccacta ggcgaatacg tttttt                            36

<210> SEQ ID NO 3
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 3
cggttagcat acgctatcgt                                              20

<210> SEQ ID NO 4
<211> LENGTH: 60
<212> TYPE: DNA
<213> ORGANISM: artificial sequence
<220> FEATURE:
<223> OTHER INFORMATION: synthetic oligonucleotide

<400> SEQUENCE: 4
ggccttagag gtcgtaaacg tttgaagcaa tccgtgggcg ggcgcaaacg tttgtcgaca   60

<210> SEQ ID NO 5
<211> LENGTH: 60
<212> TYPE: DNA
<213> ORGANISM: artificial sequence
<220> FEATURE:
<223> OTHER INFORMATION: synthetic oligonucleotide
```

```
<400> SEQUENCE: 5
aatgtttcgc gtgcatccgg ctccaccgga tttgcagctt cgtattcgcc tagtggtctg        60
```

SPATIAL ANALYSIS OF A PLANAR BIOLOGICAL SAMPLE

CROSS-REFERENCING

This application is a § 371 national phase of International Application No. PCT/IB2022/055849, filed on Jun. 23, 2022, which claims the benefit of U.S. provisional application Ser. No. 63/214,701, filed on Jun. 24, 2021, and 63/257,456, filed on Oct. 19, 2021, which applications are incorporated by reference in their entireties.

BACKGROUND

Protein expression, RNA expression, and interactions among biomolecules in a tissue can be examined using a variety of methods. For example, one can perform a proximity assay on a tissue section and detect the products in situ (Hegazy et al. (2020), *Current Protocols in Cell Biology*, 89(1):e115). In such methods, proximally located target proteins or epitopes are bound by the corresponding antibodies that bring together oligonucleotides conjugated to the antibodies. The oligonucleotides are ligated and amplified using for example rolling circle amplification (RCA). The amplification product can then be detected in the tissue section or sequenced following incorporation of a spatial barcode. Depending upon the sequencing or detection, the proximally located proteins are deciphered. Other techniques of spatial analysis include using labelled antibodies to perform subsequent immune histochemistry or labeling RNA with various combinations and designs of fluorescent oligonucleotides.

However, these conventional methods are limited for several reasons. The detection of molecules present in a tissue suffers from optical crowding because the number of molecules that can be resolved in one image are limited. With many molecules crowded in an analyzed area, the detection methods lose resolution thereby making it difficult to produce images with high resolution.

Further, the amplification-based methods suffer from spatial crowding, i.e., these methods are limited by the number of molecules that can be placed physically in one area. For example, RCA amplification produces large DNA amplification products that crowd in an area, making it difficult to distinguish them individually.

Moreover, many of the conventional methods are time consuming and laborious because it takes time for the reactants to diffuse into and out of the tissue section and image the depth of the tissue section using a so-called z-stack. For example, multiplexed assays, e.g., multiplexed assays such as single molecule fluorescence in situ hybridization (smFISH) assays can take several days (see e.g., Shah et al., Neuron 2016 92: 342-357). Further, because biological specimens often produce a significant amount of background signal, the images obtained from conventional methods are often not very clean which makes the detection of labeled molecules more challenging.

Therefore, methods for spatial analysis are desired that solve these problems associated with the conventional methods.

SUMMARY

Provided herein, among other things, is method for analyzing a planar biological sample. In some embodiments, the method may comprise: contacting an oligonucleotide or a conjugate comprising the same with a planar biological sample under conditions by which the oligonucleotide or conjugate specifically binds to sites in or on the sample; performing one or more steps to release and/or extend the oligonucleotide in situ, to produce a reporter probe; transferring the reporter probe from the sample to a planar support that does not comprise an array of oligonucleotides, in a way that preserves the spatial relationship of the reporter probe in the sample; and detecting the reporter probe on the support. As will be described in greater detail below, the method may be implemented in a variety of different ways.

In some embodiments, the method may comprise performing a proximity assay on one or more pairs of binding agent-oligonucleotide conjugates that are bound to the sample, in situ, to produce proximity assay reaction products, transferring the nucleic acid reaction products into or onto a support in a way that preserves the spatial relationship of the proximity assay reaction products in the sample, and detecting the proximity assay reaction products in or on the support.

As will be described in greater detail below, the proximity assay reaction products transferred to the support can be produced in a variety of different ways, e.g., by performing a ligation, primer extension, gap-fill/ligation or any hybrid thereof between the oligonucleotides of the binding agent-oligonucleotide conjugates such that the sequence of one of the oligonucleotides becomes covalently joined to another oligonucleotide or copy of the same, and then transferring the first product to the support. Alternatively, the first products or unligated oligonucleotides can serve as a splint for ligating other oligonucleotides together to produce second products. In these embodiments, the second products may be transferred to the support.

For example, in one non-limiting embodiment, the method may comprise performing the proximity assay on one or more pairs of binding agent-oligonucleotide conjugates that are bound to the sample, in situ, to produce first products and then transferring the first products or second products that contain the complement of the first products (made via a ligation that is splinted by the first products) to the support. If the first products are transferred to the support, then they may be cleaved from the binding agents before transfer.

The targets that are bound by the binding agent-oligonucleotide conjugates may be proteinaceous, a nucleic acid, or even a small molecule. As such, in some embodiments, a binding agent-oligonucleotide conjugate may be composed of a binding agent (e.g., an antibody) that is conjugated to an oligonucleotide. In other embodiments, the binding agent-oligonucleotide conjugate may be composed of an oligonucleotide, where one part of the oligonucleotide hybridizes to a particular sequence in a cellular RNA or gene and the other part of the oligonucleotide does not hybridize to that RNA or gene. Depending on the binding agent-oligonucleotide conjugates used, the present method can be employed to examine protein expression, post-translational modification, RNA expression and genomic DNA, among other things.

The present method, depending upon how it is implemented, can avoid several problems with the conventional methods.

For example, because the nucleic acid reaction products are analyzed after they have been transferred to a support, a major source of background, i.e., the tissue section, can be avoided.

In some cases, a high-resolution image may be obtained by imaging the sample in one plane. Thus, unlike some conventional methods, some of the embodiments disclosed herein avoid taking z-stacks of images during detection since the molecules can be transferred to a planar 2D surface. Making Z-stacks can are time consuming and reduce analysis throughout. Thus, the method disclosed herein, depending upon how it is implemented, can avoid the need to imaging z-stacks and potentially save time and cost.

Additionally, in some cases, the present method may involve repeated cycles of label detection. Because, transferred DNA molecules can be attached to a support using very stable chemistries involving covalent attachment or for example biotin-avidin which are generally stable even after multiple cycles of labeling and washing, the method may allow molecules to be detected sequentially and combinatorically over a very high number of cycles. Particularly, the DNA molecules attached to the support withstand multiple rounds of labeling and washing. This can be a significant challenge when imaging molecules in tissue materials since the tissue disintegrate slowly over detection and washing cycles. Because only a few barcodes or combinations of barcodes are detected in a cycle, the molecules that are labeled in a particular cycle will be spaced apart more compared to if all analyzed molecules are detected in the same cycle thereby avoiding optical crowding, i.e., emission of multiple signals from one location. The possibility to use more detection cycles when molecules are firmly immobilized therefore also allows the detection of more (and different) target molecules (higher multiplex detection). The method disclosed herein is more straightforward to multiplex because multiple cycles of labeling and detecting can be directed to different target barcodes or combinations of barcodes that can be included in oligonucleotides conjugated to different binding agent-oligonucleotide conjugates.

Also, in some cases, bridging oligonucleotides are used that amplify signals from the barcodes or combinations of barcodes thereby providing higher signal to noise ratio. For example, reading molecules on a support as performed in the method disclosed herein can be advantageous for high spatial resolution compared to reading molecules indirectly as done in certain conventional methods, e.g., by sequencing as performed in certain amplification-based methods. By transferring the nucleic acid reaction products to a support, it is easier to perform single molecule detection with lower background comparted to analysis in the tissues, where background fluorescence can be high.

In amplification based conventional methods, multiple copies of target nucleic acids are produced, for example, via RCA. Presence of multiple copies of the same nucleic acid target can produce physical crowding of the nucleic acids in the examined specimen. Moreover, methods that are based on amplification typically produce a variable number of copies of the target, which, in turn, results in a variable signal from each molecule. However, in the method disclosed herein have embodiments where a defined number of molecules can be used to label each molecular target for detection, and each a single molecule is detected using a predetermined number of labels resulting in a more uniform detection signal. Furthermore, compared to RCA-based approaches where a large bundle of DNA is created for each detected molecule the current method has embodiments where the labels and labeling oligonucleotides used for detection can be completely washed away between each detection cycle reducing the physical crowding between molecules and leaving only the reporter molecule attached to the surface. Therefore, depending upon how the method is implemented, the method disclosed herein can avoid the problem of physical crowding of target nucleic acids in the specimen.

Further, in some embodiments of the present method, reporter probes are produced using the initial nucleic acid reaction products as a template. An advantage of using reporter probes is that shorter oligonucleotides can be conjugated to the binding agents which, in turn, increases the resolution of the method and improves the kinetics and binding of the binding agents to the targets. Conjugating long oligonucleotides to, for example, antibodies can affect their capability to effectively bind epitopes in a tissue more than shorter oligonucleotides.

Even further, the support containing the nucleic acids being extremely stable, they can be readily stored for long periods of time without any loss of the relevant information.

As noted above, the reporter molecule that is transferred to the support is a nucleic acid. Because the reporter molecule is a nucleic acid, different labeled probes can be hybridized to the same molecule, by hybridizing one probe to the reporter molecule, imaging the support, de-hybridizing the probe (or inactivating the labels), and then hybridizing a different probe to a different site in the reporter molecule. These hybridization/reading/inactivation/hybridization steps may be repeated as many times as necessary. Because the labeling system allows for single molecule resolution, an image may appear as punctate spots, where each spot corresponds to a probe hybridization event. This is allows one to perform multiple iterative rounds of probe hybridization and determine which probes hybridize to a particular site in the sample. This, in turn, allows the support to be analyzed in a multiplex manner (using, e.g., the 'coding' system described in Goransson (Nucl. Acids Res 2009 37 e7), thereby allowing one to map the binding sites corresponding to at least 10, at least 50, at least 100, at least 200, at least 500, at least 1000 or at least 10000 genes or proteins.

In some embodiments, the planar sample may be produced by passing a suspension of cells through a filter, wherein the cells are retained on the filter. This embodiment may be utilized to analyze a suspension of cells. In some embodiments, the method may comprise: (a) filtering a suspension of cells through a porous capillary membrane, thereby distributing the cells on the membrane, (b) placing the membrane on a planar support with the cell side of the membrane facing the support, (c) transferring nucleic acids from the cells into or onto the support in a way that preserves the spatial relationship of the nucleic acid in the cells, (d) removing the porous capillary membrane and cells from the support, and (e) spatially analyzing the nucleic acids transferred to support. Further details of this method are set forth below.

BRIEF DESCRIPTION OF THE FIGURES

The skilled artisan will understand that the drawings described below are for illustration purposes only. The drawings are not intended to limit the scope of the present teachings in any way.

FIGS. 2A-2M illustrate several ways in which the method can be implemented.

FIG. 7 Transfer of fluorescent, biotinylated DNA oligos from tissue (A) to an avidin-coated glass cover slip (B). A) Fluorescence image of a post-transfer tissue where some of the oligos are still present. B) Transferred cover slip corresponding to (A) where some the oligos moved to.

FIGS. 13A-13D show detected reporter molecules. Each Figure represents a 4-FoVs area that is a subset of the larger sampled area shown in FIG. 11. 13A) Spot locations identified using the detection system 1 (L-Probe-7-DetA). 13B) Spot locations identified using the detection system 2 (L-Probe-8-DetB). 13C) Spots/reporter molecules co-detected using detection system 1 and 2. 13D) Spot locations identified using the fluorophore conjugated directly to the reported molecule.

DEFINITIONS

Figure 1:
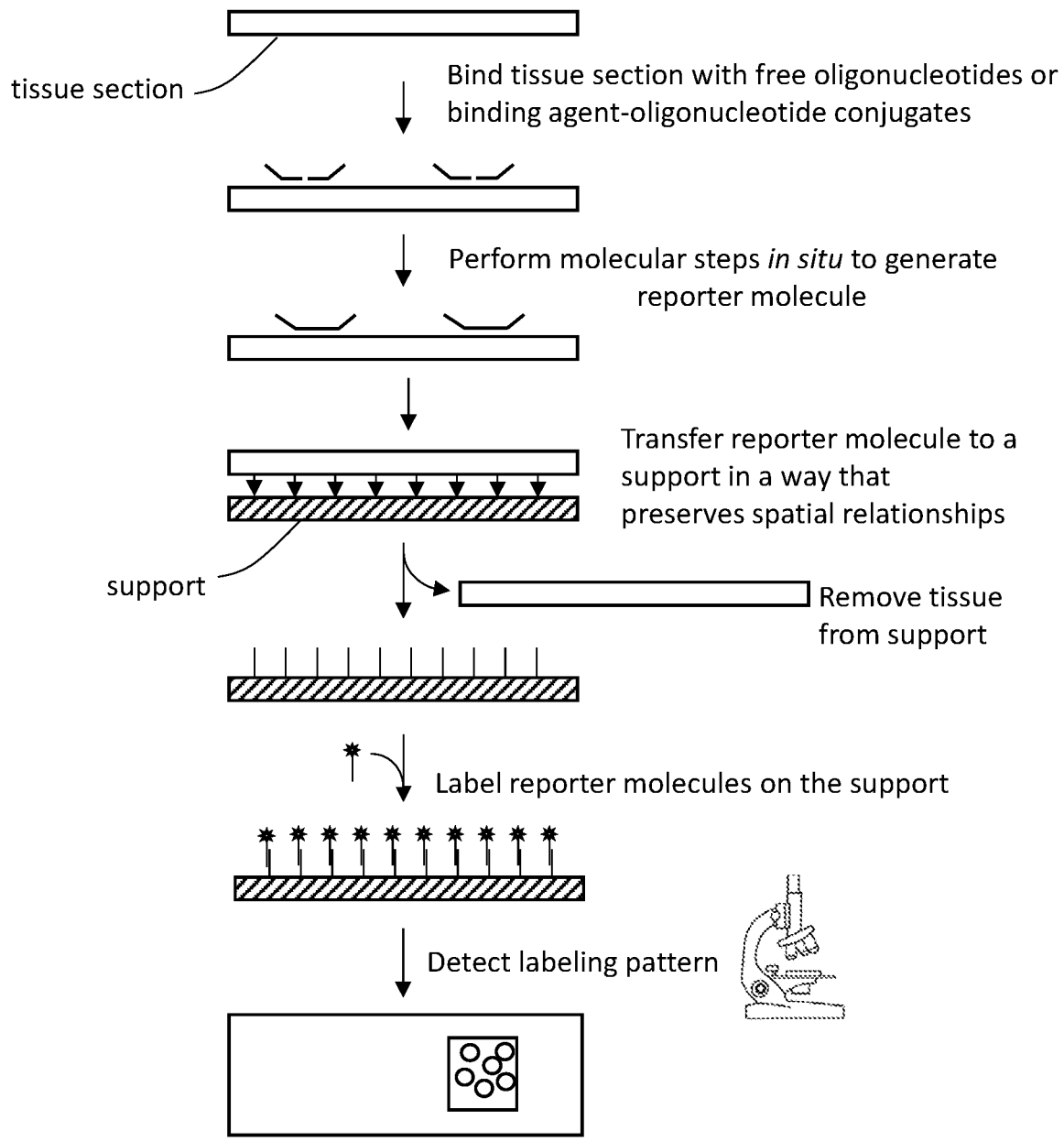
FIG. 1 schematically illustrates some of the principles of the method.
Figures 2K, 2L, 2M:
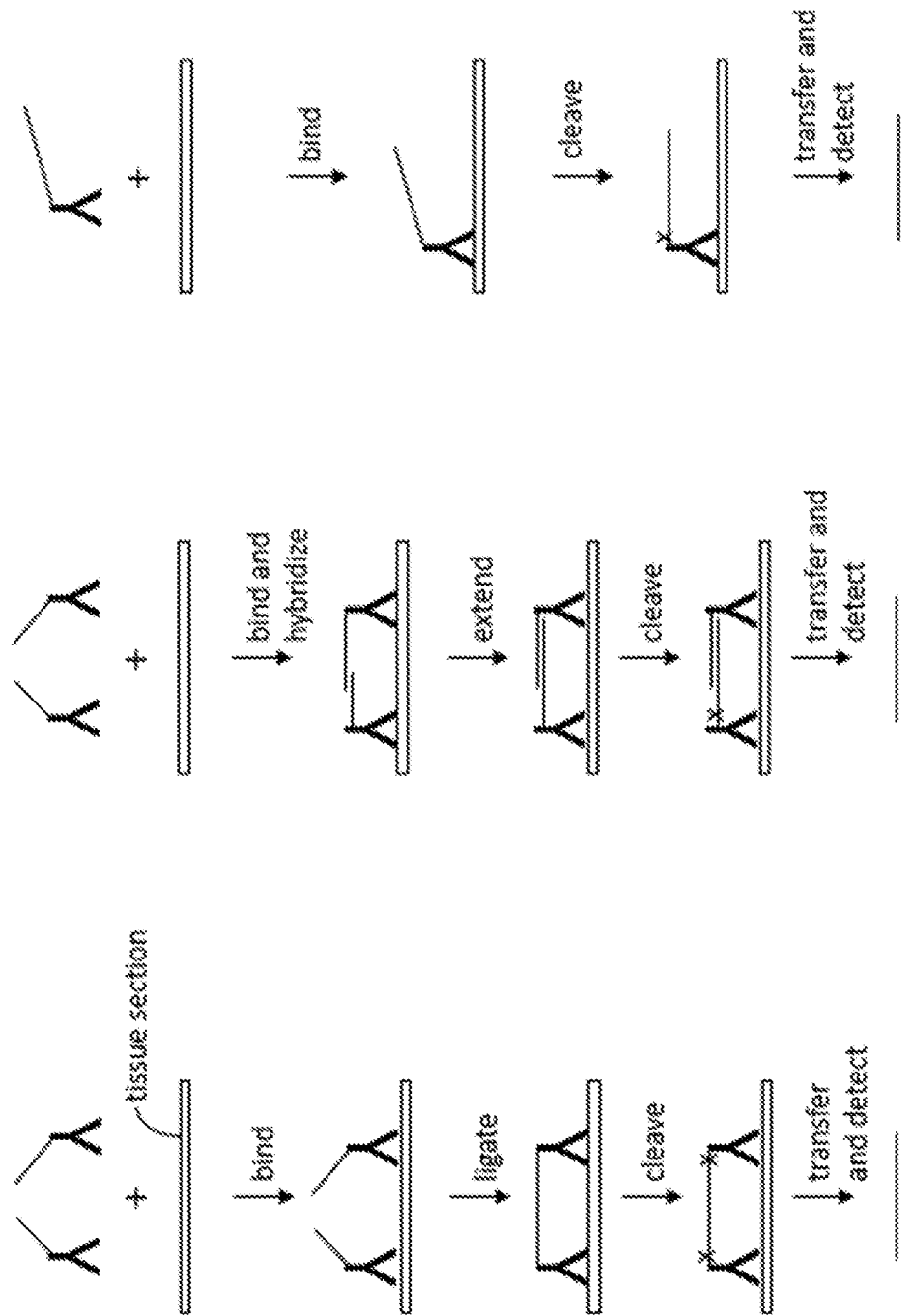

Unless defined otherwise herein, all technical and scientific terms used in this specification have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of ordinary skill in the art with the general meaning of many of the terms used herein. Still, certain terms are defined below for the sake of clarity and ease of reference.

As used herein, the term "multiplexing" refers to the simultaneous detection and/or measurement of multiple biological features of interest, e.g., protein epitopes, in a sample.

As used herein, the terms "antibody" and "immunoglobulin" are used interchangeably herein and are well understood by those in the field. Those terms refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The terms "antibodies" and "immunoglobulin" include antibodies or immunoglobulins of any isotype and fragments of antibodies which retain specific binding to antigen, including, but not limited to, Fab, Fv, scFv, and Fd fragments, chimeric antibodies, humanized antibodies, minibodies, single-chain antibodies, and fusion proteins comprising an antigen-binding portion of an antibody and a non-antibody protein. Also encompassed by the term are Fab', Fv, F(ab')$_2$, and/or other antibody fragments that retain specific binding to antigen, and monoclonal antibodies. Antibodies may exist in a variety of other forms including, for example, Fv, Fab, and (Fab')$_2$, as well as bi-functional (i.e., bi-specific) hybrid antibodies (e.g., Lanzavecchia et al., Eur. J. Immunol. 17, 105 (1987)) and in single chains (e. g., Huston et al., Proc. Natl. Acad. Sci. U.S.A., 85, 5879-5883 (1988) and Bird et al., Science, 242, 423-426 (1988)), which are incorporated herein by reference. (See, generally, Hood et al., "Immunology", Benjamin, N.Y., 2nd ed. (1984), and Hunkapiller and Hood, Nature, 323, 15-16 (1986)).

The term "specific binding" refers to the ability of a binding member to preferentially bind to another binding member that is present in a homogeneous mixture of different molecules.

In certain embodiments, the affinity between a binding member when they are specifically bound in a complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-10}$ M, or less than about $10^{-12}$ M or less.

A "plurality" contains at least 2 members. In certain cases, a plurality may have at least 2, at least 5, at least 10, at least 100, at least 1000, at least 10,000, at least 100,000, at least $10^6$, at least $10^7$, at least $10^8$ or at least $10^9$ or more members. In certain cases, a plurality may have 2 to 100 or 5 to 100 members.

As used herein, the term "labeling" refers to a step that results in binding of a binding agent to specific sites in a sample (e.g., sites containing an epitope for the binding agent (e.g., an antibody) being used, for example) such that the presence and/or abundance of the sites can be determined by evaluating the presence and/or abundance of the binding agent. The term "labeling" refers to a method for producing a labeled sample in which any necessary steps are performed in any convenient order, as long as the required labeled sample is produced. For example, in some embodiments and as will be exemplified below, a sample can be labeled using labeled probes that can be detected to determine distribution of nucleic acids on a support.

As used herein, the term "planar biological sample" refers to a substantially flat, i.e., two-dimensional, material (e.g., glass, metal, ceramics, organic polymer surface or gel) that comprises cells or any combination of biomolecules derived from cells, such as proteins, nucleic acids, lipids, oligo/ polysaccharides, biomolecule complexes, cellular organelles, cellular debris or excretions (exosomes, microvesicles). A planar biological sample can be made by, e.g., growing cells on a planar support, depositing cells on a planar support, e.g., by centrifugation, by cutting a three dimensional object that contains cells into sections and mounting the sections onto a planar support, i.e., producing a tissue section, adsorbing the cellular components onto a surface that is functionalized with affinity agents (e.g. antibodies, haptens, nucleic acid probes), introducing the biomolecules into a polymer gel or transferring them onto a polymer surface electrophoretically or by other means. The cells or biomolecules may be fixed using any number of reagents including formalin, methanol, paraformaldehyde, methanol:acetic acid, glutaraldehyde, bifunctional cross-linkers such as bis(succinimidyl)suberate, bis(succinimidyl) polyethyleneglycol, etc. This definition is intended to cover cellular samples (e.g., tissue sections, etc.), electrophoresis gels and blots thereof, Western blots, dot-blots, ELISAs, antibody microarrays, nucleic acid microarrays, etc. Depending on the specific technique used to prepare the section, a planar biological sample can have a thickness of anywhere from 20 to 50 nm and up to 5 to 10 m.

As used herein, the term "tissue section" refers to a piece of tissue that has been obtained from a subject, optionally fixed, sectioned, and mounted on a planar support, e.g., a microscope slide.

As used herein, the term "formalin-fixed paraffin embedded (FFPE) tissue section" refers to a piece of tissue, e.g., a biopsy sample that has been obtained from a subject, fixed in formaldehyde (e.g., 3%-5% formaldehyde in phosphate buffered saline) or Bouin solution, embedded in wax, cut into thin sections, and then mounted on a microscope slide.

The phrase "in situ" as used here in refers to a specific position or location in a planar biological sample. For example, "a binding agent that is bound to the sample, in situ," indicates that the binding agent is bound at a specific location in the planar biological sample.

A "diagnostic marker" is a specific biochemical in the body which has a particular molecular feature that makes it useful for detecting a disease, measuring the progress of disease or the effects of treatment, or for measuring a process of interest.

A "pathoindicative" cell is a cell which, when present in a tissue, indicates that the animal in which the tissue is located (or from which the tissue was obtained) is afflicted with a disease or disorder. By way of example, the presence of one or more breast cells in a lung tissue of an animal is an indication that the animal is afflicted with metastatic breast cancer.

The term "complementary site" is used to refer to an epitope for an antibody or aptamer, or nucleic acid that has a sequence that is complementary to an oligonucleotide probe. Specifically, if the binding agent is an antibody or aptamer, then the complementary site for the binding agent is the epitope in the sample to which the antibody or aptamer binds. An epitope may be a conformational epitope, or it may be a linear epitope composed of, e.g., a sequence of amino acids. If the binding agent is an oligonucleotide probe, then the complementary site for the binding agent is a complementary nucleic acid (e.g., an RNA or region in a genome).

The term "epitope" as used herein is defined as a structure, e.g., a string of amino acids, on an antigen molecule that is bound by an antibody or aptamer. An antigen can have one or more epitopes. In many cases, an epitope is roughly five amino acids or sugars in size. One skilled in the art understands that generally the overall three-dimensional structure or the specific linear sequence of the molecule can be the main criterion of antigenic specificity.

A "subject" of diagnosis or treatment is a plant or animal, including a human. Non-human animals subject to diagnosis or treatment include, for example, livestock and pets.

As used herein, the term "incubating" refers to maintaining a sample and binding agent under conditions (which conditions include a period of time, one or more temperatures, an appropriate binding buffer and a wash) that are suitable for specific binding of the binding agent to molecules (e.g., epitopes or complementary nucleic acids) in the sample.

As used herein, the term "binding agent" refers to an agent that can specifically binds to complementary sites in a sample. Exemplary binding agents include oligonucleotide probes, antibodies, and aptamers. If antibodies or aptamers are used, in many cases they may bind to protein epitopes.

The terms "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides, ribonucleotides or a combination thereof, and may be produced enzymatically or synthetically (e.g., PNA as described in U.S. Pat. No. 5,948,902 and the references cited therein) and which can hybridize with naturally occurring nucleic acids in a sequence specific manner analogous to that of two naturally occurring nucleic acids, e.g., can participate in Watson-Crick base pairing interactions. Naturally occurring nucleotides include guanine, cytosine, adenine, thymine, uracil (G, C, A, T and U respectively). DNA and RNA have a deoxyribose and ribose sugar backbone, respectively, whereas PNAs backbone is composed of repeating N-(2-aminoethyl)-glycine units linked by peptide bonds. In PNAs, various purine and pyrimidine bases are linked to the backbone by methylene carbonyl bonds. A locked nucleic acid (LNA), often referred to as an inaccessible RNA, is an RNA molecule comprising modified RNA nucleotides. The ribose moiety of an LNA nucleotide is modified with an extra bridge connecting the 2' oxygen and 4' carbon. The bridge "locks" the ribose in the 3'-endo (North) conformation, which is often found in A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability but retain an ability to base pair with naturally occurring C and G residues, respectively. Unstructured nucleic acid is described in US20050233340, which is incorporated by reference herein for disclosure of UNA.

As used herein, the term "oligonucleotide" refers to a multimer of at least 10, e.g., at least 15 or at least 30 nucleotides. In some embodiments, an oligonucleotide may be in the range of 15-200 nucleotides in length, or more. Any oligonucleotide used herein may be composed of G, A, T and C, or bases that are capable of base pairing reliably with a complementary nucleotide. 7-deaza-adenine, 7-deaza-guanine, adenine, guanine, cytosine, thymine, uracil, 2-deaza-2-thio-guanosine, 2-thio-7-deaza-guanosine, 2-thio-adenine, 2-thio-7-deaza-adenine, isoguanine, 7-deaza-guanine, 5,6-dihydrouridine, 5,6-dihydrothymine, xanthine, 7-deaza-xanthine, hypoxanthine, 7-deaza-xanthine, 2,6 diamino-7-deaza purine, 5-methyl-cytosine, 5-propynyl-uridine, 5-propynyl-cytidine, 2-thio-thymine or 2-thio-uridine are examples of such bases, although many others are known. As noted above, an oligonucleotide may be an LNA, a PNA, a UNA, or a morpholino oligomer, for example. The oligonucleotides used herein may contain natural or non-natural nucleotides or linkages.

As used herein, the term "reading" in the context of reading a fluorescent signal, refers to obtaining an image by scanning or by microscopy, where the image shows the pattern of fluorescence as well as the intensity of fluorescence in a field of view.

As used herein, the term "signal generated by," in the context of, e.g., reading a fluorescent signal generated by addition of the fluorescent nucleotide, refers to a signal that is emitted directly from the fluorescent nucleotide or a signal that is emitted indirectly via energy transfer to another fluorescent nucleotide (i.e., by fluorescence resonance energy transfer (FRET)).

As used herein, the term "cleavable linker" refers to a linker containing a bond that can be selectively cleaved by a specific stimulus, e.g., a reducing agent such as TCEP or DTT.

The phrase "specific binding pair" as used herein comprises "a first binding member" and "a second binding member" that have binding specificity for one another. The binding members of a binding pair may be naturally derived or wholly or partially synthetically produced. A binding member has an area on its surface, or a cavity, which specifically binds to and is therefore complementary to a particular spatial and polar organization of the other binding member of a binding pair. Examples of specific binding pairs are antigen-antibody, biotin-avidin, hormone-hormone receptor, receptor-ligand, nucleic acids that hybridize with each other, and enzyme-substrate.

As used herein, the term "binding agent-oligonucleotide conjugate" or "binding agent conjugate" refers to a binding agent, e.g., an antibody, aptamer or oligonucleotide probe, that is non-covalently (e.g., via a streptavidin/biotin interaction) or covalently (e.g., via a "click" reaction (see, e.g., Evans Aus. J. Chem. 2007 60: 384-395) or the like) linked to a single-stranded oligonucleotide in a way that the binding agent can still bind to its binding site. The nucleic acid and the binding agent may be linked via a number of different methods, including those that use a cysteine-reactive maleimide or halogen-containing group. The binding agent and the oligonucleotide may be linked proximal to or at the 5' end of the oligonucleotide, proximal to or at the 3' end of the oligonucleotide, or anywhere in-between. The linkage between a binding agent and the oligonucleotide in a binding agent-oligonucleotide conjugate can be cleavable so that the nucleic acid reaction product can be released from the corresponding binding agents via cleavage of the cleavable linker. As will be illustrated below, a binding agent-oligonucleotide conjugate can be composed of a single oligonucleotide, where one region of the polynucleotide (the "probe" part of the oligonucleotide which may be in the region of 15-50 bases in length hybridizes to a target nucleic acid in the sample (e.g., an RNA) and the other region does not hybridize to that target and is free to participate in the other reactions that are described herein.

An oligonucleotide that is linked to a binding agent in binding agent-oligonucleotide conjugate may be referred to as a "first oligonucleotide" herein.

Figure 6A:
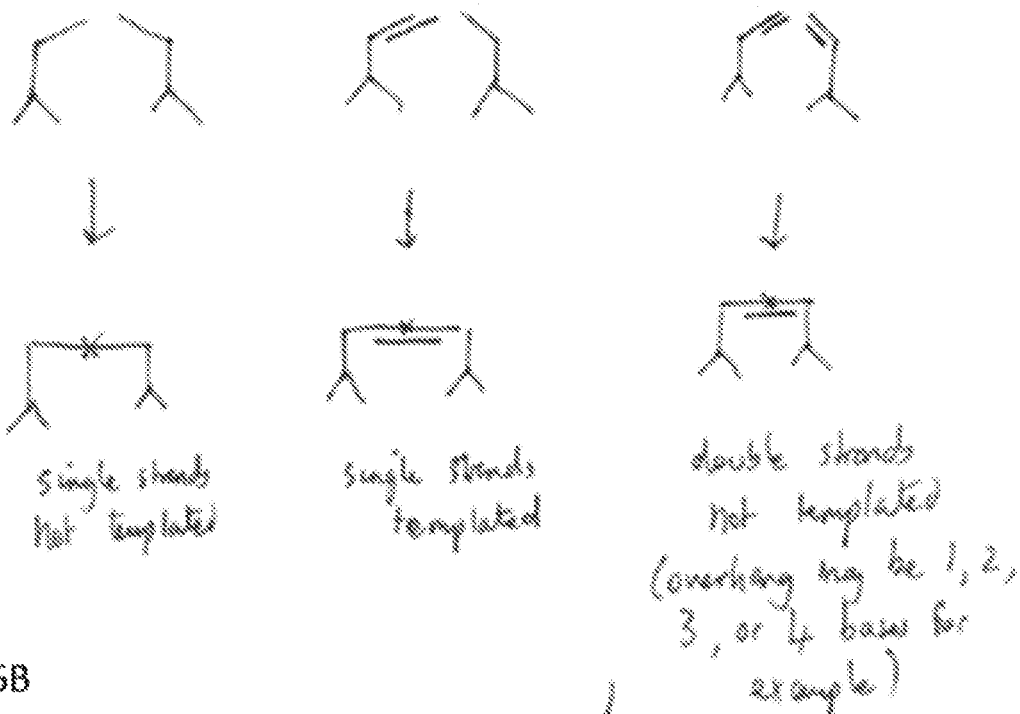
FIGS. 6A-6C illustrate exemplary ways in which a proximity assay can be performed.
Figure 6B:
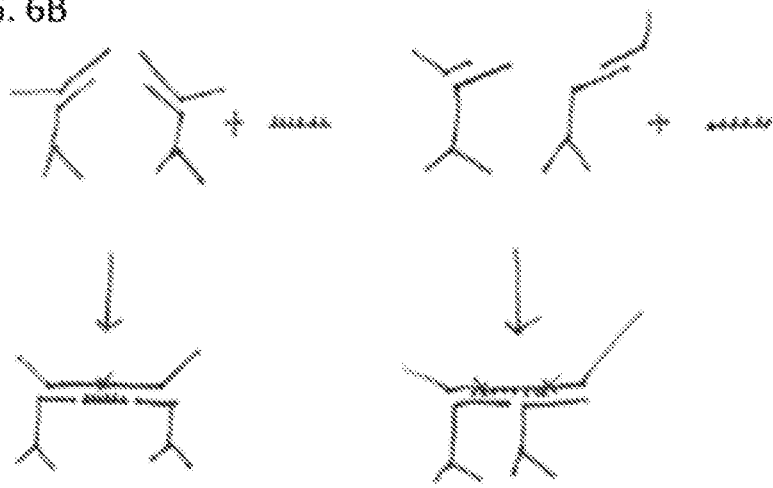
Figure 6C:
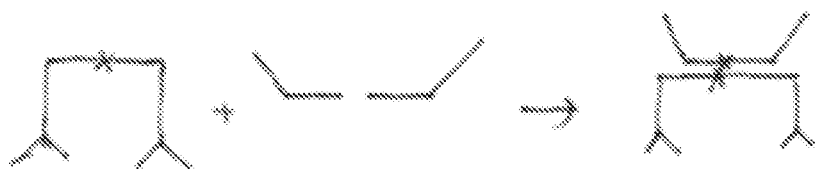

The phrase "proximity assay" as used herein refers to assays in which a new DNA product (e.g., a ligation product or primer extension product) is produced only if two binding events are proximal. In a proximity assay, oligonucleotides are joined to target specific binding agents, such as antibodies, aptamers or oligonucleotide probes. When the target molecules are DNA or RNAs, oligonucleotides can have sequences complementary to the target nucleic acid. When the binding agents bind to sites in a sample that are proximal, the oligonucleotides that are conjugated to those binding agents (the "first" oligonucleotides) are brought into proximity, which permits the production of a new DNA product. The new DNA product can be produced by a variety of different ways. For example, the new DNA product can be produced by an initial enzymic reaction between one first oligonucleotide and another (by a reaction that, e.g., ligates one end of an oligonucleotide to a nearby oligonucleotide, extends one end of an oligonucleotide using a nearby oligonucleotide as a template, or joins one end of an oligonucleotide to a nearby oligonucleotide via a templated gap-fill/ligation reaction, etc.). Examples that involve ligation of two first oligonucleotides together are shown in FIG. 6A. In other embodiments, the new DNA product may be templated by adjacent first oligonucleotides but does not involve ligation between two first oligonucleotides. See, e.g., FIG. 6B. FIG. 6C illustrates another product (referred to as a "reporter probe") that is templated by an initial product produced by joining two first oligonucleotides together or two oligonucleotides that are proximal (FIG. 6B). In FIG. 6A-C, the ligation junctions are indicated with an x. Detecting the nucleic acid reaction products indicates that the corresponding binding agent-oligonucleotide conjugates are bound to sites that are proximal. Thus, binding agent-oligonucleotide conjugates are bound to the sample, and then a reaction (e.g., a ligation, gap-fill/ligation and/or primer extension reaction) is performed while the conjugates are bound to a sample. Products are only produced when two binding agent-oligonucleotide conjugates are bound to sites that are proximal. Certain non-limiting examples of proximity assays include proximity extension assay (PEA) and proximity ligation assay (PLA). For clarity, a proximity assay may involve an initial enzymatic reaction (e.g., ligations, etc.) that occur between the first oligonucleotides (i.e., the oligonucleotides that are attached to the binding agents) and, optionally, a secondary enzymatic reaction that occurs between other oligonucleotides (e.g., reporter oligonucleotides) that enzymatically react with one another (e.g., ligate with one another) using the products of the initial reactions as a template. Alternatively, a proximity assay may involve an initial enzymatic reaction between other oligonucleotides (e.g., reporter oligonucleotides) that enzymatic react with one another (e.g., ligate with one another) in a reaction that is templated by first oligonucleotides that are proximal to one another, and one or more other oligonucleotides that may act as a splint or provide an overhang. Examples are shown in FIG. 6A-C, but other examples would be apparent.

Figure 4:
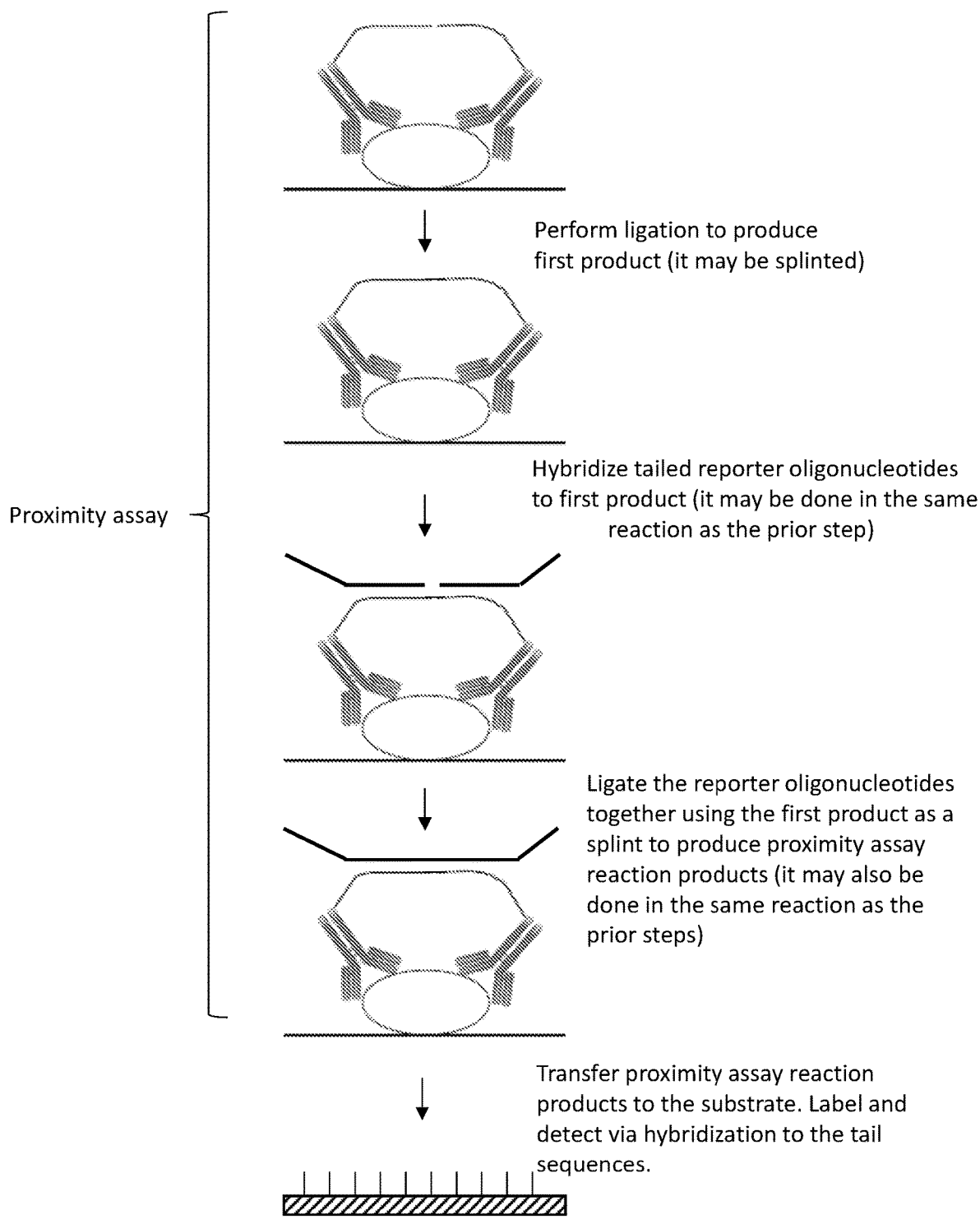
FIG. 4 illustrates how some embodiments of the present method can be implemented.

The phrase "proximity assay reaction products" as used herein refers to the nucleic acids' products of a proximity assay. As will be explained below, such products contain sequence from two oligonucleotides, or their complements, where the sequences are joined together only in the presence of proximal binding events. The exact nature of a proximity assay reaction product may vary depending on how the assay is performed. In some embodiments, a proximity assay reaction product may be the product of an initial reaction that joins together two first oligonucleotides (by ligation or a gap-fill/ligation reaction). In these embodiments, the proximity assay reaction products contain the same sequences as the two oligonucleotides that have been joined together. In other embodiments, a proximity assay reaction product may be the product of an initial reaction that extends the 3' end of an oligonucleotide onto one another. In these embodiments, the proximity assay reaction products contain the same sequences as one of the oligonucleotides and the complement of the other. In some embodiments, a proximity assay reaction product may be a copy of an initial product. In these embodiments, reporter oligonucleotides may be hybridized to an initial product and then ligated together, as schematically illustrated in FIG. 6B and FIG. 4. In other embodiments, the proximity assay reaction product may contain the sequence of two or three oligonucleotides that are joined to one another in a reaction that is templated by two proximal first oligonucleotides, as illustrated in FIG. 6C.

The phrase "proximity extension assay" is intended to refer to a proximity assay that relies on primer extension, where one oligonucleotide uses the other as a template. In this assay, the oligonucleotides that are conjugated to two binding agent-oligonucleotide conjugates that are bound to sites that are proximal hybridize with each other via complementary sequences at the 3' end. The proximity extension assay then involves extending the 3' ends of the hybridized oligonucleotides, for example, using a polymerase, and using hybridized oligonucleotides as templates, to producing nucleic acid reaction products. The resulting nucleic acid reaction products (or their complements) indicate that the corresponding binding agent-oligonucleotide conjugates are bound to sites that are proximal. Certain details of PEA are described by Di Giusto et al. (2005), Nucleic Acids Research, 33(6, e64):1-7; Lundberg et al. (2011) and Nucleic Acids Research, Vol. 39, No. 15; and Greenwood et al. (2015), *Biomolecular Detection and Quantification*, Vol. 4:10-16.

The phrase "proximity ligation assay" or PLA is intended to refer to a proximity assay in which one oligonucleotide is ligated to another oligonucleotide. Such ligation can involve blunt end ligation of single stranded or double stranded oligonucleotides, splint mediated ligation of single stranded oligonucleotides, or ligation of double stranded oligonucleotides having complementary overhangs, for example, overhangs comprising restriction enzyme recognition sites. In certain splint mediated ligations, the oligonucleotides hybridize to a splint in a manner that leaves a gap between the two ends of the oligonucleotides. In such cases, proximity ligation assay involves sealing the gap using a polymerase in a "gap-fill" reaction and then ligating the 3' end of the extended oligonucleotide to the 5' end of the other oligonucleotide. Regardless of the method used to ligate the oligonucleotides, the nucleic acid reaction products resulting from the ligation are analyzed. The resulting nucleic acid reaction products indicate that the corresponding binding agent-oligonucleotide conjugates are bound to sites that are proximal. Certain details of PLA are described by Fredriksson et al. (2002), Nature Biotechnology, 20:473-477; Gullberg et al. (2004), PNAS, 101(22):8420-8424; Wang et al. (2021), *Applied Microbiology and Biotechnology*, Vol. 105, pages 923-935; Greenwood et al. (2015), *Biomolecular Detection and Quantification*, Vol. 4:10-16.

The phrase "preserves the spatial relationship" as used herein characterizes how the nucleic acid reaction products are transferred from a planar biological sample to a support. Particularly, when the nucleic acid reaction products are transferred from a planar biological sample to a support in a manner that preserves the spatial relationship, the relative positions in the x-y plan of different nucleic acid reaction products as present in the planar biological sample do not substantially change when the nucleic acid reaction products are transferred on to the support. For example, the relative positions of different nucleic acid reaction products on the support may deviate slightly from the corresponding relative positions in the planar biological sample because of lateral diffusion of the nucleic acid reaction products during the transfer. Accordingly, the positions of the nucleic acid reaction products on the support indicate the positions of the nucleic acid reaction products on the planar biological sample. Molecules (e.g., reaction products or reporter probe) are most commonly transferred from the planar sample to a planar support in a way that preserves the spatial relationship of the molecules in the sample by placing the support on top of the sample (or vice versa) and transferring the molecules directionally onto the support, so that they move in parallel with one another (approximately) out of the sample and onto the support, where they adhere. When imaging the planar support, the transferred molecules will be positioned as a mirror image compared to the original sample. In an exemplary embodiment, this may be done by placing a planar support (e.g., coverslip or other slide) on top of the sample that is mounted on a slide so that the sample is sandwiched between the substrate and slide. The molecules can transfer via diffusion, for example, but the transfer can be aided by electrostatic, electric, magnetic or other forces. In some embodiments, there may be a small gap (e.g., less than 1 mm, less than 0.5 mm, less than 0.2 mm, less than 100 µm, less than 50 µm, less than 10 µm less than 5 µm or less than 1 vm) between the sample and the support, which gap may be filled with transfer buffer (e.g., low salt buffer) in some cases. The gap may also be maintained using physical structures, spacers or beads positioned between the surfaces.

In another exemplary embodiments the molecules that are transferred from the planar sample are transferred to the support on which the planar sample is located.

The term "proximal" or the phrase "proximally located target sites" as used herein with respect to the location of target sites mean that the target sites are sufficiently close so that the oligonucleotides attached to the binding agent-oligonucleotide conjugates that bind to the target sites interact with each other by for example hybridization or ligation. The target sites can be on the same molecule, for example, two epitopes of one protein. The target sites can also be on different molecules, for example, two epitopes of two different proteins. The target sites can be on different types of molecules, for example, any combination of protein, RNA, DNA, lipid, carbohydrate, etc. The distant between the sites that can be called "proximally located target sites" depends on length of oligonucleotides attached to the binding agent-oligonucleotide conjugates and the presence of any linkers between the binding agents and the oligonucleotides. Typically, proximally located target sites are located at a distance that is less 50 nm, for example, less than 30 nm, less than 20 nm, less than 10 nm, or less than 5 nm.

The phrase "planar support" as used herein refers to a support to which the nucleic acid reaction products from the analyzed planar biological sample are transferred. A wide variety of different substrates can be used as a planar support. The planar support can be made from any suitable support material, such as glass, modified and/or functionalized glass, hydrogels, films, membranes, plastics (including e.g., acrylics, polystyrene, copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon, silicon wafers, and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate.

The term "extending" as used here refers to a ligation reaction (where another oligonucleotide is ligated onto an end of an oligonucleotide), a primer extension reaction (where an oligonucleotide is extended using a polymerase), a gap-fill/ligation reaction, or any combination thereof.

The term "release" as used herein reference refers to an event that places a molecule in solution, not tethered to a support. Release can be done by cleavage of a covalent bond (which may be chemically induced, light induced or enzymatically induced), cleavage of a non-covalent bind, as well as by de-hybridizing the molecule from another molecule, e.g., by heat or using a denaturant.

The phrase "three-dimensional support" as used herein is intended to refer to a three dimensional, permeable solid through which DNA molecules can travel. In many cases, a three-dimensional support can be a cross-linked matrix, e.g., a gel.

As used herein, the term "porous capillary membrane" includes membranes that have relatively densely packed individual capillaries that span the thickness of the membrane, i.e., that go from one side of the membrane to the other, thereby allowing the passage of liquid, but not particles, from one side of the membrane to the other. Examples of porous capillary membranes include, but are not limited to, e.g., anodic aluminum oxide membranes (see below), nanochannel glass membranes, track etched membranes and polytetrafluoroethylene. Nanochannel glass membranes are made of glass and have a high density of uniform channels with diameters from 15 microns to 15 nanometers (see, e.g., Tonucci et al., Advances in Nanophotonics II, AIP Conference Proceedings, 2007 959: 59-71; Pearson et al, Science 1995 270: 68-70 and Tonucci et al., Science 1992 258: 783-785, as well as U.S. Pat. Nos. 5,306,661; 5,332,681; 5,976,444; 6,087,274; 6,376,096; 6,483,640; and 6,599,616, which are incorporated by reference). Track etched membranes are made of a transparent polymer (e.g., polycarbonate, polyethylene terephthalate or polyimide and the like) containing pores having a diameter in the range of 0.01 um to 30 um that have been made by a combination of charged particle bombardment (or irradiation) and chemical etching. Other porous membranes of interest include, but are not limited to amorphous fluoropolymers such as NAFION™, TEFLON AF™, FEFLON FEIP™, and CYTOP™ (DuPont Fluoroproducts, Fayetteville, NC). As would be recognized, a porous capillary membrane may have a surface (e.g., a coating or a chemically modified surface) that is different to the material from which the membrane is made. For example, the surface of a porous capillary membrane may have an altered charge characteristics or altered hydrophobicity or hydrophilic characteristics. In some embodiments, the surface may be coated with amino silane, poly-lysine or another compound to provide a positive charge that helps retain the cells to the surface. Alternatively or in addition, the surface may have a thin layers of a metal (e.g., titanium, gold) deposited therein, which can be linked to other agents that modify the surface properties of the filter.

As used herein, the term "anodic aluminum oxide membrane" includes a regular, self-organized nanoporous membranous structure that is produced when A1 is anodized in certain acidic media. The interior diameter of the pores in the membrane, the distance between the centers of adjacent pores in the membrane, and the distance between the edges of adjacent pores in the membrane can be controlled by the voltage of the deposition, the type of acid, and other parameters. An anodic aluminum oxide membrane is virtually transparent when wet. Anodic aluminum oxide membrane, its properties, and how to make such membranes are reviewed in in detail in a variety of publications including, but not limited to: Li et al (Chem. Mater 1998 10: 2470-2480), Santos et al (Trends on Analytical Chemistry 2013 44: 25-38), Ingham et al (Biotechnology Advances 30 2012 1089-1099) and Poinern et al. (Materials 2011 4: 487-526), which are incorporated by reference herein for those teachings. Anodic aluminum oxide membranes are commercially available under the tradename ANOPORE™ from, e.g., SPI Supplies (West Chester, PA) and from other vendors such as Sykera Technolgoies Inc (Longmont, CO) and Signma-Aldrich (St. Louis, MO) and can be purchased with a support ring.

Other definitions of terms may appear throughout the specification.

DETAILED DESCRIPTION

General Principles

Provided herein, among other things, is a method for analyzing a planar biological sample. In some embodiments, the method may comprise: contacting an oligonucleotide or a conjugate comprising the same (i.e., an oligonucleotide, such as an antibody oligonucleotide conjugate) with a planar biological sample under conditions by which the oligonucleotide or conjugate specifically binds to sites in or on the sample; performing one or more steps to release and/or extend the oligonucleotide in situ, to produce a reporter probe; transferring the reporter probe from the sample to a planar support that does not comprise an array of oligonucleotides, in a way that preserves the spatial relationship of the reporter probe in the sample; and detecting the reporter probe on the support. As will be described in greater detail below, the method may be implemented in a variety of different ways. Some of the general principles of this method are illustrated in FIG. 1.

As shown in FIGS. 2A-2M, the method can be practiced in a number of different ways. For example, in some embodiments, the method may comprise hybridizing oligonucleotides with the sample under conditions by which the oligonucleotides hybridize to endogenous RNA or DNA in the sample and joining together any oligonucleotides that are hybridized to adjacent sites in the RNA or DNA via a ligation or gap-fill/ligation. In other embodiments, the sample comprises ligation products from a proximity ligation assay. In other embodiments, the method may comprise hybridizing oligonucleotides with the sample under conditions by which the oligonucleotides hybridize to the ligation products; and joining together any oligonucleotides that are hybridized to adjacent sites in in the ligation products via a ligation or gap-fill/ligation reaction. In some of these embodiments, the oligonucleotides may be exonuclease-sensitive, but the reporter probe is exonuclease-resistant (after they are joined together). In these embodiments, the method further comprises treating the sample with an exonuclease to remove unligated oligonucleotides and other single stranded nucleic acids. As shown, the term "releases"

is intended to refer to a cleavage event or a de-hybridization event that produces a reporter probe that can travel to the support.

In some embodiments, the method may comprise contacting the tissue sample with antibody-oligonucleotide conjugates with under conditions by which the antibodies bind to sites in or on the sample; and the method may further comprise releasing the oligonucleotides or an extension product thereof from the conjugates antibodies to produce the reporter probe. In any embodiment, the releasing may be done by contacting the biological sample with the support with the biological sample facing the support, and then heating the sample.

In some embodiments, the reporter probe is produced via a ligation, gap-fill or a primer extension reaction.

In some embodiments, the analysis step may be done by microscopy. In these embodiments, the method may comprise hybridizing one or more labeled oligonucleotides, directly or indirectly, to the reporter probe and then analyzing the binding pattern of the labeled oligonucleotides by microscopy. In some embodiments, the labeled probe hybridizes to a ligation junction or extension junction in the reporter probe.

In some embodiments, the method may comprise: (a) performing a proximity assay on one or more pairs of binding agent-oligonucleotide conjugates that are bound to the sample, in situ, to produce proximity assay reaction products; (b) transferring the nucleic acid reaction products into or onto a support in a way that preserves the spatial relationship of the proximity assay reaction products in the sample; and (c) detecting the proximity assay reaction products in or on the support.

As indicated above and below, the proximity assay may involve ligation, primer extension, gap-fill/ligation, or a hybrid thereof and either the initial or "first" products or a complement of the first products (which may be made by ligating two reporter oligonucleotides together using the initial products as a template) may be transferred to the support. For example, in one non-limiting embodiment, the method may comprise performing the proximity assay on one or more pairs of binding agent-oligonucleotide conjugates that are bound to the sample, in situ, to produce first products and transferring the first products to the support. The first products can be produced via a proximity ligation assay or proximity extension assay.

A proximity ligation assay may comprise a templated ligation of oligonucleotides of the binding agent-oligonucleotide conjugates using a splint. The ligation may or may not involve extending the 3' end of one of the oligonucleotides to bring it next to the 5' end of the other oligonucleotide. A proximity extension assay may comprise hybridizing complementary 3' ends of the oligonucleotides of the binding agent-oligonucleotide conjugates and extending the 3' ends of the oligonucleotides using the other hybridized oligonucleotides as templates.

The first products may be released, e.g., cleaved or de-hybridized from the binding agents before transfer to the support.

In some cases, the method may comprise: step (a) comprising: (i) ligating and/or extending the oligonucleotides of the binding agent-oligonucleotide conjugates together to produce the first products; and (ii) ligating a pair of tailed detection oligonucleotides together using the first products as a template to produce the second products, wherein (i) and (ii) are done sequentially or in the same step; and step (b) comprises: transferring the second products onto the support.

Figure 3:
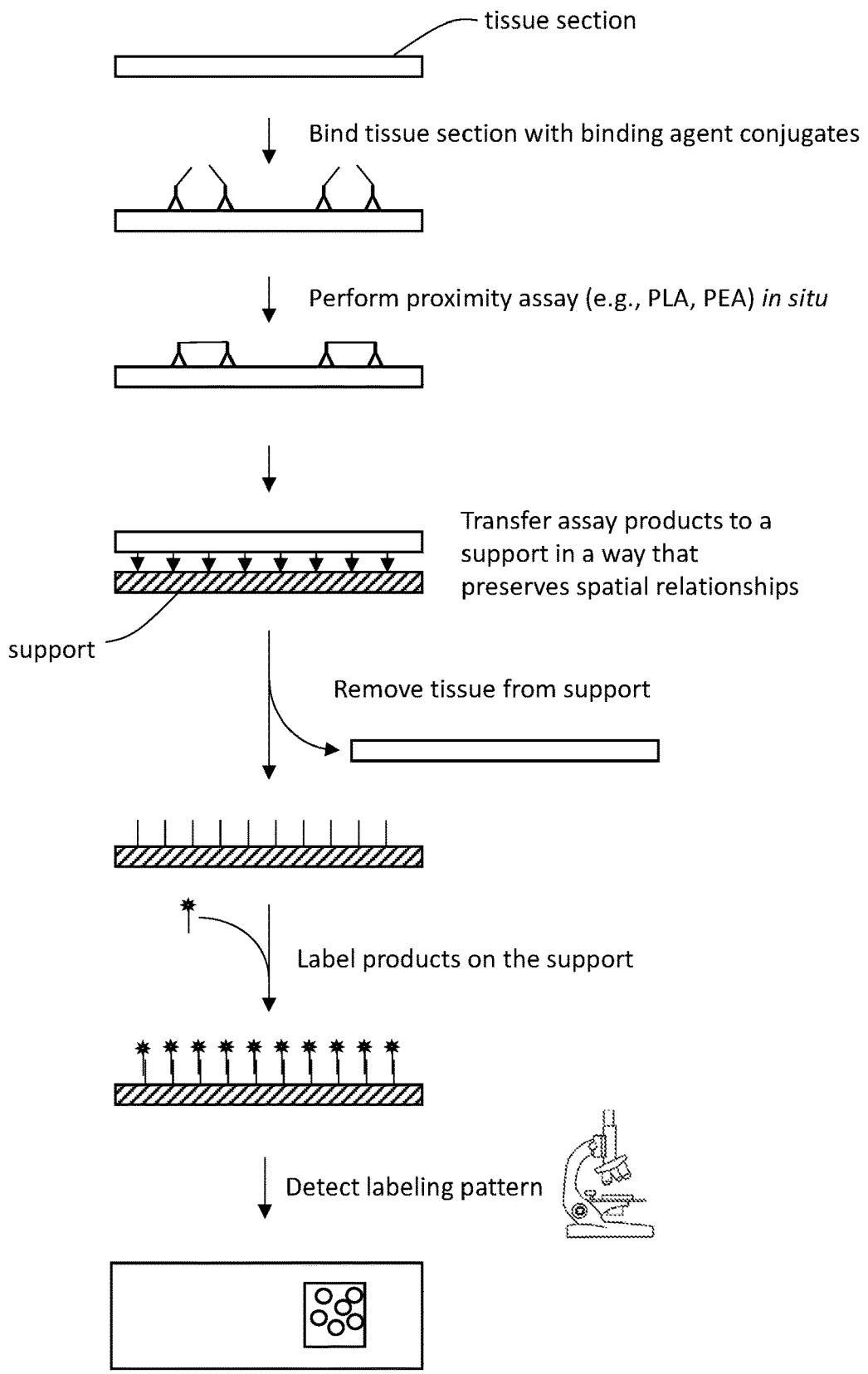
FIG. 3 schematically illustrates how some embodiments of the present method can be implemented.

An example of one implementation of the method is described in FIG. 3. As illustrated in FIG. 3, the method may comprise binding a tissue section with a plurality of binding agent-oligonucleotide conjugates and performing a proximity assay on the bound conjugates, in situ. As shown, the binding agent part of the conjugates may be an antibody. However, in other embodiments, the binding agent may be an aptamer or oligonucleotide probe. The proximity assay may be done using a variety of different methods, e.g., a proximity ligation assay (which results in a first product in which the ends of the oligonucleotides in conjugates that are bind to sites that are proximal become ligated together) or a proximity extension assay (which results in a first product in which one or both oligonucleotides is/are extended using the other as a template). In either case, the first products can be released from the binding agents to which they are tethered and then transferred as the proximity assay reaction products to the support in step (c). In these embodiments, the proximity assay reaction products transferred to the support in step (c) are the first products. In other cases, the first product may be used as splint to ligate a pair of tailed detection oligonucleotides together to make second products. In these embodiments, the proximity assay reaction products transferred to the support in step (c) are the second products. As shown, the proximity assay reaction products are transferred to the support in a way that preserves their spatial relationships in the x-y plane, and then the tissue section is removed from the support. In this method, the proximity assay reaction products become tethered to the support and then detected on the support, e.g., by hybridizing labeled probes to the tethered proximity assay reaction products (directly or indirectly) while they are on the support and analyzing the labelling pattern by microscopy. The support may be a planar substrate such as a slide (which may be coated), or a three-dimensional substrate such as a gel. If the substrate is a planar substrate, then the proximity assay reaction products will be on the substrate. If the substrate is a three-dimensional substrate, then the proximity assay reaction products will be in the substrate.

FIG. 4 illustrates an example of how the proximity assay can be performed. As noted above, the proximity assay can be performed in many different ways. In the embodiment shown, the oligonucleotides of two binding agent-oligonucleotide conjugates that are bound to proximal sites may be ligated together to produce a first product. This ligation reaction may be splinted, but it does not have to be. This embodiment of the method may comprise ligating a pair of tailed reporter oligonucleotides together using the first product as a template to produce the proximity assay reaction products. In these embodiments, the proximity assay reaction products are transferred to the support in step (c).

Figure 5:
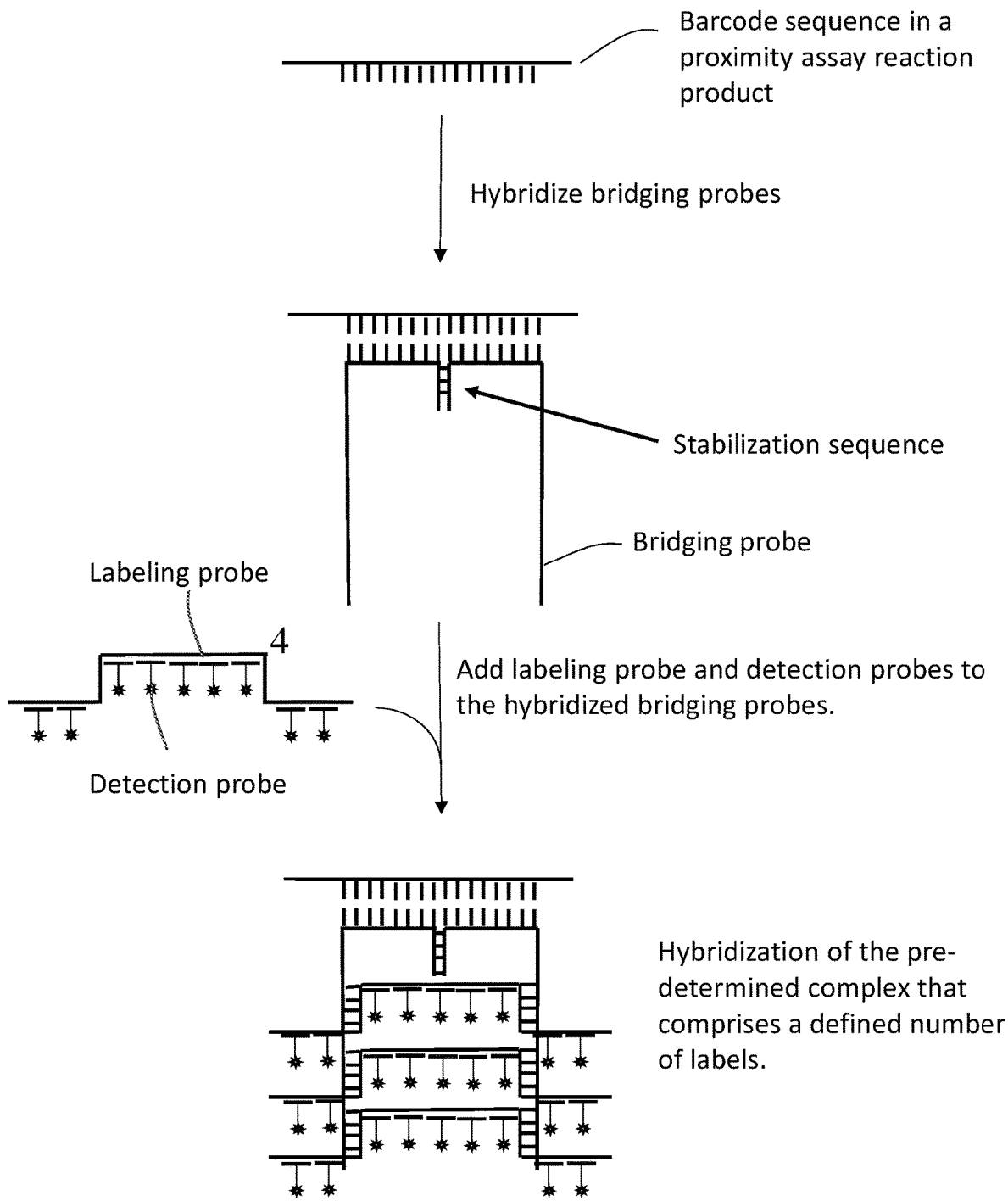
FIG. 5 illustrates how a barcode can be detected on a support using bridging probes, detection probes and labeling probes.

FIG. 5 illustrates an exemplary detection method, the details for which will be provided in greater detail below.

The sites that produce a signal on the support correspond to sites in the planar biological sample. As such, analysis of the sites to which the nucleic acid reaction products are bound on the support can be mapped to a site in the tissue sample. Thus, among other things, the location of different nucleic acid reaction products in or on the support can be used to: 1) determine where specific proteins or proteins are located, for example, using antibodies bind to different sites on the same protein; 2) identify where protein-protein interactions occur, for example, using antibodies that bind to different proteins; and/or or 3) determine post-translation modifications, for example, using one antibody that binds to the modified site in a protein and the other antibody that binds to a different or unmodified site in the protein. Other utilities, e.g., mapping RNAs, protein-RNA interactions, protein-DNA interactions, etc., would be readily apparent.

The present method is free of any nucleic acid amplification steps (e.g., PCR or rolling circle amplification) and the reporter probes/reaction products are transferred from the sample to the support en masse, i.e., together at the same time, without transferring molecules from one area of the sample then another area of the sample, and so on. The method is sequencing free and does not make use of oligonucleotides that have spatial barcodes, i.e., a sequence that corresponds to a coordinate in an x-y plane, or an array of the same (where each element of the array has a sequence that identifies its location on the array). There is no proximity assay is done on the transferred molecules (on the support or otherwise); rather the detection is done by hybridization of labeled probes to the transferred molecules and imaging, e.g., by microscopy. For clarity, the planar sample used in the present method is not a liquid sample. Most commonly (although not always) the sample is a tissue section. None of reporter probes/reaction products is circular; rather they are linear and often have either an affinity group at one end and are protected at the other end such that they are protected from exonuclease degradation and can adhere to the support. For clarity, molecules (e.g., RNA) that are endogenous to the sample (i.e., "biological molecules") are not transferred to or analyzed on the support; rather, a synthetically made molecule (e.g., an oligonucleotide or cleavage, ligation or extension product of the same) is transferred and analyzed.

In an exemplary embodiment, the initial steps of the method may join together pairs oligonucleotides. In these embodiments, one of the oligonucleotides will contain a biotin group at one end and the other of which will contain a modification that makes it exonuclease resistant at the other end. In their unligated form, both oligonucleotides are exonuclease sensitive. However, when they are ligated together the ligation product is exonuclease resistant. This ligation product is transferred to a support that is coated in streptavidin or avidin, to which the product adheres. In order to reduce background, the sample may be treated with one or more exonucleases (after ligation) and/or the substrate may be treated with one or more exonucleases (after the products have been transferred onto the support.

In any embodiment, the method may further comprise modifying the oligonucleotide, extension product thereof or reporter molecule using a DNA modification enzyme, e.g., a ligase, kinase, exonuclease, terminal transferase, deaminase, deglycosylase, methylase, phosphatase, linking it to a chemical moiety or binding agent etc., in situ, during transfer or after transfer, as required.

Binding Agents

A binding agent can be an antibody or an antigen binding fragment of an antibody, such as Fab, Fv, scFv, F(ab')$_2$, and Fd. A binding agent can also be a scaffold protein evolved for affinity like and Affibody or similar affinity proteins.

In some cases, an antibody against an antigen is a monoclonal antibody.

In one embodiment, an antibody against an antigen is a split polyclonal antibody. A split polyclonal antibody is produced by raising polyclonal antiserum against an antigen and splitting the antiserum into two portions. Oligonucleotides having a specific sequence are conjugated to antibodies against the antigen in one portion of the polyclonal antiserum and oligonucleotides having a different specific sequence are conjugated to the antibodies against the antigen in the other portion.

A binding agent can also be an aptamer that specifically binds to a protein, carbohydrate, or even small molecule.

Moreover, a binding agent can be an oligonucleotide that specifically binds to a target sequence, such as a specific target sequence in an RNA or DNA. An oligonucleotide binding agent can specifically bind to a target RNA, such as a messenger RNA (mRNA), transfer RNA (tRNA), or ribosomal RNA (rRNA). An oligonucleotide binding agent can also specifically bind to a target DNA, such as chromosomal DNA or extra-chromosomal DNA. Extra-chromosomal DNA can be an organelle DNA, such as mitochondrial DNA or chloroplast DNA.

Binding Target Sites

The binding agents can specifically bind to binding target sites, such as site on a protein, RNA, DNA, carbohydrate, proteoglycans, lipids, and other biomolecules.

The sites to which the binding agents bind may be on the same protein or on different proteins. For example, the binding agents may bind to different epitopes in the same protein. In some cases, one of the binding agents used in the proximity assay may binds to a site in a protein that is not post-translationally modified, whereas the other binding agent may specifically bind to the same protein at a site that is post-translationally modified. The post-translational modification can be for example phosphorylation, glycosylation, ubiquitination, nitrosylation, methylation, acetylation, and lipidation, although many other types of post-translational are known.

As noted above, an RNA binding target can be any type of RNA including mRNA, tRNA, non-coding RNA, or rRNA.

Also, a DNA binding target can be chromosomal DNA or extra-chromosomal DNA. Extra-chromosomal DNA can be an organelle DNA, such as mitochondrial DNA or chloroplast DNA.

In some cases, the oligonucleotide probes can be used to detect mutations in the DNA. In such cases, the target DNA is converted into single stranded without disrupting the tissue and other molecules. For example, specific targets in the DNA molecules can be converted into single stranded state by using nicking enzymes or CRISPR-based targeting. The single stranded DNA so produced can be digested, for example, using 3' or 5' specific exonuclease, to leave only one strand of the target DNA for the analysis of the mutation.

Target molecules can also be of viral or bacterial origin.

Proximity Assays

As noted above and below, a proximity assay may be done in a variety of different ways, which methods may involve ligation, extension, or gap-fill/ligation etc. In some cases (as illustrated in FIG. 4), the method may comprise: step (a) comprising: (i) ligating and/or extending the oligonucleotides of the binding agent-oligonucleotide conjugates together to produce the first products; and (ii) ligating a pair of tailed reporter oligonucleotides together using the first products as a template to produce the proximity assay reaction products, wherein (i) and (ii) are done sequentially or in the same step. In other embodiments, step (a) may comprise ligating and/or extending the oligonucleotides of the binding agent-oligonucleotide conjugates to produce the proximity assay reaction products. In these embodiments, the proximity assay reaction products may be cleaved from the binding agents prior to transfer to the support.

Proximity Ligation Assay

In some embodiments, step (a) comprises PLA. Any suitable method can be used to ligate the oligonucleotides conjugated to the binding agent-oligonucleotide conjugates in a PLA. For example, the oligonucleotides from binding agent-oligonucleotide conjugates can be ligated together via: a non-templated ligation of single stranded ends of the nucleic acids, a non-templated ligation of double stranded ends of the nucleic acids, a templated ligation using a splint, or overhang mediated ligation of double stranded nucleic acids using complementary overhangs.

In one embodiment, PLA comprises contacting the biological sample with a first target specific binding agent-oligonucleotide conjugate comprising a first target oligonucleotide and a second target specific binding agent-oligonucleotide conjugate comprising a second target oligonucleotide. Plurality of pairs of first and second target specific binding agent-oligonucleotide conjugates can also be used in a multiplex reaction.

In a pair of target specific binding agent-oligonucleotide conjugates, the first target oligonucleotide has a free 3' end and comprises from the 5' end: one or more barcodes unique for the first target and a first splint hybridization region; and the second target oligonucleotide has a free 5' end and comprises from the 3' end: one or more barcodes unique for the second target and a second splint hybridization region.

Upon binding of the pairs of target specific binding agent-oligonucleotide conjugates to the corresponding target sites, the biological sample is contacted with a splint oligonucleotide that hybridizes at two ends with the first and the second oligonucleotides that are brought proximal to each other via the binding of the first target specific binding agent to the first target site and the second target specific binding agent to the second target site.

The splint oligonucleotide can bring together the 5' and 3' ends of the first and second oligonucleotides, in which case, the two oligonucleotides can be ligated to produce a ligated oligonucleotide. The splint oligonucleotide can be designed so that the 3' end of one oligonucleotide is not proximal to the 5' end of the other oligonucleotide. In such cases, the 3' end can be extended, for example, using a polymerase to extend the 3' end of the first oligonucleotide towards the 5' end of the second oligonucleotide. The two oligonucleotides can then be ligated to produce the ligated oligonucleotide.

Thus, in some cases, the ligation assay may comprise: (i) labeling the planar biological sample with multiple pairs of binding agent-oligonucleotide conjugates, (ii) hybridizing splint oligonucleotides to the sample after (i), wherein the splint oligonucleotides hybridize with the ends of the oligonucleotides in different conjugates, and (iii) ligating together the ends of any oligonucleotides in the conjugates that are hybridized to the same splint oligonucleotide, to produce the nucleic acid reaction products.

In some embodiments, the ligation assay may comprise ligating the oligonucleotides of the binding agent-oligonucleotide conjugates via: a templated or non-templated ligation of single stranded ends of the oligonucleotides, a non-templated ligation of double stranded ends of the oligonucleotides, or overhang mediated ligation of double stranded oligonucleotides using complementary overhangs. Templated ligation embodiments may be accomplished using a ligation splint, wherein the splint is designed so that the 3' end of a first oligonucleotide of a first binding agent-oligonucleotide conjugate is next to the 5' end of a second oligonucleotide of a second binding agent-oligonucleotide conjugate, and wherein the method comprises ligating the 5' and 3' ends of the first and second oligonucleotides.

Oligonucleotides can also be joined to one another via a gap-fill/ligation reaction, in which two oligonucleotides hybridize to the opposing ends of a template, and the gap is filled by polymerization and the nick is sealed by ligation.

Many variations of these assays are known. For example, "UnFold" probes may be used in some embodiments. See, e.g., Klaesson et al (Sci Rep 8, 5400 (2018)).

Proximity Extension Assay (PEA)

In some embodiments, step (a) comprises PEA. Any suitable method can be used to produce nucleic acid reaction products from the oligonucleotides from the binding agents-oligonucleotide conjugates. In one embodiment, PEA comprises contacting the biological sample with a first target specific binding agent-oligonucleotide conjugate comprising a first oligonucleotide and a second target specific binding agent-oligonucleotide conjugate comprising a second oligonucleotide. Plurality of pairs of first and second target specific binding agent-oligonucleotide conjugates can also be used in a multiplex reaction.

In a pair of specific binding agent-oligonucleotide conjugates, the free 3' ends of the first and the second oligonucleotides have sequences that are complementary to each other and, hence, the free ends hybridize to each other. These free 3' ends can be extended, for example, using a polymerase, to create double stranded oligonucleotides that contain sequences of both the first and the second oligonucleotides.

Thus, in some cases, PEA comprises:
(i) labeling the planar biological sample with multiple pairs of binding agent-oligonucleotide conjugates,
(ii) hybridizing complementary 3' ends of the oligonucleotides and extending the 3' ends of the oligonucleotides using the other hybridized oligonucleotides as templates to produce the nucleic acid reaction products.

Hybrid Assays

In some embodiments, multiple combinations of interactions are analyzed using the method disclosed herein and a combination of PLA and PEA is used to produce the nucleic acid reaction products.

For example, nucleic acid reaction products are produced from certain interactions using PLA and nucleic acid reaction products are produced from certain other interactions using PEA. Certain details of PLA and PEA are described above and can be used in the hybrid methods envisioned herein.

RNA Detection Using Ligation Assay

In some cases, the method involves detecting RNA using a ligation assay. Particularly, the reporter polynucleotides can be designed that hybridize with certain sequences in the target RNA. The probes can have tails containing barcodes. In some cases, the oligonucleotide probes comprise DNA nucleotides, except towards the ligation site, where the oligonucleotides comprise RNA nucleotides. Thus, the oligonucleotide probes can be a hybrid of DNA and RNA nucleotides. Alternatively, the reporter polynucleotides can comprise hairpin structures so that the oligonucleotides ligate with each other upon being brought together via the target RNA.

Proximity Assay with Three or More Binding Agents

In some cases, proximity assay is performed with three or more binding agents. An example of such assay is described by Schallmeiner et al. (2007), *Nat. Methods.;* 4(2):135-7.

In some cases, three binding agent-oligonucleotide conjugates are used, wherein a first binding agent-oligonucleotide conjugate is conjugated to a first oligonucleotide, the second binding agent-oligonucleotide conjugate is conjugated to a second oligonucleotide, and the third binding agent-oligonucleotide conjugate is conjugated to a splint oligonucleotide. If the three oligonucleotides are brought proximal to each other via binding of the three binding agents to proximal binding targets, the splint oligonucleotide hybridizes with the first and the second oligonucleotides, which can be ligated to produce nucleic acid reaction product. Thus, the production of the nucleic acid reaction product indicates that the oligonucleotides are conjugated to binding agents that are bound to sites that are proximal.

Reporter Probes

In some embodiments, the first products, i.e., the nucleic acids produced from an initial primer extension, ligation or gap-fill/ligation may be used as a ligation template or ("splint") to ligate together two or more other oligonucleotides (referred to herein as "reporter oligonucleotides") to produce a reporter probe. In these embodiments, the reporter probe is the proximity assay reaction product that is transferred to the substrate. An example of this embodiment is illustrated in FIG. 4. Alternatively, reporter probes may be made by hybridization to oligonucleotides that are proximal to one another, without joining the first oligonucleotides together (see, e.g., FIG. 6B).

In these embodiments, the first products are used as a template to ligate together a pair of reporter oligonucleotides (a "first" reporter oligonucleotide and a "second" reporter oligonucleotide) to produce the proximity assay reaction product. As shown, the reporter oligonucleotides may be "tailed" such that they contain a first sequence that hybridize with the first products and tail sequence that does not hybridize with the first products. As shown, one of the reporter oligonucleotides has a 5' tail and the other has a 3' tail. The tails can be of any suitable length, e.g., up 20-200 bases and may be used for detection after the proximity assay reaction products have been transferred to the support.

One or more of the tails can contain a modification. For example, the tails may contain a binding member, a reactive group or a moiety that facilitates transfer of the reporter probes to the support, tethering of the probes on or in the support, or modifications to protect it from exonuclease activity. For example, in some embodiments, one of the ends of a reporter oligonucleotide may contain a chemistry for linking the products to a substrate such as a glass slide. These modifications include, but are not limited a hydrazide group (I-LINKER™), an amine group, e.g., an amine covalently linked to an activated carboxylate group or succinimidyl ester, a thiol group, e.g., a thiol group covalently linked via an alkylating reagent such as an iodoacetamide or maleimide, an acrylic group (ACRYDITE™), which may be linked through a thioether, a digoxigenin NHS Ester group, a cholesterol-TEG group, or biotin, etc. Such groups may become tethered to glass slides using the following chemistries: $NH_2$-modified oligonucleotides bind to epoxy silane or isothiocyanate coated glass slide, succinylated oligonucleotides bind to aminophenyl or aminopropyl-derivatized glass slides, disulfide modified oligonucleotides bind to mercaptosilanized glass slides and hydrazide oligonucleotides bind to aldehyde or epoxide modified glass slides. Click reactive groups could be used in some circumstances. In embodiment, a nucleic acid may be anchored to a support by a biotin-avidin/streptavidin/neutravidin interaction, where the nucleic acid contains a biotin moiety and the support is coated in avidin, streptavidin or neutravidin.

As would be apparent, the reporter oligonucleotides can be designed so that their ends are adjacent when they are hybridized to the first products. Alternatively, the ends do not need to be adjacent, and the gap can be filled in and sealed.

In some embodiments, the reporter oligonucleotides may be part of the oligonucleotides that are conjugated to the binding agents and cleaved off and ligated together during the proximity assay. For example, the oligonucleotides that are conjugated to the binding agents may contain a hairpin or loops that contains more uracils (or restriction sites) that allow the reporter oligonucleotides and/or the reporter probe to be cleaved from those oligonucleotides during the reaction (see, e.g., Klaesson et al (Sci Rep 2018 8, 5400)).

In another embodiment, the reporter oligonucleotides may be pre-hybridized to the oligonucleotides that are conjugated to the binding agents, which also avoids adding the reporter oligonucleotides separately. In addition, the resulting DNA complex can also be designed to have regions that can be cleaved or removed to expose single stranded sequences that can be used for joining binding agents and/or detection oligonucleotides by ligation using splint mediated, or overhang mediated ligation and thereby eliminate presence of single stranded regions during incubation and binding of the binding agents, and also ensure that the detection oligonucleotides are present on each binding agent to increase efficiency. Using two separate oligonucleotides reduces the length of each oligonucleotide that need to be synthesized and may increase oligonucleotide quality by reducing synthesis challenges of long ssDNA, in particular if oligonucleotides are to be modified at specific sites.

RNA Detection Using Reporter Polynucleotides

In some cases, an RNA target from a planar biological sample is directly used as a template to produce a reporter polynucleotide, i.e., a proximity assay is not performed to produce a nucleic acid reaction product, but the RNA target is used as a template to produce a reporter polynucleotide. For example, a first reporter probe and a second reporter probes can be designed so that upon binding to an RNA target, the 5' and 3' ends of the first and second reporter probes are proximal to each other, in which case, the two reporter probes can be ligated to produce a reporter polynucleotide.

The first reporter probe and the second reporter probes can also be designed so that upon binding to an RNA target, the 3' end of one reporter probe is not proximal to the 5' end of the other reporter probe. In such cases, the 3' end can be extended, for example, using a polymerase to bring together the 5' and 3' ends of the first and second reporter probes, which can then be ligated to produce the reporter polynucleotide.

Exonuclease Digestion

In any embodiment, the method may comprise a digestion with one or more exonucleases (e.g., both exonuclease I and exonuclease III, although other one or more other exonucleases, e.g., exonuclease T, exonuclease V, exonuclease VII, T5 exonuclease or T7 exonuclease could be used instead in some cases) to remove unligated reporter oligonucleotides and other single stranded nucleic acids. This digestion can be done any time after the initial proximity assay reaction products have been produced. For example, the digestion may be done in situ, during the transfer step or after the transfer step. In these embodiments, the oligonucleotides that are used in the proximity assay (e.g., the first oligonucleotides that are attached the binding agents, or the reporter oligonucleotides) may be designed to be produce exonuclease resistant products, which allows those products to survive the exonuclease step. For example, if reporter oligonucleotides are used, then one of the reporter oligonucleotides may have a protected 3' end and/or the other of the reporter oligonucleotides may have a protected 5' end, for example. Oligonucleotides can be made exonuclease-resistant by addition of an exonuclease-resistant linkage, such as a phosphorothioate linkage, although other linkages can be used. In alternative embodiments, the reporter oligonucleotides and other single stranded DNA molecules may be removed by washing at a temperature that is lower than the Tm of the proximity assay reaction product:template duplex.

Increasing Signal Using Redundant Probe Sets and Decreasing Signal Using Defect Ligation Events In order to generate more signal from rare binding events, several nucleic acid reaction products can be generated from each binding event. For protein targets this can be achieve using binding agents that are each conjugated to several oligonucleotides. This, in turn, generates several assay products in the proximity assay. For RNA and DNA targets multiple probe sets can be designed targeting each RNA molecule or DNA loci so that each target produces many nucleic acid reaction products. At least 2 or more or at least 5 or more or at least 10 or more nucleic acids can be used per binder directly or indirectly associated with the binding agent. At least 2 or more or at least 5 or more or at least 10 or more at least or more probe pairs can be used to target RNA or DNA sequences.

The number of probe sets that are used can be calibrated using the expression level of the target molecule to balance the number of reporter molecules generated between different targets. Also probes designed to analyze targets present in very high abundance can be designed to have a fraction of the probes that are defect and unable to generate a reporter molecule. This can be used to decrease the signal from for example highly expressed proteins or RNAs which otherwise would take a very large amount of detection real estate on the support.

Transfer of Nucleic Acid Reaction Products to a Solid Support

The nucleic acid reaction products produced in a proximity assay or via reporter probes can be transferred to a solid support. In certain embodiments, the nucleic acid reaction products produced are cleaved or in other ways dissociated from the corresponding binding agents and then transferred to the support. Transferring the nucleic acid reaction products onto a support is performed in a manner that preserves the spatial relationship of the nucleic acid reaction products in the sample.

In some embodiments, nucleic acid reaction products are produced that have a first binding member of the specific binding pair and the nucleic acid reaction products are transferred to a support comprising a second binding member of the specific binding pair. Thus, the specific binding between the first and the second binding members of the specific binding pair immobilizes the nucleic acid reaction products on to the support. In one embodiment, the specific binding pair comprises biotin and streptavidin.

Planar Support

In some embodiments, the support may be planar. A planar support can be the same solid support on which the tissue section is immobilized. In this case, the binding between the nucleic acid reaction products and the solid support is inducible. In one example of such inducible reaction, click chemistry is used that requires an inducer, such as copper, to create a covalent bond. In another example, the nucleic acid reaction products are ligated to an oligonucleotide immobilized on the solid support. Such ligation can be performed using a templating splint that brings together the ends of the nucleic acid reaction products and an oligonucleotide immobilized to the solid support.

Alternatively, another planar support can used to transfer the reporter polynucleotides from the tissue. The transfer of reporter polynucleotides from the tissue to the planar support can be accelerated using electrophoresis. In some embodiments, electrostatic interactions (e.g., between the molecules being transferred and a positively charged surface (which is the case for poly-lysine coated slides) may facilitate movement of the molecules to the support. In some embodiments, the support may be coated in avidin or streptavidin, which binds to a biotinylated reporter molecule. In some instances, magnetism is used to accelerate the transfer using magnetic or paramagnetic beads associated with the reporter molecules.

In one embodiment, the planar support to which the nucleic acid reaction products from the tissue are transferred does not have oligonucleotides attached to it. Therefore, the nucleic acid reaction products are transferred and attached to the planar support via means other than through oligonucleotides.

As discussed above, one such method of attaching nucleic acid reaction products to a planar support without oligonucleotides involves producing copied nucleic acid reaction products or reporter polynucleotides that have a first binding member of the specific binding pair. The reporter polynucleotides are transferred to a planar support comprising a second binding member of the specific binding pair. Thus, the specific binding between the first and the second binding members of the specific binding pair immobilizes the nucleic acid reaction products on to the planar support. For example, the specific binding pair comprises biotin and streptavidin.

Certain additional methods of attaching nucleic acid reaction products to a planar support without oligonucleotides include modifying the planar support to provide certain functional groups that react with and form bonds with nucleic acid reaction products that contain other functional groups that react with the functional groups on the planar support.

Further such methods of attaching nucleic acid reaction products to a planar support without oligonucleotides include: modifying the oligonucleotides to contain an amino group that reacts with the epoxy silane or isothiocyanate coated planar support; modifying the oligonucleotides to contain the succinate group that reacts with the aminophenyl or aminopropyl-derivatized planar support; modifying the oligonucleotides to contain the disulfide group that reacts with the mercaptosilanized solid support; modifying the oligonucleotides to contain the hydrazide group that reacts with the aldehyde or epoxide group containing solid support; and binding oligonucleotides to a planar support that contains poly-lysine. Furthermore, any additional suitable protocols for attaching nucleic acid reaction products to planar support without oligonucleotides can be used.

Removal of Tissue

In any embodiment, the method disclosed herein comprises removing the planar biological sample from the support to leave the nucleic acid reaction products on or in the support (FIGS. 1 and 3).

A planar biological sample can be removed from the support in any suitable manner. For example, the substrate, such as the glass slide on which the planar biological sample is placed can simply be moved away from the support. Because the nucleic acid reaction products are bound to the support, either covalently or non-covalently, the nucleic acid reaction products remain attached to the support while the remaining tissue is removed from the support.

Any remnants of the biological sample can be removed via enzymatic action. For example, the support can be treated with enzymes that degrade biomolecules other than polynucleotides thereby only removing the biomolecules other than the nucleic acids. Moreover, if the nucleic acid reaction products comprise DNA, the support can be treated with RNA degrading enzymes to remove contaminating RNAs.

Labeling and Detection

In some cases, the methods disclosed herein comprise detecting the positions of the nucleic acid reaction products on the support preferably as individual molecules. Such detecting involves binding detectably labeled probes to the nucleic acid reaction products on or in a support and detecting the labeled probes to determine the distribution of the nucleic acid reaction products on or in the support.

In one embodiment, detecting the nucleic acid reaction products on or in the support comprises:
(i) labeling the nucleic acid reaction products on or in the support; and
(ii) imaging the support to produce an image of the sites to which the nucleic acid reaction products have bound to the support.

In some embodiments, the proximity assay reaction products are detected in or on the support by hybridization to a defined nucleic acid structure composed of a predetermined number of oligonucleotides and a predetermined number of labeled oligonucleotides. In these embodiments, the structure may be nucleated by at least two hybridization events to the proximity assay reaction products. In these embodiments, the at least two hybridization events comprise a first hybridization to a first sequence in a proximity assay reaction product and a second hybridization to a second sequence in the proximity assay reaction product. An example is such a nucleic acid structure illustrated in FIG. 5.

In these embodiments, in order to quantify the nucleic acid reaction products as single molecules it may be advantageous to incorporate a defined number of detection labels per nucleic acid reaction product in order to get a reproducible and stable signal from all molecules. Although approaches like RCA or other clonal amplification strategies could be used for detecting the transferred molecules on the planar support these typically do not incorporate a defined umber of labels per molecule can create uneven signal from different molecules causing crowding if signals are large and undetectable signals if signals are weak. By designing a programmable hybridization, a specific number of hybridization events occur for each detected target resulting in a predetermined and specific number oligonucleotides and labels to be incorporated into each formed nucleic acid structure. These structures can advantageously be designed so that two or more initial independent hybridization events to the target are required in order to nucleate formation of the nucleic acid structure that is detected. Once the initial hybridizations to the nucleic acid reaction product have occurred these will stably attract the hybridizations and formation of the remaining oligonucleotides. The hybridization events forming the nucleic acid structure can advantageously be separated up into two or more steps since, in some cases, it might be challenging to design the oligonucleotides to that the entire structure does not spontaneously form if all oligonucleotides are present in the same solution.

The detection reaction is also advantageously designed so that single labels or labelling structures that are present in each step do not generate a detectable signal if the label or labelling structure would adsorb non-specifically to the surface.

In any embodiment, the molecules that are transferred to the support may contain sequences that are complementary to sequences in the probe system being used. These sequences may be in the tails of the reporter oligonucleotides (which become the reporter probes), or they can be built into the oligonucleotides that are conjugated to the binding agents, for example.

Each of these sequences may have multiple binding sites for the probe system, thereby allowing the support to be interrogated by multiple rounds of hybridization, reading, and signal removal. Such sequences may be referred to as "barcode" sequences herein. In some embodiments, the identity of a reporter molecule in or on the support may be determined by reading a code that correspond to whether the product hybridizes or does not hybridize to each probe of a set of probes as described in e.g., Goransson et al (Nucl. Acids Res 0.2009 37:e7), Moffitt et al (Methods Enzymol. 2016 572: 1-49) and Moffit et al (Proc. Natl. Acad. Sci. 2016 113: 11046-51).

Therefore, in some cases, the method may comprise determining which combination of probes bind to the reporter molecule. Such detection can be mediated by specific detection and labeling probes that specifically bind to those sequences. Designing and detecting labeled probes that bind to specific barcode sequences is well known in the art and such embodiments are within the purview of the invention.

In some cases, specific detection probes are added in multiple cycles and in each cycle different barcode(s) are labelled thereby detecting the binary string of barcodes present in each nucleic acid reaction product. Each cycle can comprise labeling, washing, imaging, and eliminating the detection probes before the next cycle begins.

DNA Origami

In some cases, DNA origami is used to label and detect the nucleic acid reaction products on the planar surface.

"DNA origami" as used herein refers to mixing and sequence dependent folding of DNA molecules to create two- and three-dimensional shapes. The two- and three-dimensional shapes are at the nanoscale level. The shapes are produced based on the sequences of the mixed DNA molecules that hybridize with each other in specific manner to form the two- or three-dimensional structure.

Therefore, in some cases, bridging probes, labeling probes, and/or detection probes are produced such that when mixed together they form two- or three-dimensional structures that specifically bind to the nucleic acid reaction products on the surface.

DNA Origami structures can advantageously be designed so that co localization by hybridization and/or ligation of two or more seeding oligonucleotides, optionally introduced in a separate initial step, to a barcode is required to initiate formation of the DNA origami structure to avoid unspecific signal generation created e.g., by background adsorption of oligonucleotides.

Detection Systems

In some embodiments, the detection system may be designed so that in each cycle a pair of oligonucleotides in the detection system cooperatively hybridize to a respective barcode sequence in a transferred reporter molecule. One example of such labeling and detection is shown in FIG. 5. In this example, hybridization of the bridging detection probes to the barcode is stabilized by a relatively short (of, e.g., 4-10 bp) complementary sequence at the ends of the bridging detection probes (FIG. 5). Alternatively, complex could be stabilized by ligating the ends of the bridging probes together.

As illustrated in FIG. 5, in some embodiments, the method may comprise hybridizing the proximity assay reaction products that are tethered to the support with a pair of bridging probes comprising a first bridging probe and a second bridging, each bridging probe comprising a barcode hybridization region that hybridizes to a portion of the barcode.

In some cases, the first bridging probe further comprises a first barcode indicator region (i.e., a region that does not hybridize to the barcode sequence) and the second bridging probe further comprises a second barcode indicator region (i.e., another region that does not hybridize to the barcode sequence), wherein hybridization of the first and the second bridging probes to the barcode brings the first and second barcode indicator regions proximal to each other.

In these embodiments, after the bridging probes are hybridized to the barcodes, the remainder of the detection system (which may be composed of labeling probes and detection probes, as illustrated in FIG. 5) may be added sequentially or as one. As shown, the detection system may comprise a labeling probe that hybridizes to both of the first and second indicator regions, as well as detection probes that hybridize to the labeling probe. The detection probes can be prehybridized to the labeling probes, however this is not essential. As shown in FIG. 5, the labeling probes hybridize to a pair of bridging probes. Thus, in some cases, detecting the bridging probes hybridized to the barcode may comprise: hybridizing a labeling probe to the barcode indicator regions, wherein the labeling probe comprises a first labeling region that hybridizes with the first barcode indicator region, and a second labeling region that hybridizes with the second barcode indicator region. As shown, detection probes (which may be labeled with a fluorophore) are hybridized with the labeling probe.

As shown, multiple, for example, five to ten, up to 20 or more, detection probes can hybridize to one pair of labeling probes. Given that one pair of bridging probes are attached to the proximity assay reaction product, several detection probes may be hybridized to one labeling probe to register a signal over background (FIG. 5). This design ensures that signal generation specificity is maintained, and the signals are uniform from one hybridization event to another. Individual bridging probes do not create background if they stick to the surface and individual labeling probes may not create sufficient signal to generate a signal over background. Thus, a detectable signal may only be produced when multiple labeling probes are hybridized to a pair of bridging probes. Multiple labels with different fluorophores can be used so that multiple barcodes can be detected in one labeling cycle. The hybridization chemistry is designed to have a defined number of fluorophores for each target molecules.

Thus, by repeating the cycles of labeling and detection, locations can be determined for a plurality of barcodes on the support. Based on the locations of the barcodes on the support and known information about the binding agents that are conjugated to the oligonucleotides containing those barcodes, a map of binding targets in the planar biological sample can be created.

Mapping Nucleic Acid Reaction Products to the Planar Biological Sample

In some embodiments, in addition to detecting the locations of barcodes and thus, creating a map of binding targets in the planar biological sample, the method further comprises producing an optical image of the planar biological sample. An optical image of the planar biological sample can be produced via staining the sample with a microscopy stain. The image of the sample can then be compared or overlaid to the map of binding targets in the planar biological sample. Such overlay can be useful in determining the distribution of certain biomolecules, i.e., binding targets of the binding agents used in the proximity assay, within different regions of the biological sample.

The sample may be stained using a cytological stain, either before or after performing the method described above. In these embodiments, the stain may be, for example, phalloidin, gadodiamide, acridine orange, bismarck brown, barmine, Coomassie blue, bresyl violet, brystal violet, DAPI, hematoxylin, eosin, ethidium bromide, acid fuchsine, haematoxylin, hoechst stains, iodine, malachite green, methyl green, methylene blue, neutral red, Nile blue, Nile red, osmium tetroxide (formal name: osmium tetraoxide), rhodamine, safranin, phosphotungstic acid, osmium tetroxide, ruthenium tetroxide, ammonium molybdate, cadmium iodide, carbohydrazide, ferric chloride, hexamine, indium trichloride, lanthanum nitrate, lead acetate, lead citrate, lead(II) nitrate, periodic acid, phosphomolybdic acid, potassium ferricyanide, potassium ferrocyanide, ruthenium red, silver nitrate, silver proteinate, sodium chloroaurate, thallium nitrate, thiosemicarbazide, uranyl acetate, uranyl nitrate, vanadyl sulfate, or any derivative thereof. The stain may be specific for any feature of interest, such as a protein or class of proteins, phospholipids, DNA (e.g., dsDNA, ssDNA), RNA, an organelle (e.g., cell membrane, mitochondria, endoplasmic recticulum, golgi body, nuclear envelope, and so forth), or a compartment of the cell (e.g., cytosol, nuclear fraction, and so forth). The stain may enhance contrast or imaging of intracellular or extracellular structures. In some embodiments, the sample may be stained with haematoxylin and eosin (H&E).

Multiplexing the Methods

In some cases, the method disclosed herein can be used to analyze multiple target binding sites, for example, multiple RNAs, proteins or multiple molecular interactions. In such embodiments, multiple binding agents are conjugated with oligonucleotides having specific barcodes. Depending upon the distribution of the multiple binding targets, different binding agents having oligonucleotides with specific barcodes bring together other binding agents having oligonucleotides with other specific barcodes.

Production and detection of a nucleic acid reaction product that contains a combination of two specific barcodes in a specific position on a support indicates that the binding sites for the binding agents having the two specific barcodes are located in the corresponding position in the planar biological sample.

In some embodiments, the proximity assay may be done using multiple pairs of binding agent-oligonucleotide conjugates (e.g., at least 4, at least 10 or at least 50 pairs). The proximity assay can be designed so that each conjugate can produce reaction products with one other conjugate, with some but not all multiple conjugates or with all other conjugates. For example a ligation splint can be designed to join a specific pair of 3' and 5'binding agents, for example to interrogate a specific protein or interaction, a specific set of 3' and 5'binding agents, for example to interrogate a protein complex with several components, or one 3' binding agent can be designed to have the possibility to react with all 5'binding agents to interrogate the possible interactions with a large set or proteins or use the protein as a subcellular localization marker for other proteins.

In a multiplex analysis of a planar biological sample multiple binding agents can be designed that bind to multiple sites, including proteins, carbohydrates, DNA, RNA, and lipids. Thus, a multiple analysis according to the method disclosed herein can be used to simultaneously detect multiple proteins, carbohydrates, DNA, RNA, lipids, or any combination of these biomolecules.

Additional Aspects

In designing different details of the methods disclosed herein, for example, the sequences of oligonucleotides or the specific fluorescent labels used, certain aspects can be considered and are discussed below.

The sequences of the oligonucleotides that are linked to the binding agents may be selected so that they are "orthogonal," i.e., so that they do not cross-hybridize to one another. In addition, the sequences of the oligonucleotides should be designed to minimize binding to other nucleic acids endogenous to the sample (e.g., RNA or DNA).

In some embodiments, the oligonucleotides used in the method may be, independently, 8 nucleotides in length to as long as 150 nucleotides in length (e.g., in the range of 8 to 100 nucleotides in length). However, in many embodiments the oligonucleotides are 8 to 50 nucleotides in length, e.g., 10 to 30 nucleotides or 11 to 25 nucleotides in length although oligonucleotides having a length outside of these ranges can be used in many cases.

In some embodiments, an oligonucleotide may have a calculated $T_m$ in the range of 15° C. to 70° C. (e.g., 20° C.-60° C. or 35° C.-50° C.).

Oligonucleotides may be linked to binding agents using any convenient method (see, e.g., Gong et al., Bioconjugate Chem. 2016 27: 217-225 and Kazane et al. Proc Natl Acad Sci 2012 109: 3731-3736). For example, the unique oligonucleotides may be linked to the binding agents directly using any suitable chemical moiety on the binding agents (e.g., a cysteine residue or via an engineered site). In some embodiments, an oligonucleotide may be linked to the binding agents directly or indirectly via a non-covalent interaction. In some embodiments, the binding agents may be linked to their respective oligonucleotides by reacting an oligonucleotide-maleimide conjugate with the binding agent, thereby joining those molecules together.

In some embodiments, the method may comprise labeling the sample with the plurality of binding agents. This step may involve contacting the sample (e.g., an FFPE section mounted on a planar support such as a microscope slide) with all of the binding agents, en masse under conditions by which the binding agents bind to complementary sites (e.g., protein epitopes or nucleotide sequences) in the sample. Methods for binding antibodies and aptamers to complementary sites in the sample and methods for hybridizing nucleic acids probes to a sample in situ are well known. In some embodiments, the binding agents may be cross-linked to the sample, thereby preventing the binding agents from disassociating during subsequent steps. This crosslinking step may be done using any amine-to-amine crosslinker although a variety of other chemistries can be used to cross-link the binding agents to the sample if desired. In some embodiments, the binding agents are not cross-linked to the sample.

In certain embodiments, the reading is done by fluorescence-based imaging (FBI). Fluorophores of interest include but are not limited to xanthene dyes, e.g., fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4', 5'-dichloro-2', 7-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$) and rhodamine 110; cyanine dyes, e.g., Cy3, Cy5 and Cy7 dyes; coumarins, e.g., umbelliferone; benzimide dyes, e.g. Hoechst 33258; phenanthridine dyes, e.g., Texas Red; ethidium dyes; acridine dyes; carbazole dyes; phenoxazine dyes; porphyrin dyes; polymethine dyes, e.g., BODIPY dyes and quinoline dyes.

In some embodiments, the reading is done by FBI to detect samples labeled with two, three, or four distinguishable fluorophores and the method comprises repeating the hybridization, and detection steps multiple times (at least one or twice, up to the number of distinguishable fluorophores), each time using different bridging oligonucleotides and detection probes directed to different barcodes, prior to reading the sample by fluorescence microscopy to produce an image showing the locations of different nucleic acid product molecules on the support.

In some embodiments, repeated labeling cycles are performed. Particularly, up to four to five fluorophores are used in each labeling cycle and several labeling cycles are run. Each nucleic acid reaction product on the support can be labelled with one label in each cycle. Alternatively, each nucleic acid reaction product can be labelled with several fluorescent labels in the same cycle. Such combinatorial labeling would decode more barcodes per cycle and would reduce time for imaging.

In a further embodiment, each nucleic acid reaction product can be labelled with specific a ratio of the fluorescent labels. For example, depending on the barcode combinations present in the nucleic acid reaction products and fluorescently labeled probes directed to the different combination of the barcodes, the nucleic acid reaction products can be labelled such that any nucleic acid reaction products can be labelled with 100% of a first fluorescent but only 50% of a second fluorescent, while other nucleic acid reaction products can be labeled with has 50% of the first fluorescent but and 100% of the second fluorescent. This increases the number of distinguishable molecules detected in each cycle with a set number of spectrally resolvable dyes.

In some embodiments, the oligonucleotides and the binding agents are connected via a cleavable linker. In some cases, the cleavable linker is capable of being selectively cleaved using a stimulus (e.g., a chemical, light, or a change in its environment) without breaking any bonds in the oligonucleotides. The cleavable linker facilitates the transfer of the nucleic acid reactions products on to the support by freeing the nucleic acids from the binding agents and, consequently, freeing the nucleic acids from the targets to which the binding agents are specifically bound. Thus, in certain embodiments, the methods disclosed herein comprise a step of cleaving the linkers between the oligonucleotides and the binding agents after step (a) of performing a proximity assay on one or more pairs of binding agents that are bound to the sample, in situ, to produce nucleic acid reaction products and before step (b) of transferring the nucleic acid reaction products onto a support in a way that preserves the spatial relationship of the nucleic acid reaction products in the sample.

In some embodiments the cleavable linker may be an enzymatic reaction that allows breakage or release of a nucleic acid component from the binding agents. Suitable cleavable bonds that may be employed include, but are not limited to, the following: restriction enzyme digestion, specific site degradation using Uracil DNA Glycosylase followed by an endonuclease or treatment by acidic or basic conditions.

In some embodiments, the cleavable linkage may be a disulfide bond, which can be readily broken using a reducing agent (e.g., β-mercaptoethanol, TCEP or the like). Suitable cleavable bonds that may be employed include, but are not limited to, the following: base-cleavable sites such as esters, particularly succinates (cleavable by, for example, ammonia or trimethylamine), quaternary ammonium salts (cleavable by, for example, diisopropylamine) and urethanes (cleavable by aqueous sodium hydroxide); acid-cleavable sites such as benzyl alcohol derivatives (cleavable using trifluoroacetic acid), teicoplanin aglycone (cleavable by trifluoroacetic acid followed by base), acetals and thioacetals (also cleavable by trifluoroacetic acid), thioethers (cleavable, for example, by HF or cresol) and sulfonyls (cleavable by trifluoromethane sulfonic acid, trifluoroacetic acid, thioanisole, or the like); nucleophile-cleavable sites such as phthalamide (cleavable by substituted hydrazines), esters (cleavable by, for example, aluminum trichloride); and Weinreb amide (cleavable by lithium aluminum hydride); and other types of chemically cleavable sites, including phosphorothioate (cleavable by silver or mercuric ions) and diisopropyl-dialkoxysilyl (cleavable by fluoride ions). Other cleavable bonds will be apparent to those skilled in the art or are described in the pertinent literature and texts (e.g., Brown (1997) Contemporary Organic Synthesis 4(3); 216-237). In some embodiments, a cleavable bond may be cleaved by an enzyme. In particular embodiments, a photocleavable ("PC") linker (e.g., a uv-cleavable linker) may be employed. Suitable photocleavable linkers for use may include ortho-nitrobenzyl-based linkers, phenacyl linkers, alkoxybenzoin linkers, chromium arene complex linkers, NpSSMpact linkers and pivaloylglycol linkers, as described in Guillier et al. (Chem Rev. 2000 Jun. 14; 100(6):2091-158). Exemplary linking groups that may be employed in the subject methods may be described in Guillier et al., supra and Olejnik et al. (Methods in Enzymology 1998 291:135-154), and further described in U.S.P.N. 6,027,890; Olejnik et al. (Proc. Natl. Acad Sci, 92:7590-94); Ogata et al. (Anal. Chem. 2002 74:4702-4708); Bai et al. (Nucl. Acids Res. 2004 32:535-541); Zhao et al. (Anal. Chem. 2002 74:4259-4268); and Sanford et al. (Chem Mater. 1998 10:1510-20), and are purchasable from Ambergen (Boston, MA; NHS-PC-LC-Biotin), Link Technologies (Bellshill, Scotland), Fisher Scientific (Pittsburgh, PA) and Calbiochem-Novabiochem Corp. (La Jolla, CA).

In some embodiments, the cleavable linker comprises a linkage cleavable by a reducing agent (e.g., a disulfide bond). In these embodiments, the label may be removed using a reducing agent, e.g., tris(2-carboxyethyl)phosphine (TCEP).

In embodiments in which the sample is read by fluorescence, each reading step may produce an image of the nucleic acid product molecules distributed over the support. In some embodiments, the method may further comprise analyzing, comparing or overlaying, at least two of the images. In some embodiments, the method may further comprise overlaying all of the images to produce an image showing the pattern of distribution of different nucleic acid product molecules on the support. The image analysis module used may transform the signals from each fluorophore to produce a plurality of false color images. The image analysis module may overlay the plurality of false color images (e.g., superimposing the false colors at each pixel) to obtain a multiplexed false color image. Multiple images (e.g., unweighted, or weighted) may be transformed into a single false color, e.g., so as to represent a biological feature of interest characterized by the binding of specific binding agent. False colors may be assigned to specific binding agents or combinations of binding agents, based on manual input from the user. In certain aspects, the image may comprise false colors relating only to the intensities of labels associated with a feature of interest, such as in the nuclear compartment. The image analysis module may further be configured to adjust (e.g., normalize) the intensity and/or contrast of signal intensities or false colors, to perform a deconvolution operation (such as blurring or sharpening of the intensities or false colors), or perform any other suitable operations to enhance the image. The image analysis module may perform any of the above operations to align pixels obtained from successive images and/or to blur or smooth intensities or false colors across pixels obtained from successive images.

In some cases, the nucleic acid reaction products are transferred into a three-dimensional (3-D) gel matrix. The gel can be selected such that it would only immobilize the nucleic acid reaction products bound in the tissue but would not immobilize other biomolecules from the biological specimen. An example of such gel matrix includes polyacrylamide gel and silica gel. Proteins, RNA, DNA, and unligated oligonucleotides, and other biomolecules can be digested thereby leaving only the nucleic acid reaction products in the gel. The nucleic acid reaction products can be protected from the enzymatic digestion using exonuclease protection modifications. Thus, upon digestion of the other biomolecules, only the nucleic acid reaction products would be left in the gel. The nucleic acid reaction products can also be equipped with functions that cross link them to the 3D gel matrix thereby immobilizing them spatially in the gel for subsequent analysis when the gel has been cleared of other molecules.

Alternative In Situ Embodiments

In some embodiments, the proximity assay reaction products may remain in the tissue at the site at which they were made. In these embodiments, the proximity assay reaction products may be detected in situ using programmable hybridization.

In situ proximity assays have conventionally involved RCA (rolling circle amplification) and then detecting the RCA products in situ, e.g., by hybridization to a labeled probe that hybridizes to the RCA products. However, as noted above, RCA products are relatively large molecules and need physical space to be produced efficiently. In many cases, RCA products are inconsistently produced, both in terms of their density and length. As a result, in any one experiment, some RCA products can be densely packed, while others can be loosely packed. Likewise, some RCA products may occupy a large physical space while others may occupy a minute space. These problems often confound results.

In in situ embodiments of the present method, the "spots" that are observed after the proximity assay reaction products are labeled should be bright, consistently sized and have a consistent intensity. Moreover, since the spots are much smaller than those that would be obtained by RCA-based methods, many more spots can be observed. In addition, the present method allows the method to be multiplexed in a way that would be impossible using RCA-based methods. Some of the same advantages may be applicable to embodiments in which the proximity assay reaction products are transferred to a support, as described above.

Filter Embodiments

In any embodiment, a planar sample may be produced by passing a suspension of cells through a filter, wherein the cells are retained on the filter. A method for analyzing a suspension of cells is provided. In some embodiments, the method may comprise: (a) filtering a suspension of cells through a porous capillary membrane, thereby distributing the cells on the membrane, (b) placing the membrane on a planar support with the cell side of the membrane facing the support, (c) transferring nucleic acids from the cells into or onto the support in a way that preserves the spatial relationship of the nucleic acid in the cells, (d) removing the porous capillary membrane and cells from the support, and (e) spatially analyzing the nucleic acids transferred to support.

Figure 14:
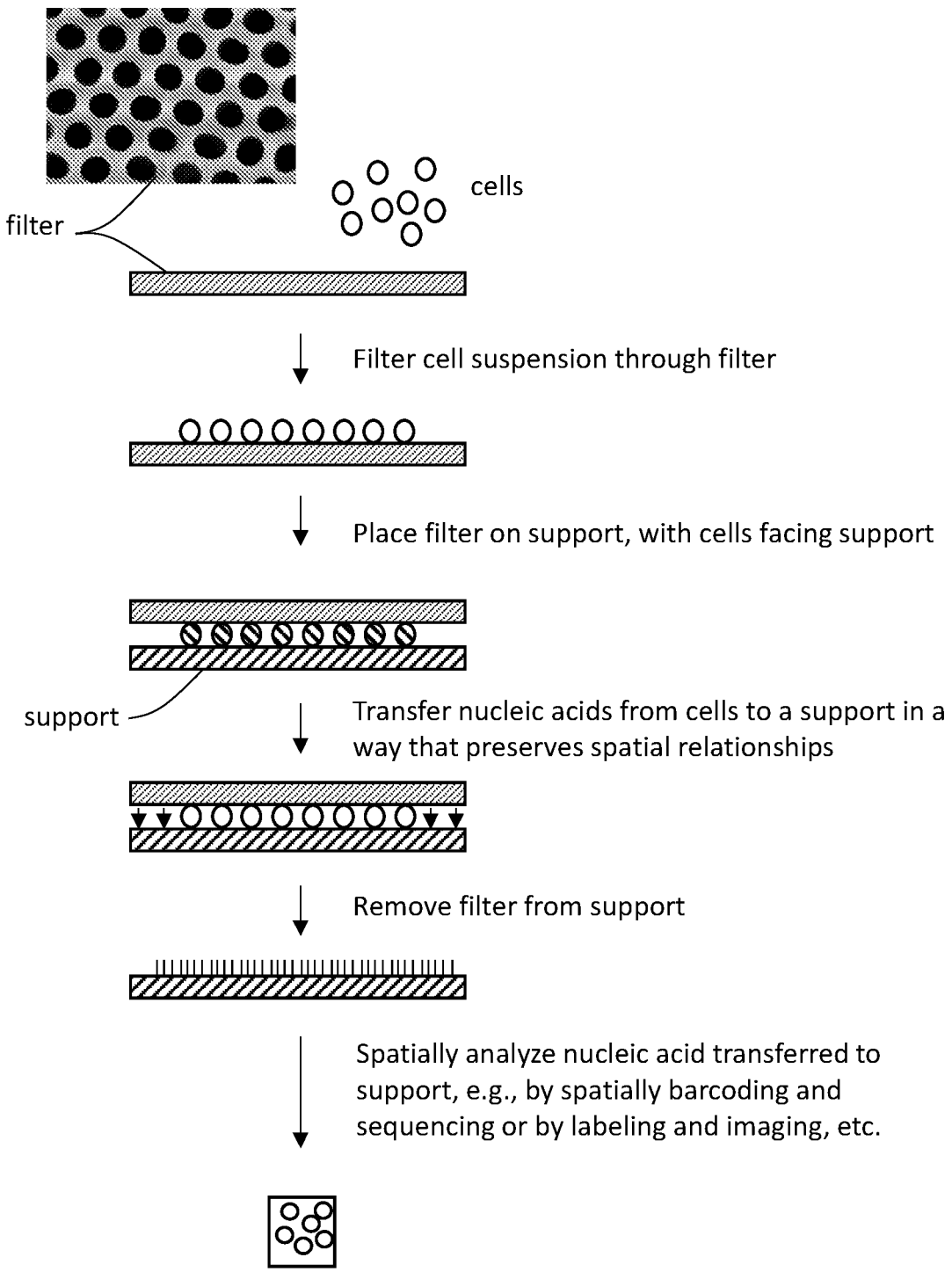
FIG. 14 schematically illustrates some of the principles of a method that uses a filter to collect the cells.
Figure 15:
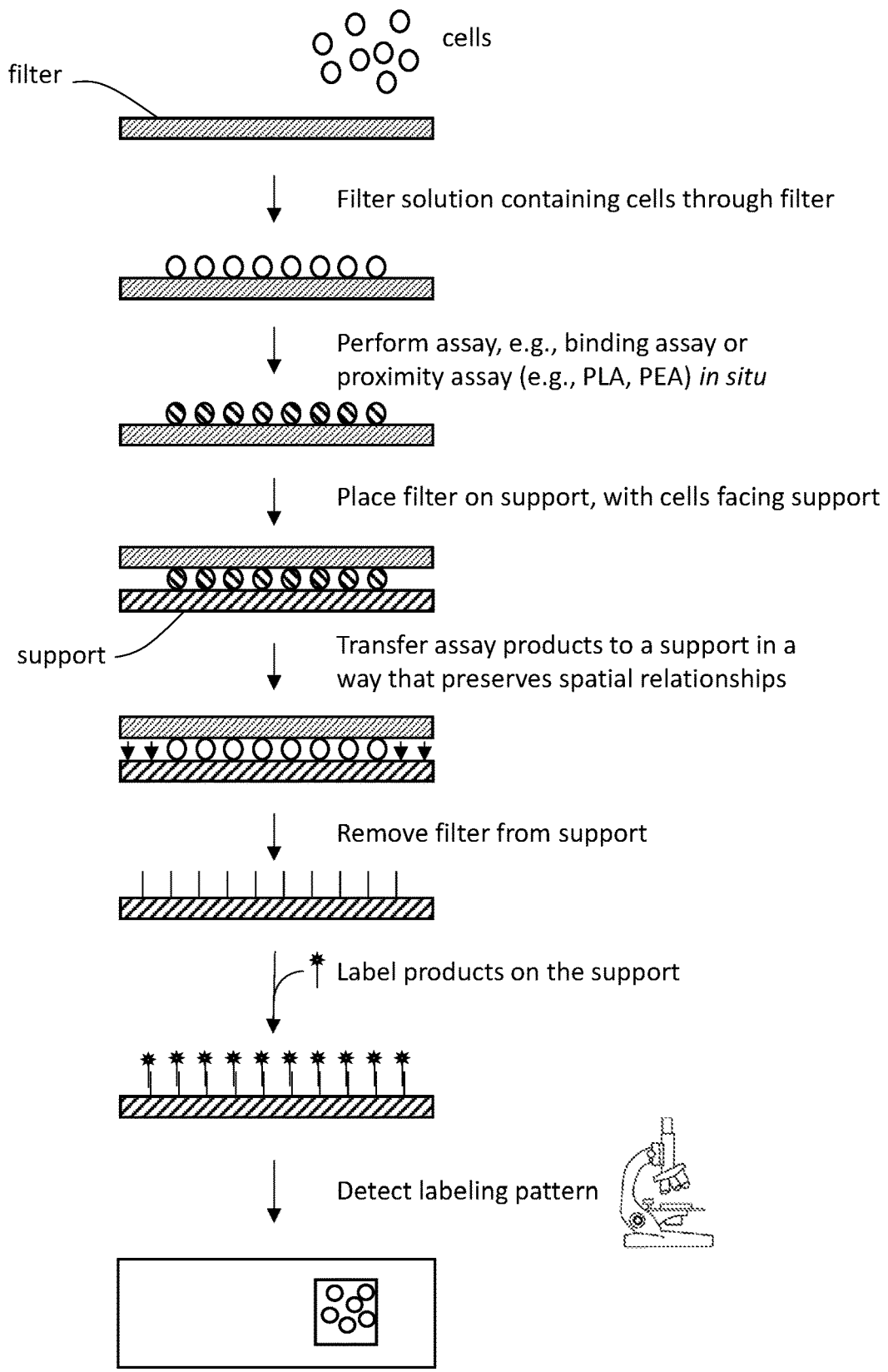
FIG. 15 schematically illustrates an embodiment of the method illustrated in FIG. 14.

As noted above, provided herein, among other things, is a method for analyzing a suspension of cells that may comprise: (a) filtering a suspension of cells through a porous capillary membrane, thereby distributing the cells on the membrane; (b) placing the membrane on a planar support with the cell side of the membrane facing the support; (c) transferring nucleic acids from the cells into or onto the support in a way that preserves the spatial relationship of the nucleic acid in the cells; (d) removing the porous capillary membrane and cells from the support; and (e) spatially analyzing the nucleic acids transferred to support. Some principles of this method are shown in FIG. 14.

In some embodiments, the method may further comprise, prior to step (c), e.g., between steps (a) and (c), performing a proximity assay on one or more pairs of binding agent-oligonucleotide conjugates that are bound to the cells, in situ, to produce proximity assay reaction products in or on the cells. Some principles of this embodiment are schematically illustrated in FIG. 14. In these embodiments, the nucleic acids transferred in step (c) and analyzed in step (e) comprise the proximity assay reaction products. In these embodiments, the analysis step may comprise (i) labeling the transferred proximity assay reaction products in or on the support; and (ii) imaging the support to produce an image of the sites to which the proximity assay reaction products are bound to in or on the support. A proximity assay comprises any combination of a ligation, a primer extension, and a gap-fill/ligation reaction involving the oligonucleotides of the binding agent-oligonucleotide conjugates. Examples of such assays are described in other places in this disclosure.

In some cases, RNA can be transferred from the cells onto the substrate. In some embodiments, the support may be coated in oligod(T), which hybridizes to polyA$^+$ RNA. In other embodiments, the planar support of (b) may comprise an array of spatially barcoded capture oligonucleotides, step (c) comprises hybridizing the transferred nucleic acids to the spatially barcoded capture oligonucleotides, and step (e) comprises extending the capture oligonucleotides using the transferred nucleic acids as a template and sequencing copies of the primer extension templates to produce sequence reads. See, e.g., Nerurkar et al (Cancers (Basel). 2020 12:2572) for a description of some aspects of this method. In these embodiments, the method may comprise mapping the sequence reads to site on the support using the spatial barcodes in the sequence reads.

The transferring step (c) may be done by electrophoresis or diffusion. In any embodiment, the porous capillary membrane may a porous anodic aluminum oxide (AAO) membrane although, other filters are known and could be used.

In any embodiment, the method may comprise (i) placing the suspension of cells on the porous capillary membrane; and (ii) applying a force that moves the liquid component of the suspension through the membrane. In these embodiments, the force may an active force selected from centrifugal force, negative pressure and positive pressure or a passive force selected from capillary action and evaporation, for example.

As noted above, the filter may be coated in a way that allows the cells to adhere to it, e.g., via electrostatic interactions. In some embodiments, the method may comprise washing the porous capillary membrane, as needed, to remove left-over reactants, etc., e.g., between steps (d) and (e).

In any embodiment, the interior diameter of the pores in the membrane is in the range of 2 nm to 500 nm, the average distance between the centers of adjacent pores in the membrane is in the range of 50 nm to 1000 nm, and the average distance between the edges of adjacent pores in the membrane is in the range of 10 nm to 500 nm. These distances can be adjusted as needed.

In any embodiment, the suspension of cells may comprise blood cells, immune cells (e.g., immune cells isolated from blood), single cells that have been separated from one another by trypsin treatment, or a cells have been cultured as a suspension.

Conventional methods for adhering a suspension of cells onto a surface often include depositing the cells on the surface and waiting for the cells to diffuse or sink to the surface. These methods take significant time and not all of the cells make it to the surface. In addition, because the cells settle in pattern that is determined by poison distribution, the prior methods may result in a significant number of doublet and clumps which, in turn, can confuse the analysis. Use of a filter ensures that all cells make it to the surface in a very rapid manner. Moreover, because the cells will travel with direction of flow of the liquid, the cells should be spread out more evenly (e.g., next to each other, rather than on top of one another) than other methods.

The method finds use in transferring RNA from the cell to a support (e.g., a surface coated in oligod(T) or a spatially barcoded array of oligonucleotides) and in transferring proximity assay products to a support, e.g., a glass slide, so that the products can be labeled and then analyzed on the support. In some embodiments, the method may comprise performing a proximity assay on one or more pairs of binding agent-oligonucleotide conjugates that are bound to the cells, in situ, to produce proximity assay reaction products in or on the cells, and transferring the proximity assay reaction products to the support. As will be described in greater detail below, the proximity assay reaction products transferred to the support can be produced in a variety of different ways, e.g., by performing a ligation, primer extension, gap-fill/ligation or any hybrid thereof between the oligonucleotides of the binding agent-oligonucleotide conjugates such that the sequence of one of the oligonucleotides becomes covalently joined to another oligonucleotide or copy of the same, and then transferring the first product to the support. Alternatively, the first products or unligated oligonucleotides can serve as a splint for ligating other oligonucleotides together to produce second products. In these embodiments, the second products may be transferred to the support.

In some cases, multiples samples may be "hash-tagged" prior to mixing and analysis (see, e.g., Stoeckius etc. Genome Biology 2018 19: 224). In these embodiments, the cells may be mixed with a sample barcoding affinity reagent (e.g., a barcoded antibody), which allows samples to be multiplexed.

In passing the cells through the filter, the cells become more separated from another on the solid phase as opposed to methods that may rely on random distribution. This, in turn, makes many of the downstream steps work more efficiently and allows more meaningful data to be gathered. As would be apparent from the discussion that follows below, the cells may be immobilized on the filter, and the cells may be fixed and permeabilized while they are on the filter. The structure of the filter can vary greatly. However, in many cases, the filter may have elements (mediated by physical structure, e.g., pores, or another surface chemistry) that causes the cells to self-assemble into an ordered pattern, thereby maximizing the use of the surface area.

In some embodiments, capture agents that are linked to barcoded oligonucleotide (e.g., binding agent-oligonucleotide conjugates, where the oligonucleotides have a barcode that identifies the antigen to which the antibody that it is conjugated to) may be introduced into or onto the cells. The probes bind to specific molecules, e.g., DNA, RNA or proteins. After removing unreacted probes (using for example washing or enzymatic degradation, etc.) the binding events can then be converted into reporter molecules that can be transferred (or "blotted") to another surface. In these embodiments, the reporters are transferred from the cells the surface of a support (e.g., a slide) in a way that preserves the relative spatial position of the molecules. The reporters are become attached to the support and can be detected on the support using optical single molecule resolution. Multiplexed analysis may be done using cyclic decoding if the samples are hash-tagged, the sample from which a cell derives can be determined by analysis of the sample barcode added prior to pooling.

The present method allows one to analyze cells a highly multiplexed way. The filtering step provides high yield in the number of available cells that are actually analyzed. Using single molecule combinatorial readout on the surface can potentially avoid the use a next generation sequencing instrument for data generation thereby reducing cost of analysis and providing high spatial resolution. As noted above, hash-tagging allows many samples can be analyzed in parallel and sample identity decoded during analysis.

One advantage of the present method is that it is challenging to interrogate cell optically on the surface of a filter. Moreover immobilizing cells on a non-porous surface can be quite slow and inefficient.

As will be described in greater detail below, the method may involve performing a proximity assay on one or more pairs of binding agent-oligonucleotide conjugates that are bound to the cells, in situ, to produce proximity assay reaction products in or on the cells, and then transferring proximity assay reaction products so the support. In these embodiments, the binding agent-oligonucleotide conjugates each comprise: i. a binding agent that binds to a site or sequence in the sample and ii. a first oligonucleotide. In some cases, the proximity assay may comprise joining pairs of reporter oligonucleotides together, in situ, to produce a reporter probe, wherein the joining of the reporter oligonucleotides is templated by either i. first oligonucleotides that are proximal to one another or ii. a ligation product of the same. The reporter probes are then transferred to the support where they are then detected.

In some embodiments, a proximity assay may be a ligation-based assay for analyzing DNA or RNA, or a ligation-based proximity assay for analyzing protein, protein-protein interactions or protein modifications. In some cases, the method may generate a biotinylated reporter molecule that is protected from exonuclease degradation by ligation of two molecules that are protected in the ends not participating in the ligation reaction.

In some embodiments, RNA molecules may be transferred and captured on a receiving surface using e.g., oligod (T) capture oligonucleotides. The captured RNA molecules can be subsequently covalently immobilized to the substrate and interrogated on the substrate using a probe-based approach (e.g., using single molecule FISH or padlock-probe/RCA based approached).

In some embodiments, antibody-oligonucleotide conjugates can be used to interrogate the presence of a protein in or on the cells. In these embodiments, the oligonucleotides could be released after the antibody has been bound to the cells and washed. In these embodiments, the released oligonucleotides can be designed to have e.g., biotin to facilitate capture on the receiving surface. Hybridization probes for RNA and DNA analysis can be used that wholly or partially are released during blotting and captured on the receiving surface using for example a biotin moiety and a streptavidin coated capture surface.

The filter could be anodic aluminum oxide (AAO) filter, or any filter that would allow capture of cells and subsequent blotting of biomolecules from the cells. Such filters may have micro or nanostructured permeable surfaces that have structures that direct the cells to distinct positions on the filter, using flow, so that the cells sit over and potentially block pores and thereby inhibit other cells to locate to the same compartment. In some embodiments, the surfaces can be used that are modified to that attract or repel cells to specific positions. In some cases, the overflow/excess cells can be washed away from the surface once cells are immobilized.

The method finds particular use in the analysis of peripheral blood cells and immune cells in the blood. Blood cells can be enriched for certain sub types to target analysis to certain cell types of interest. Blood cells can be interrogated for, e.g., surface receptors, secreted factors or receptor affinity to antigens to elucidate immune responses, analysis of pathway activation status using antibodies labeled with nucleic acids, etc. The method can also be used to analyze cells cultures in a multiplexed way, e.g., to perform analysis of CRISPR screening using expressed barcodes associated the CRISPR inserts in combination with analyzing effects on gene expression, protein expression and protein interactions and modifications. The method can also be used to analyze dissociated cells obtained from a tissue, in multiplex.

In some cases, cells can advantageously be fixed using, e.g., PFA before filtering and permeabilized in order to enable analysis of intracellular RNAs and or proteins.

A proximity assay method may comprise binding the cells with a plurality of binding agent-oligonucleotide conjugates and performing a proximity assay on the bound conjugates, in situ. The binding can be done before or after the cells are distributed on the filter. the binding agent part of the conjugates may be an antibody. However, in other embodiments, the binding agent may be an aptamer or oligonucleotide probe. The proximity assay may be done using a variety of different methods, e.g., a proximity ligation assay (which results in a first product in which the ends of the oligonucleotides in conjugates that are bind to sites that are proximal become ligated together) or a proximity extension assay (which results in a first product in which one or both oligonucleotides is/are extended using the other as a template). In either case, the first products can be released from the binding agents to which they are tethered and then transferred as the proximity assay reaction products to the support in step (c). In these embodiments, the proximity assay reaction products transferred to the support in step (c) are the first products. In other cases, the first product may be used as splint to ligate a pair of tailed detection oligonucleotides together to make second products. In these embodiments, the proximity assay reaction products transferred to the support in step (c) are the second products. The proximity assay reaction products may transferred to the support in a way that preserves their spatial relationships in the x-y plane, and then the filter (and cells attached thereto) is removed from the support. In this method, the transferred nucleic acids become tethered to the support and then can be detected on the support, e.g., by hybridizing labeled probes to the tethered proximity assay reaction products (directly or indirectly) while they are on the support, and analyzing the labelling pattern by microscopy. The support may be a planar substrate such as a slide (which may be coated), or a three-dimensional substrate such as a gel. If the substrate is a planar substrate, then the proximity assay reaction products will be on the substrate. If the substrate is a three-dimensional substrate, then the proximity assay reaction products will be in the substrate.

The present method can be implemented using any type of capture support that can act as a filter for cells. Such a filter should have a pore size sufficient to allow rapid fluid flow-through of liquid and capture the cells. Suitable capture supports may be made from porous organic or inorganic materials including solids such as porous metals, ceramics, homogeneous films (e.g., polymers) and heterogeneous solids (polymeric mixes, mixed glasses). Porous ceramic membranes can be made from inorganic materials (such as alumina, titania, zirconia oxides, recrystallized silicon carbide). See, e.g., the PamChip sold by Pamgene (The Netherlands), Wu et al, Nucleic Acids Res. 2004 32: e123 and Anthony et al Biotechniques. (2003) 34:1082-6, 1088-9. Exemplary porous polymer membranes can be made from cellulose acetate, nitrocellulose, cellulose esters (CA, CN, and CE), polysulfone (PS), polyether sulfone (PES), polyacrilonitrile (PAN), polyamide, polyimide, polyethylene and polypropylene (PE and PP), polytetrafluoroethylene (PTFE), polyvinylidene fluoride (PVDF) and polyvinylchloride (PVC).

In any embodiment, the pores of the capillary membrane should be of sufficient size so as to prevent the cells from passing through the pores. For example, in embodiments, the pore diameter of the capillary membrane may be no more than 50% of the median diameter of the cells, while in some embodiments it may be no more than 10% of the median diameter of the cells. As such, in filtering the sample using the porous capillary membrane, cells should remain on top of the membrane and should not fully enter or pass through the pores.

In certain embodiments, the porous capillary membrane may comprise a coating that binds to the cells and/or a patterned surface (e.g., an array of hydrophilic or hydrophobic areas) that help separate the cells.

The interior diameter of the pores in the membrane, the distance between the centers of adjacent pores in the membrane, and the distance between the edges of adjacent pores in the membrane can be controlled by the voltage of the deposition, the type of acid, and other parameters (see, generally, Poinern, supra). In some embodiments, the interior diameter of the pores in the membrane may be in the range of 5 nm to 500 nm, e.g., 4 nm to 250 nm, 4 nm to 50 nm, 50 nm to 100 nm, 100 nm to 200 nm or 200 nm to 500 nm. Independently, the average distance between the centers of adjacent pores in the membrane may be in the range of 50 nm to 1000 nm, e.g., 50 nm to 420 nm, 50 nm to 100 nm, 100 nm to 250 nm, 250 nm to 500 nm or 500 nm to 1000 nm. The average distance between the edges of adjacent pores in the membrane may be in the range of 10 nm to 500 nm, 10 nm to 50 nm, 50 nm to 200 nm, or 200 nm to 500 nm. It may be understood that the diameter and average distance values between pores provided herein are exemplary, and such values may vary based on the embodiment. The membrane used may be of any suitable thickness, e.g., in the range of 20 μm to 500 μm or 50 μm to 200 μm, as desired and, as noted above, may contain one or more support structures (e.g., a support ring) in order to maintain the integrity of the membrane during use.

As noted above, the suspension of cells may comprises blood cells, immune cells, single cells that have been separated from one another by trypsin treatment, or a cells have been cultured as a suspension, etc. In these embodiments, the term "blood sample" or grammatical equivalents thereof refers to a sample of whole blood or a sub-population of cells in whole blood. Sub-populations of cells in whole blood include platelets, red blood cells (erythrocytes), platelets and white blood cells (i.e., peripheral blood leukocytes, which are made up of neutrophils, lymphocites, eosinophils, basophils and monocytes). These five types of while blood cells can be further divided into two groups, granulocytes (which are also known as polymorphonuclear leukeocytes and include neutrophils, eosinophils and basophils) and mononuclear leukocytes (which include monocytes and lymphocytes). Lymphocytes can be further divided into T cells, B cells and NK cells. Peripheral blood cells are found in the circulating pool of blood and not sequestered within the lymphatic system, spleen, liver, or bone marrow. If blood is first contacted with an agent and then a sample of the blood is used in an assay, then a portion or all of the contacted blood may be used in the assay. Blood is but one of many biological samples that can be employed in the method. In other embodiments, intact cells from other tissues (e.g., other soft tissues such as liver or spleen etc.) or cells grown in tissue culture may be employed. Methods for treating such tissues to provide a cell suspension suitable for flow cytometry are known. Once produced, a cell suspension may be employed in a similar way to that described below. A suspension of cells may be made from a soft tissue such as brain, adrenal gland, skin, lung, spleen, kidney, liver, spleen, lymph node, bone marrow, bladder stomach, small intestine, large intestine or muscle, etc., as well as a monolayer of cells.

In some embodiments, the cells may contacted with a test agent ex vivo (i.e., using blood drawn from a subject) or in vivo (e.g., by administering the test agent to a mammal), and the results from the assay may be compared to results obtained from a reference sample of cells (e.g., blood cells that have not been in contact with the test agent or with a different amount of the test agent).

The suspension applied to the filter may contain at least 1,000, at least $10^4$, at least $10^5$, at least $10^6$ cells.

In some cases, the method disclosed herein comprises removing the filter (and cells) from the support to leave the transferred nucleic acid on or in the support.

The filter can be removed from the support in any suitable manner. For example, the substrate, such as the glass slide on which the planar biological sample is placed can simply be moved away from the support. Because the nucleic acid reaction products are bound to the support, either covalently or non-covalently, the nucleic acid reaction products remain attached to the support while the filter is removed from the support.

Any remnants of the biological sample can be removed via enzymatic action. For example, the support can be treated with enzymes that degrade biomolecules other than polynucleotides thereby only removing the biomolecules other than the nucleic acids. Moreover, if the nucleic acid reaction products comprise DNA, the support can be treated with RNA degrading enzymes to remove contaminating RNAs. The support can be treated with a cocktail of exonucleases, for example.

Kits

Also provided by this disclosure are kits that contain reagents for practicing the subject method, as described above. These various components of a kit may be in separate vessels or mixed in the same vessel.

The various components of the kit may be present in separate containers or certain compatible components may be pre-combined into a single container, as desired.

In addition to the above-mentioned components, the subject kit may further include instructions for using the components of the kit to practice the subject method.

Utility

The methods and compositions described herein find general use in a wide variety of applications for analysis of planar biological samples (e.g., in the analysis of tissue sections, sheets of cells, or spun-down cells). The method may be used to analyze any tissue, including tissue that has been clarified, e.g., through lipid elimination, for example. The sample may be prepared using expansion microscopy methods (see, e.g., Chozinski et al. Nature Methods 2016 13: 485-488), which involves creating polymer replicas of a biological system created through selective co-polymerization of organic polymer and cell components. The method can be used to analyze spreads of cells, exosomes, extracellular structures, biomolecules deposited on a solid support or in a gel (Elisa, western blot, dot blot), whole organism, individual organs, tissues, cells, extracellular components, organelles, cellular components, chromatin and epigenetic markers, biomolecules and biomolecular complexes, for example. The binding agents may bind to any type of molecule, including proteins, lipids, polysaccharides, proteoglycans, metabolites, nucleic acid, or artificial small molecules or the like. The method may have many biomedical applications in screening and drug discovery and the like. Further, the method has a variety of clinical applications, including, but not limited to, diagnostics, prognostics, disease stratification, personalized medicine, clinical trials and drug accompanying tests.

The field of spatial analysis technology, the disclosure aims to provide highly multiplex readout of protein-protein interactions and protein modifications in situ. The disclosure also allows single molecule analysis of proteins, protein post-translational modifications, and protein interactions.

The methods disclosed herein could also be used to analyze RNAs or RNA interactions between RNAs and other molecules, such as proteins, in a single assay format.

In some cases, the methods disclosed herein could be used to analyze target RNAs. For example, as discussed above, an RNA target from a planar biological sample can be directly copied into a reporter polynucleotide using reporter probes. Particularly, a proximity assay is not performed to produce a nucleic acid reaction product, but the RNA target is used as a template to produce a reporter polynucleotide. Such step could for example be performed before contacting the sample with binding agents since antigen retrieval steps required for protein analysis may damage RNA but not DNA, or simultaneously with the introduction of detection oligonucleotides ligating to the first products generated by joining the nucleic acids of the binding agents.

Moreover, the methods disclosed herein could be used to analyze interactions of RNA with other biomolecules, such as RNA, protein, DNA, carbohydrates, lipids, etc. In certain such embodiments, proximity assay can be conducted using one binding agent targeting an RNA and another binding agent targeting a protein, carbohydrate, or lipid. Proximity assay can also be conducted using one binding agent targeting an RNA and another binding agent targeting a different RNA. Such embodiments can be used to analyze interaction of a target RNA to any other biomolecule for which there a specific binding agent is available.

In some cases, the method disclosed herein can be used to identify target sites that are located proximal to each other. For example, a first binding agent-oligonucleotide conjugate binds to a first site and a second binding agent-oligonucleotide conjugate binds to a second site. When the first site and the second site are proximal, the oligonucleotides are brought close to each other. Therefore, the production of a nucleic acid from the oligonucleotides conjugated to the first and the second binding agent-oligonucleotide conjugates indicates that the oligonucleotides are conjugated to binding agents that are bound to sites that are proximal.

Thus, in certain cases, the method disclosed herein can be used to: determine where specific protein proteins are located in a planar biological sample. In these embodiments, the binding agents bind to different sites on the same protein.

In some cases, the method disclosed herein can also be used to identify where protein-protein interactions occur. In these embodiments, the binding agents bind to different proteins.

Since the relative proximity of targets depend on the absolute concentration and the amount of signal generated from each interaction depend on additional efficiency factors like binding affinity and chemical and enzymatic efficiencies relating the relative signals within a multiplex experiment to each other will be advantageous. For example, using reference proteins, RNA or DNA targets or relating the signal from the single individual proteins to the signal from the interaction of the proteins. The signals can for example be analyzed per cell, among a group of cells, for a cell-type determined by the presence of cellular markers or by area.

Also, in some cases, the method disclosed herein can be used to determine post-translation modification of a biomolecule, such as a protein. In certain such embodiments, one binding agent binds to the post translational modification or to an epitope covering both the post translational modification and the target protein and the other binding agent binds to a different site in the same protein. The production of a nucleic acid from the oligonucleotides conjugated to the first and the second binding agent-oligonucleotide conjugates indicates that the protein has sites that are post-translationally modified. By using binding agents specific for general post translational modifications, the presence of such modifications across a large number of proteins can be interrogated. The signal can advantageously be analyzed in a relative manner to normalize away the effect of the global presence of modifications, the impact of protein concentrations and assay efficiencies.

In particular embodiments, the sample may be a section of a tissue biopsy obtained from a patient. Biopsies of interest include both tumor and non-neoplastic biopsies of skin (melanomas, carcinomas, etc.), soft tissue, bone, breast, colon, liver, kidney, adrenal, gastrointestinal, pancreatic, gall bladder, salivary gland, cervical, ovary, uterus, testis, prostate, lung, thymus, thyroid, parathyroid, pituitary (adenomas, etc.), brain, spinal cord, ocular, nerve, and skeletal muscle, etc.

In certain embodiments, binding agents specifically bind to biomarkers, including cancer biomarkers, that may be proteinaceous. Exemplary cancer biomarkers, include, but are not limited to carcinoembryonic antigen (for identification of adenocarcinomas), cytokeratins (for identification of carcinomas but may also be expressed in some sarcomas), CD15 and CD30 (for Hodgkin's disease), alpha fetoprotein (for yolk sac tumors and hepatocellular carcinoma), CD117 (for gastrointestinal stromal tumors), CD10 (for renal cell carcinoma and acute lymphoblastic leukemia), prostate specific antigen (for prostate cancer), estrogens and progesterone (for tumor identification), CD20 (for identification of B-cell lymphomas) and CD3 (for identification of T-cell lymphomas).

different marker. Examples of cancers, and biomarkers that can be used to identify those cancers, are shown below. In these embodiments, one does not need to examine all of the markers listed below to make a diagnosis.

| | |
|---|---|
| Acute Leukemia IHC Panel | CD3, CD7, CD20, CD34, CD45, CD56, CD117, MPO, PAX-5, and TdT. |
| Adenocarcinoma vs. Mesothelioma IHC Panel | Pan-CK, CEA, MOC-31, BerEP4, TTF1, calretinin, and WT-1. |
| Bladder vs. Prostate Carcinoma IHC Panel | CK7, CK20, PSA, CK 903, and p63. |
| Breast IHC Panel | ER, PR, Ki-67, and HER2. Reflex to HER2 FISH after HER2 IHC is available. |
| Burkitt vs. DLBC Lymphoma IHC panel | BCL-2, c-MYC, Ki-67. |
| Carcinoma Unknown Primary Site, Female (CUPS IHC Panel - Female) | CK7, CK20, mammaglobin, ER, TTF1, CEA, CA19-9, S100, synaptophysin, and WT-1. |
| Carcinoma Unknown Primary Site, Male (CUPS IHC Panel - Male) | CK7, CK20, TTF1, PSA, CEA, CA19-9, S100, and synaptophysin. |
| GIST IHC Panel | CD117, DOG-1, CD34, and desmin. |
| Hepatoma/Cholangio vs. Metastatic Carcinoma IHC Panel | HSA (HepPar 1), CDX2, CK7, CK20, CAM 5.2, TTF-1, and CEA (polyclonal). |
| Hodgkin vs. NHL IHC Panel | BOB-1, BCL-6, CD3, CD10, CD15, CD20, CD30, CD45 LCA, CD79a, MUM1, OCT-2, PAX-5, and EBER ISH. |
| Lung Cancer IHC Panel | chromogranin A, synaptophysin, CK7, p63, and TTF-1. |
| Lung vs. Metastatic Breast Carcinoma IHC Panel | TTF1, mammaglobin, GCDFP-15 (BRST-2), and ER. |
| Lymphoma Phenotype IHC Panel | BCL-2, BCL-6, CD3, CD4, CD5, CD7, CD8, CD10, CD15, CD20, CD30, CD79a, CD138, cyclin D1, Ki67, MUM1, PAX-5, TdT, and EBER ISH. |
| Lymphoma vs. Carcinoma IHC Panel | CD30, CD45, CD68, CD117, pan-keratin, MPO, S100, and synaptophysin. |
| Lymphoma vs. Reactive Hyperplasia IHC Panel | BCL-2, BCL-6, CD3, CD5, CD10, CD20, CD23, CD43, cyclin D1, and Ki-67. |
| Melanoma vs. Squamous Cell Carcinoma IHC Panel | CD68, Factor XIIIa, CEA (polyclonal), S-100, melanoma cocktail (HMB-45, MART-1/Melan-A, tyrosinase) and Pan-CK. |
| Mismatch Repair Proteins IHC Panel (MMR/Colon Cancer) | MLH1, MSH2, MSH6, and PMS2. |
| Neuroendocrine Neoplasm IHC Panel | CD56, synaptophysin, chromogranin A, TTF-1, Pan-CK, and CEA (polyclonal). |
| Plasma Cell Neoplasm IHC Panel | CD19, CD20, CD38, CD43, CD56, CD79a, CD138, cyclin D1, EMA, IgG kappa, IgG lambda, and MUM1. |
| Prostate vs. Colon Carcinoma IHC Panel | CDX2, CK 20, CEA (monoclonal), CA19-9, PLAP, CK 7, and PSA. |
| Soft Tissue Tumor IHC Panel | Pan-CK, SMA, desmin, S100, CD34, vimentin, and CD68. |
| T-Cell Lymphoma IHC panel | ALK1, CD2, CD3, CD4, CD5, CD7, CD8, CD10, CD20, CD21, CD30, CD56, TdT, and EBER ISH. |
| T-LGL Leukemia IHC panel | CD3, CD8, granzyme B, and TIA-1. |
| Undifferentiated Tumor IHC Panel | Pan-CK, S100, CD45, and vimentin. |

The above-described method can be used to analyze cells from a subject to determine, for example, whether the cell is normal or not or to determine whether the cells are responding to a treatment. In one embodiment, the method may be employed to determine the degree of dysplasia in cancer cells. In these embodiments, the cells may be a sample from a multicellular organism. A biological sample may be isolated from an individual, e.g., from a soft tissue. In particular cases, the method may be used to distinguish different types of cancer cells in FFPE samples.

The method described above finds particular utility in examining samples using a plurality of antibodies or antibody pairs, each antibody or antibody pair recognizing a In some embodiments, the method may involve obtaining data (an image) as described above (an electronic form of which may have been forwarded from a remote location), and the image may be analyzed by a doctor or other medical professional to determine whether a patient has abnormal cells (e.g., cancerous cells) or which type of abnormal cells are present. The image may be used as a diagnostic to determine whether the subject has a disease or condition, e.g., a cancer. In certain embodiments, the method may be used to determine the stage of a cancer, to identify metastasized cells, or to monitor a patient's response to a treatment, for example.

Cells markers, including markers for T-cells, B-cells and neutrophiles (e.g., CD3, CD20, CD15, etc., can also be investigated. The compositions and methods described herein can be used to diagnose a patient with a disease. In some cases, the presence or absence of a biomarker in the patient's sample can indicate that the patient has a particular disease (e.g., a cancer). In some cases, a patient can be diagnosed with a disease by comparing a sample from the patient with a sample from a healthy control. In this example, a level of a biomarker, relative to the control, can be measured. A difference in the level of a biomarker in the patient's sample relative to the control can be indicative of disease. In some cases, one or more biomarkers are analyzed in order to diagnose a patient with a disease. The compositions and methods of the disclosure are particularly suited for identifying the presence or absence of, or determining expression levels, of a plurality of biomarkers in a sample.

In some cases, the compositions and methods herein can be used to determine a treatment plan for a patient. The presence or absence of a biomarker may indicate that a patient is responsive to or refractory to a particular therapy. For example, a presence or absence of one or more biomarkers may indicate that a disease is refractory to a specific therapy, and an alternative therapy can be administered. In some cases, a patient is currently receiving the therapy and the presence or absence of one or more biomarkers may indicate that the therapy is no longer effective.

In some cases, the method may be employed in a variety of diagnostic, drug discovery, and research applications that include, but are not limited to, diagnosis or monitoring of a disease or condition (where the image identifies a marker for the disease or condition), discovery of drug targets (where the a marker in the image may be targeted for drug therapy), drug screening (where the effects of a drug are monitored by a marker shown in the image), determining drug susceptibility (where drug susceptibility is associated with a marker) and basic research (where is it desirable to measure the differences between cells in a sample).

In certain embodiments, two different samples may be compared using the above methods. The different samples may be composed of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen, etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material contains cells that are susceptible to infection by a pathogen such as a virus, e.g., human immunodeficiency virus (HIV), etc., and the control material contains cells that are resistant to infection by the pathogen. In another embodiment, the sample pair is represented by undifferentiated cells, e.g., stem cells, and differentiated cells.

The images produced by the method may be viewed side-by-side or, in some embodiments, the images may be superimposed or combined. In some cases, the images may be in color, where the colors used in the images may correspond to the labels used.

Cells from any organism, e.g., from bacteria, yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used.

EMBODIMENTS

Embodiment F1. A method for analyzing a sample, comprising:
  (a) contacting an oligonucleotide or a conjugate comprising the same with a planar biological sample under conditions by which the oligonucleotide or conjugate specifically binds to sites in or on the sample; (b) performing one or more steps to release and/or extend the oligonucleotide or complement thereof in situ, to produce a reporter probe; (c) transferring all or a part of the reporter probe from the sample to a planar support, that does not comprise an array of oligonucleotides, in a way that preserves the spatial relationship of the reporter probe in the sample; and (d) detecting the reporter probe on the support.

Embodiment F2. The method of embodiment F1, wherein:
  step (a) comprises hybridizing oligonucleotides with the sample under conditions by which the oligonucleotides hybridize to endogenous RNA or DNA in the sample; and
  step (b) comprises joining together any oligonucleotides that are hybridized to adjacent sites in the RNA or DNA via a ligation or gap-fill/ligation.

Embodiment F3. The method of embodiment F1, wherein the sample comprises ligation products from a proximity ligation assay; and
  step (a) comprises hybridizing oligonucleotides with the sample under conditions by which the oligonucleotides hybridize to the ligation products; and
  step (b) comprises joining together any oligonucleotides that are hybridized to adjacent sites in the ligation products via a ligation or gap-fill/ligation reaction.

Embodiment F4. The method of embodiment F1 or F2, wherein the oligonucleotides are exonuclease-sensitive, but the reporter probe is exonuclease-resistant.

Embodiment F5. The method of embodiment F4, wherein the method further comprises treating the sample with an exonuclease between steps (b) and (c).

Embodiment F6. The method of embodiment F1, wherein;
  step (a) comprises contacting the tissue sample with antibody-oligonucleotide conjugates with under conditions by which the antibodies bind to sites in or on the sample; and
  step (b) comprises cleaving the oligonucleotides or an extension product thereof from the conjugates antibodies to produce the reporter probe.

Embodiment F7. The method of embodiment F1, wherein the reporter probe is produced via a ligation or gap-fill reaction.

Embodiment F8. The method of embodiment F1, wherein the reporter probe is produced via primer extension reaction.

Embodiment F9. The method of any prior F embodiment, wherein step (d) is done by microscopy.

Embodiment F10. The method of embodiment F9, wherein step (d) comprises hybridizing a labeled probe to the reporter probe and then analyzing the binding pattern of the probe by microscopy.

Embodiment F11. The method of embodiment F10 where sets of probes are hybridized and washed away in repeated cycles to decode individual reporter molecules are decoded using at least two or more cycles.

Embodiment F12. The method of any prior F embodiment, wherein the sample is a tissue section Embodiment F13. The method of any prior F embodiment, wherein the sample comprises mammalian cells.

Embodiment F14. The method of any prior F embodiment, the releasing is done by contacting the biological sample with the support after step (a), with the biological sample faces the support and then heating the sample.

Embodiment A1. A method for analyzing a planar biological sample, comprising:
  (a) performing a proximity assay on one or more pairs of binding agent-oligonucleotide conjugates that are bound to the sample, in situ, to produce proximity assay reaction products;
  (b) transferring the nucleic acid reaction products into or onto a support in a way that preserves the spatial relationship of the proximity assay reaction products in the sample; and
  (c) detecting the proximity assay reaction products in or on the support.

Embodiment A2. The method of embodiment A1, wherein the proximity assay comprises any combination of a ligation, a primer extension, and a gap-fill/ligation reaction involving the oligonucleotides of the binding agent-oligonucleotide conjugates.

Embodiment A3. The method of embodiment A1, wherein the support is a planar support.

Embodiment A4. The method of embodiment A1, wherein the support is a matrix.

Embodiment A5. The method of embodiment A1, wherein the support is a gel.

Embodiment A6. The method of any preceding A embodiment, wherein step (c) comprises:
  (b) (i) labeling the proximity assay reaction products in or on the support; and
  (ii) imaging the support to produce an image of the sites to which the proximity assay reaction products are bound to in or on the support.

Embodiment A7. The method of any preceding A embodiment, wherein the transferring in step (b) is done by placing the sample on the support and transferring the proximity assay reaction products onto the surface of the support by electrophoresis or diffusion.

Embodiment A8. The method of any preceding A embodiment, wherein step (c) comprises: hybridizing one or more labeled oligonucleotides, directly or indirectly, to the nucleic acid reaction products.

Embodiment A9. The method of any preceding A embodiment, wherein in step (c) the proximity assay reaction products are detected by hybridization to a defined nucleic acid structure composed of a predetermined number of oligonucleotides and a predetermined number of labeled oligonucleotides.

Embodiment A10. The method of embodiment A9, wherein the structure is nucleated by at least two hybridization events to the proximity assay reaction products.

Embodiment A11. The method of embodiment A10, wherein the at least two hybridization events comprise a first hybridization to a first sequence in a proximity assay reaction product and a second hybridization to a second sequence in the proximity assay reaction product Embodiment A12. The method of any preceding A embodiment, wherein the method comprises comparing the image produced in step (a) with an image of the sample.

Embodiment A13. The method of embodiment A12, wherein the image of the sample is produced via staining the sample with a microscopy stain.

Embodiment A14. The method of any of the preceding A embodiments, further comprising removing the sample from the support between steps (b) and (c).

Embodiment A15. The method of any of the preceding A embodiments, wherein the biological sample is a tissue section.

Embodiment A16. The method of embodiment A15, wherein the tissue section is a formalin-fixed paraffin embedded (FFPE) tissue section.

Embodiment A17. The method of any preceding A embodiment, wherein the support is a glass slide.

Embodiment A18. The method of any preceding A embodiment, wherein the binding agents of step (a) are oligonucleotide probes, antibodies, or aptamers. Embodiment B1. A method for analyzing a biological sample, comprising:
  (a) hybridizing multiple pairs of reporter oligonucleotides to RNA in a biological sample, in situ;
  (b) ligating together any pairs of reporter oligonucleotides that are hybridized to sites that are adjacent to one another in situ, to produce ligation products;
  (c) transferring the ligation products into or onto a support in a way that preserves the spatial relationship of the ligation products in the sample; and
  (d) detecting the ligation products on the support by hybridization of a labeled probe to the ligation products.

Embodiment B2. The method of embodiment B1, wherein:
  one member of each pair of reporter oligonucleotides has an end that contains a reactive group and the other member has an exonuclease-resistant linkage;
  in step (c) the ligation products become tethered to the support via the reactive group; and,
  prior to step (d) the method comprises degrading any unligated reporter oligonucleotides and other single-stranded DNA molecules by exonuclease treatment.

Embodiment B3. The method of any prior B embodiment, wherein at least one member of each pair of reporter oligonucleotides has a tail that does not hybridize to the RNA and, in step (d), the labeled probe hybridizes with the tail of a reporter oligonucleotide in the ligation products.

Embodiment B4. The method of any prior B embodiment, wherein the biological sample is a tissue section.

Embodiment B5. The method of any prior B embodiment, wherein the labeled probe comprises a complex of a defined number of unlabeled and labeled oligonucleotides that are hybridized to one another.

Embodiment B6. The method of any prior B embodiment, wherein step (d) comprises:
  (b) (i) hybridizing the ligation products on the support with first and second bridging oligonucleotides, wherein the first and second bridging oligonucleotides hybridize to different sequences in the ligation products; and (ii) hybridizing the first and second bridging oligonucleotides that are hybridized to the ligation products with a labeled complex composed of a predetermined number of labeled and unlabeled oligonucleotides that are hybridized in a complex, wherein the labeled complex hybridizes to both bridging oligonucleotides; and (iii) detecting the hybridized labeled complex at a resolution that can detect hybridization of a single labeled complex.

In these embodiments, the first and second bridging oligonucleotides may hybridize in a "head-to-head" manner, where the 5' end of one of the bridging oligonucleotide is adjacent to (with a gap of less than 10, less than 5, or 4, 3, 2, 1 or 0 nucleotides) the 3' end of the other. Drawn out in the complex, these molecules are mirror images, not the same. The bridging molecules can have several binding sites for the labeling probes.

Embodiment B7. The method of embodiment B6, wherein
the first and second bridging oligonucleotides have tails that do not hybridize to the ligation products;
at least some of the unlabeled oligonucleotides in the labeled complex hybridize with the tails of both the first and second bridging oligonucleotides; and
the complex comprises a defined number of labeled oligonucleotides, wherein the labeled oligonucleotides are hybridized to the unlabeled oligonucleotides.

Embodiment B8. The method of any of embodiments B5-B7, wherein a complex comprises 4-20 unlabeled oligonucleotides and 8-200 labeled oligonucleotides.

Embodiment B9. The method of any of embodiments B6-B8, wherein the first bridging oligonucleotide has a first stabilization sequence and the second bridging oligonucleotide has a second stabilization sequence, and the first and second stabilization sequences hybridize to one another when the first and second bridging oligonucleotides are hybridized to a ligation product.

Embodiment B10. The method of embodiment B9, wherein the stabilization sequences are 4-10 bp in length, wherein one stabilization is at the 3' end of the first bridging oligonucleotide and the other stabilization sequence is at the 5' end of the second bridging oligonucleotide.

Embodiment C1. A method for analyzing a biological sample, comprising:
(a) labeling a biological sample with a plurality of conjugates that each comprise: i. a binding agent that binds to a site or sequence in the sample and ii. a first oligonucleotide;
(b) joining pairs of reporter oligonucleotides together, in situ, to produce a reporter probe, wherein the joining of the reporter oligonucleotides is templated by either i. first oligonucleotides that are proximal to one another or ii. a ligation product of the same;
(c) optionally transferring the reporter probe into or onto a support in a way that preserves the spatial relationship of the proximity assay reaction products in the biological sample;
(d) removing unreacted reporter oligonucleotides and other single-stranded DNA molecules by exonuclease treatment or by washing, wherein the removing is done in situ or in or on the support; and
(e) detecting the reporter probe, either in situ or in or on the support, by hybridization of a labeled probe to the reporter probe.

Embodiment C2. The method of embodiment C1, wherein the labeled probe comprises a defined nucleic acid structure composed of a predetermined number of unlabeled and labeled oligonucleotides.

Embodiment C3. The method of any prior C embodiment, wherein at least one member of each pair of reporter oligonucleotides has a tail that does not hybridize to the first oligonucleotides or ligation products of the same and, in step (e) the labeled probe hybridizes with the tail of a reporter oligonucleotide in the reporter probe.

Embodiment C4. The method of embodiment C3, wherein step (c) not performed, step (d) and (I are done in situ and, in step (e), the labeled probe is hybridized to the tail of a reporter oligonucleotide in the reporter probe.

Embodiment C5. The method of embodiment C3, wherein step (c) is performed and:
one member of each pair of reporter oligonucleotides has an end that contains a reactive group and the other member has a tail that does not hybridize to the first oligonucleotides or ligation products of the same,
in step (c) the reporter probe becomes tethered to the support via the reactive group; and
in step (d), the reporter probe is detected in situ by hybridization of the labeled probe to the tail of a reporter oligonucleotide in the reporter probe.

Embodiment C6. The method of embodiment C1, wherein step (b) comprises:
(b) (i) joining pairs of first oligonucleotides together, in situ, to produce a first product, and
(ii) joining pairs of reporter oligonucleotides together using the first product as a template, in situ, to produce the reporter probe.

Embodiment C7. The method of embodiment C6, wherein step (d) comprises removing unreacted reporter oligonucleotides and other single-stranded DNA molecules by exonuclease treatment or by washing at a temperature that is lower than the Tm of a reporter probe:first product duplex.

Embodiment C8. The method of any prior C embodiment, wherein the ligation product of (b)(ii) is made by a ligation or a gap-fill/ligation reaction.

Embodiment C9. The method of any prior C embodiment, wherein the ligation product of (b)(ii) is made using a splinted ligation reaction.

Embodiment C10. The method of embodiment C6, wherein (i) and (ii) are done in separate reactions.

Embodiment C11. The method of embodiment C6, wherein (i) and (a)(ii) are done in same reaction in which the reporter oligonucleotides are pre-hybridized with the first oligonucleotides and serve as a splint for joining the first oligonucleotides together, and one of the first oligonucleotides serve as template for ligating the reporter oligonucleotides.

Embodiment C12. The method of any preceding C embodiment, wherein the binding agents of step (a) are oligonucleotide probes, antibodies, or aptamers.

Embodiment C13. The method of any of the preceding C embodiments, wherein the biological sample is a tissue section.

Embodiment D1. A method for analyzing a biological sample, comprising:
(a) performing a proximity assay in situ in a biological sample to produce a proximity assay reaction product;
(b) transferring the proximity assay reaction product into or onto a support in a way that preserves the spatial relationship of the proximity assay reaction products in the sample;
(c) labeling the proximity assay reaction product on the support by:
(i) hybridizing the proximity assay reaction product with a first bridging oligonucleotide and a second bridging oligonucleotide, wherein the first and second bridging oligonucleotides hybridize to different sequences in the proximity assay reaction product; and (ii) hybridizing the first and second bridging oligonucleotides that are hybridized to the proximity assay reaction product with a labeled complex composed of a predetermined number of unlabeled oligonucleotides and a predetermined number of labeled oligonucleotides hybridized in a complex, wherein the labeled complex hybridizes to both bridging oligonucleotides; and (d) detecting the hybridized labeled complex at a resolution that can detect hybridization of a single labeled complex.

Embodiment D2. The method of embodiment D1, wherein:

the first and second bridging oligonucleotides have tails that do not hybridize to the proximity assay reaction product;

at least some of the unlabeled oligonucleotides in the labeled complex hybridize with the tails of both the first and second bridging oligonucleotides; and the labeled complex comprises a defined number of labeled oligonucleotides, wherein the labeled oligonucleotides are hybridized to the labeling oligonucleotides.

Embodiment D3. The method of any prior D embodiment, wherein a labeled complex comprises 4-20 labeling oligonucleotides and 8-200 labeled detection oligonucleotides.

Embodiment D4. The method of any prior D embodiment, wherein the first bridging oligonucleotide has a first stabilization sequence and the second bridging oligonucleotide has a second stabilization sequence, and the first and second stabilization sequences hybridize to one another when the first and second bridging oligonucleotides are hybridized to the proximity assay reaction product.

Embodiment D5. The method of embodiment D 4, wherein the stabilization sequences are 4-10 bp in length, wherein one stabilization is at the 3' end of the first bridging oligonucleotide and the other stabilization sequence is at the 5' end of the second bridging oligonucleotide.

Embodiment D6. The method of any prior D embodiment, wherein the biological sample is a tissue section.

Embodiment D7. The method of any prior D embodiment, wherein, in step (b) the sequences to which the first and second first bridging oligonucleotides hybridize in the proximity assay reaction product are brought together in into a single molecule in the proximity assay of (a).

Embodiment D8. The method of any of embodiments prior D embodiment D1 wherein the proximity assay comprises:

(b) (i) joining pairs of first oligonucleotides together, in situ, to produce a first product, wherein the first oligonucleotides that are joined together are each part of a binding agent-oligonucleotide conjugate that is bound to the sample, and (ii) joining pairs of reporter oligonucleotides together using the first product as a template, in situ, to produce the reporter probe, and wherein, in step (c), the first and second bridging oligonucleotides hybridize to the reporter probe.

Embodiment D9. The method of embodiment D8, wherein at least one member of each pair of reporter oligonucleotides has a tail that does not hybridize to the first product and wherein the labeled complex hybridizes with the tail of a reporter oligonucleotide in the reporter probe.

Embodiment D10. The method of any prior D embodiment, further comprising treating the sample or support with an exonuclease between steps (a) and (c) to remove unreacted single-stranded DNA molecules.

Embodiment D11. The method of any prior D embodiment, wherein the binding agents used in the proximity assay of step (a) are oligonucleotide probes, antibodies, or aptamers.

Embodiment E1. A method for analyzing a biological sample, comprising:

(a) performing a proximity assay in situ in a biological sample to produce a proximity assay reaction product;

(b) labeling the proximity assay reaction product in situ by:

(i) hybridizing the proximity assay reaction product with a first bridging oligonucleotide and a second bridging oligonucleotide, wherein the first and second bridging oligonucleotides hybridize to different sequences in the proximity assay reaction product; and (ii) hybridizing the first and second bridging oligonucleotides that are hybridized to the proximity assay reaction product with a labeled complex composed of a predetermined number of unlabeled oligonucleotides and a predetermined number of labeled oligonucleotides hybridized in a complex, wherein the labeled complex hybridizes to both bridging oligonucleotides; and (c) detecting the hybridized labeled complex at a resolution that can detect hybridization of a single labeled complex.

Embodiment E2. The method of embodiment E1, wherein:

the first and second bridging oligonucleotides have tails that do not hybridize to the proximity assay reaction product;

at least some of the unlabeled oligonucleotides in the labeled complex hybridize with the tails of both the first and second bridging oligonucleotides; and the labeled complex comprises a defined number of labeled oligonucleotides, wherein the labeled oligonucleotides are hybridized to the labeling oligonucleotides.

Embodiment E3. The method of any prior E embodiment, wherein a labeled complex comprises 4-20 labeling oligonucleotides and 8-200 labeled detection oligonucleotides.

Embodiment E4. The method of any prior E embodiment, wherein the first bridging oligonucleotide has a first stabilization sequence and the second bridging oligonucleotide has a second stabilization sequence, and the first and second stabilization sequences hybridize to one another when the first and second bridging oligonucleotides are hybridized to the proximity assay reaction product.

Embodiment E5. The method of embodiment E4, wherein the stabilization sequences are 4-10 bp in length, wherein one stabilization is at the 3' end of the first bridging oligonucleotide and the other stabilization sequence is at the 5' end of the second bridging oligonucleotide.

Embodiment E6. The method of any prior E embodiment, wherein the biological sample is a tissue section.

Embodiment E7. The method of any prior E embodiment, wherein, in step (b) the sequences to which the first and second first bridging oligonucleotides hybridize in the proximity assay reaction product are brought together in into a single molecule in the proximity assay of (a).

Embodiment E8. The method of any of embodiments E1-E6, wherein the proximity assay comprises:

(b) (i) joining pairs of first oligonucleotides together, in situ, to produce a first product, wherein the first oligonucleotides that are joined together are each part of a binding agent-oligonucleotide conjugate that is bound to the sample, and (ii) joining pairs of reporter oligonucleotides together using the first product as a template, in situ, to produce the reporter probe, and wherein, in step (b), the first and second bridging oligonucleotides hybridize to the reporter probe.

Embodiment E9. The method of embodiment E8, wherein at least one member of each pair of reporter oligonucleotides has a tail that does not hybridize to the first product and wherein the labeled complex hybridizes with the tail of a reporter oligonucleotide in the reporter probe.

Embodiment E10. The method of any prior E embodiment, further comprising treating the sample with an exonuclease prior to step (b) to remove unreacted single-stranded DNA molecules.

Embodiment E11. The method of any prior E embodiment, wherein the binding agents used in the proximity assay of step (a) are oligonucleotide probes, antibodies, or aptamers.

In any embodiment of A-G, the releasing may be done by contacting the biological sample with the support with the biological sample facing the support (i.e., by sandwiching the sample between two supports, and then heating the sample.

In any embodiment of A-G, the planar sample may produced by passing a suspension of cells through a filter, wherein the cells are retained on the filter. The cells on the filter are the planar support.

Embodiment G1. A method for analyzing a suspension of cells, comprising: (a) filtering a suspension of cells through a porous capillary membrane, thereby distributing the cells on the membrane; (b) placing the membrane on a planar support with the cell side of the membrane facing the support; (c) transferring nucleic acids from the cells into or onto the support in a way that preserves the spatial relationship of the nucleic acid in the cells; (d) removing the porous capillary membrane and cells from the support; and (e) spatially analyzing the nucleic acids transferred to support.

Embodiment G2. The method of embodiment G1, wherein: the method further comprises, between steps (a) and (c), performing a proximity assay on one or more pairs of binding agent-oligonucleotide conjugates that are bound to the cells, in situ, to produce proximity assay reaction products in or on the cells, and the nucleic acids transferred in step (c) and analyzed in step (e) comprise the proximity assay reaction products.

Embodiment G3. The method of embodiment G2, wherein step (e) comprises: (i) labeling the transferred proximity assay reaction products in or on the support; and (ii) imaging the support to produce an image of the sites to which the proximity assay reaction products are bound to in or on the support.

Embodiment G4. The method of embodiment G2 or G3, wherein the proximity assay comprises any combination of a ligation, a primer extension, and a gap-fill/ligation reaction involving the oligonucleotides of the binding agent-oligonucleotide conjugates.

Embodiment G5. The method of any prior G embodiment, wherein the planar support of (b) comprises an array of spatially barcoded capture oligonucleotides, step (c) comprises hybridizing the transferred nucleic acids to the spatially barcoded capture oligonucleotides, and step (e) comprises extending the capture oligonucleotides using the transferred nucleic acids as a template and sequencing copies of the primer extension templates to produce sequence reads.

Embodiment G6. The method of embodiment G5, further comprises mapping the sequence reads to site on the support using the spatial barcodes in the sequence reads.

Embodiment G7. The method of any prior G embodiment, wherein the transferring step (c) is done by electrophoresis or diffusion.

Embodiment G8. The method of any prior G embodiment, wherein the porous capillary membrane is a porous anodic aluminum oxide membrane.

Embodiment G9. The method of any prior G embodiment, wherein step (a) is done by: (i) placing the suspension of cells on the porous capillary membrane; and (ii) applying a force that moves the liquid component of the suspension through the membrane.

Embodiment G10. The method of embodiment G7, wherein the force is an active force selected from centrifugal force, negative pressure and positive pressure or a passive force selected from capillary action and evaporation.

Embodiment G11. The method of any prior G embodiment, further comprising washing the porous capillary membrane between steps (d) and (e).

Embodiment G13. The method of any prior G embodiment, wherein the interior diameter of the pores in the membrane is in the range of 2 nm to 500 nm.

Embodiment G14. The method of any prior G embodiment, wherein the average distance between the centers of adjacent pores in the membrane is in the range of 50 nm to 1000 nm.

Embodiment G15. The method of any prior G embodiment, wherein the average distance between the edges of adjacent pores in the membrane is in the range of 10 nm to 500 nm.

Embodiment G16. The method of any prior G embodiment, wherein the suspension of cells comprises blood cells, immune cells, single cells that have been separated from one another by trypsin treatment, or a cells have been cultured as a suspension.

Embodiment G17. The method of embodiment G2, wherein:
the binding agent-oligonucleotide conjugates each comprise: i. a binding agent that binds to a site or sequence in the sample and ii. a first oligonucleotide, and the proximity assay comprises joining pairs of reporter oligonucleotides together, in situ, to produce a reporter probe, wherein the joining of the reporter oligonucleotides is templated by either i. first oligonucleotides that are proximal to one another or ii. a ligation product of the same; and the reporter probes are transferred to the support in step (c); and step (e) comprises detecting the reporter probes, on the support, by hybridization of a labeled probe to the reporter probe.

Embodiment G18. The method of embodiment G17, wherein the method further comprises removing unreacted reporter oligonucleotides and other single-stranded DNA molecules by exonuclease treatment or by washing.

Embodiment G19. The method of embodiment G17 or G18, wherein at least one member of each pair of reporter oligonucleotides has a tail that does not hybridize to the first oligonucleotides or ligation products of the same and, in step (e) the labeled probe hybridizes with the tail of a reporter oligonucleotide in the reporter probe.

Embodiment G20. The method of any of embodiments G17-G19, wherein: one member of each pair of reporter oligonucleotides has an end that contains a reactive group and the other member has a tail that does not hybridize to the first oligonucleotides or ligation products of the same, in step (c) the reporter probe becomes tethered to the support via the reactive group; and in step (e), the reporter probe is detected by hybridization of the labeled probe to the tail of a reporter oligonucleotide in the reporter probe.

EXAMPLES

To further illustrate some embodiments of the present invention, the following specific examples are given with the understanding that they are being offered to illustrate examples of the present invention and should not be construed in any way as limiting its scope.

Example 1

This example provides an assay that comprises converting the information about proximally located biomolecules into DNA and transferring the DNA to a planar support. The DNA on the planar support is detected to identify the information about the proximally located biomolecules or detecting single biomolecules targeting two separate epitopes or loci. Thus, in these methods, information about proximal biomolecules is converted to DNA molecules, which are analyzed in a streamlined, multiplexed format.

This example describes conducting a PA to transfer protein information to DNA. For example, using a PA ensures specificity and transfer of both RNA and DNA molecules from PA into one reporter molecule format, i.e., DNA. The design allows short oligos to be used for the proximity ligation to ensure tight proximity requirement in the PA assay. These shorter oligonucleotides are then converted into longer oligonucleotides that enables hybridization-based barcode readout in a second step.

In this example, the detection is designed to be a programmable cascade of a defined number of detection fluorophores. By transferring the nucleic acid reaction products to a planar support, it is easier to perform single molecule detection with lower background compared to analysis in the tissues, where background fluorescence is high. Imaging time is also reduced since there is no need or reduced need to image z-stacks when imaging molecules on a planar surface.

In this example, instead of using rolling circle replication where the exact amplification level is difficult to control, actual number of nucleic acid reaction products produced during PA are detected. Moreover, a controlled hybridization reaction chemistry where an exact number of fluorophores are added to each target molecule creates a more even detection of target single molecules. Thus, spatial detection of proteins and protein interactions without RCA allows analysis/detection of smaller fluorescent molecules in higher density. After each detection cycle the labelled detection oligonucleotides are washed off and only the individual reporter molecules remain on the surface to avoid physical crowding on the surface.

In this example, the following protocol is followed to analyze a planar biological sample.

A tissue section is immobilized on a solid support. The information about the locations of proteins is converted into DNA molecules by ligating oligonucleotide conjugated to antibodies. For each detected protein, protein modification or protein/protein interaction, two antibodies are used. An antibody mix containing multiple pairs of antibodies are incubated and allowed to bind respective target proteins in the tissue.

The antibody pairs are designed so that one oligonucleotide conjugated to an antibody in a pair has a free 3' end and the other oligonucleotide conjugated to another antibody in the pair has a free 5'end. Unbound antibodies are washed away, and antibodies are optionally fixed in the tissue. Fixing the antibodies in the tissue helps withstand subsequent washes and incubations.

Splints that are complementary to the pairs of oligonucleotides are added. Ligase is then added to allow ligation of the oligonucleotides form the pairwise antibodies if they are bound in proximity. Splints are designed such that they stably hybridize to two oligonucleotides conjugated to two antibodies bound in proximity.

Splints can also be added that allow for combinatorial ligation of one antibody to many other antibodies to interrogate specific potential interactions or protein modifications. Alternatively, all 3' conjugated antibodies could be ligated to all 5' conjugated antibodies. However, the risk of getting significant noise/background is higher because many proteins will be proximal by chance and not by protein-protein interaction. In this case, signal to noise ration can be determined by comparing counts from different cell populations to see statistically significant fluctuations of interaction patterns between cell populations. Signal from detection using two binding agents targeting the same protein and two binding agents targeting an interaction involving the same protein can also be measured and used as internal reference.

The splints are washed away, and reporter probes are added. The reporter probes can be designed so that they hybridize to ligated oligonucleotides from proximal antibodies. Certain reporter probes can also be designed that hybridize to RNA targets. The reporter probes are designed so that they form reporter polynucleotides with barcodes corresponding to the ligated oligonucleotides to which they hybridize or and RNA molecules to which they hybridize. Thus, the sequences of barcodes in the reporter probes and resulting reporter polynucleotides contain information about the targeted proteins and target RNA.

Reporter probe pairs are designed with one ligatable end each. One of the probes is equipped with an affinity moiety. Optionally, the unligated ends of the reporter polynucleotides can be modified to render it resistant to exonuclease. The affinity moiety is advantageously inducible like a click chemistry reactive group. The affinity moiety can also be a DNA sequence that is ligatable using a specific sequence. The affinity moiety can even be a binding member of a specific binding pair that specifically binds to a member present on the planar support.

Upon hybridization to the ligated oligonucleotides and/or RNA molecules in the tissue, the reporter probes contain combinations of barcodes that together constitute a unique barcode designed to be decoded by detection of the reporter polynucleotides.

The steps of ligating the splint and the reporter probes can be performed in the same reaction. This would mean two ligation sites for protein molecules which might reduce efficiency but on the other hand only one ligation step would be required, which would increase efficiency. Ligation would also need to be specific for the RNA molecules under the same conditions.

The excess reporter probes are washed away. The reporter probes in the tissue are transferred to a solid phase and attached using the affinity moiety on the reporter polynucleotides. To facilitate transfer of the reporter polynucleotides to the planar support, the reporter polynucleotides can be released from their targets, for example, using denaturing conditions with chemicals, such as NaOH, formamide, urea, guanidine or urea, and temperature. The release can also be facilitated by cleaving the cleavable linker between the antibodies and the conjugated oligonucleotides.

Alternatively, the release can be mediated enzymatically using RNA to degrade RNA targets and thereby releasing reporter probes bound to RNA and designing oligonucleotides conjugated to antibodies with uracil bases that can be degraded using Uracil-DNA glycosylase. The respective release chemistry is selected so that it is compatible with the affinity chemistry on the surface and the transfer mechanism to the surface.

The planar support can be either the same solid support on which the tissue section is immobilized, or a second support provided on top of the tissue. In the former case, the affinity reaction needs to be inducible because without it the probes would block the surface during hybridization where excess of probes are added. In one example of such affinity reaction, click chemistry is used that requires copper to create a covalent bond. In another example, ligation is performed to oligonucleotides immobilized on the surface using a templating splint thereby facilitating covalent ligation of the reporter polynucleotides to the oligonucleotide that is immobilized on the solid support.

Alternatively, another the planar support can used to transfer the reporter polynucleotides from the tissue. The transfer of reporter polynucleotides from the tissue to the planar support can be accelerated using electrophoresis.

In one example, instead of using a planar solid support the tissue is immobilized in a clearing gel matrix support following ligation of the reporter probes. One of the reporter probes are equipped with a moiety immobilizing the reporter polynucleotide in the gel. Following polymerization of the gel the tissue components can be cleared from the gel without damaging the DNA polynucleotides.

Single molecule identification of immobilized reporter polynucleotides is then performed. The reporter polynucleotides contain a given set of barcodes to be detected. For example, if two colors per detection cycle are analyzed and 16 cycles are run, 32 different barcodes will be read. The barcodes can be designed so that each reporter polynucleotide has a unique set of barcodes from 32 barcode combinations.

Detection probes are added in multiple cycles and in each cycle different barcode(s) are labelled thereby detecting the binary string of barcodes present in each reporter polynucleotide. Each cycle comprises labeling, washing, imaging, and eliminating the detection probes before the next cycle begins.

The detection scheme can be designed so that in each cycle first a pair of bridging probes are hybridized to each respective barcode converting the barcode to a longer oligonucleotide for detection (FIG. 5). The bridging probes can be advantageously designed so that they stabilize each other and upon hybridization by weak complementary hybridization, stacking hybridization or enzymatic ligation, and that they are not stable individually Following hybridization of the bridging probes, detection probes are added. The detection probes require presence of both bridging probes in proximity to form a stable hybridization. This ensures that background adsorption of individual bridging probes do not generate background. In this example, each bridging probe can hybridize to three detection probes. Each detection probe is designed to be able to hybridize to multiple (e.g., nine) labelling probes. Each detection probe generates too weak signal individually to generate a signal over background while three detection probes each labelled with nine labelling probes aggregate a total of 27 labels which is designed to generate signal over background (FIG. 5). The detection probes and labelling probes can be pre hybridized together and added in the same step.

Given that one pair of bridging probes is attached to one reporter polynucleotide, multiple detection probes each hybridized to several labeling probes are required to be hybridized to one pair of bridging probe to register a signal over background. This design ensures that signal generation specificity is maintained. Individual bridging probes would not create background if they stick to the surface and individual detection probes or labeling probes do not create sufficient signal to generate a signal over background. Multiple labels with different fluorophores can be used so that multiple barcodes can be detected in one labeling cycle. The hybridization chemistry is designed to have a defined number of fluorophores for each target molecule.

Example 2

In this example an antibody oligonucleotide conjugate is used. Oligonucleotide A is conjugated to the antibody A to create conjugate A. Before allowing conjugate A to bind to the its target, protein A in the tissue oligonucleotide A' is hybridized to oligonucleotide A. Oligonucleotide A' also carries a biotin in the 5'end and a fluorophore in the 3'end has an additional sequence A'1 not complementary to oligonucleotide A. Conjugate A hybridized to oligonucleotide A' is allowed to bind to a FFPE tissue section immobilized on a glass slide flowing appropriate sample preparation including for example antigen retrieval and blocking. The tissue section is then washed, and a capture planar support coated with streptavidin is positioned facing the tissue section. The glass slide with the tissue and the planar support is held into place and the slides are placed in an oven allowing the temperature to increase above the melting temperature of oligonucleotide A and oligonucleotide A'. Oligonucleotide A' is then captured on the planar support using the streptavidin-biotin interaction. The slide is imaged using fluorescent microscopy, and oligonucleotide A can be detected using the fluorescent molecule attached. The pattern on the planar support represents a mirror image of the tissue.

Example 3

Transfer of Reporter Oligonucleotides from an Antibody Conjugate and, Detection on the Capture Surface Using Immune Fluorescence Antibody-oligonucleotide conjugation: The antibodies against keratin 8 (cat no 904804, Biolegend) and keratin 18 (cat no 628402, Biolegend) were buffer exchanged to DPBS using 0.5 mL Zeba™ Spin Desalting Columns 7K MWCO were used to exchange the buffer and concentrated to 1 mg/ml using Amicon® Ultra-0.5 Centrifugal Filter 10K MWCO devices. DBCO-NHS-ester (cat no 761524, Sigma-Aldrich) was dissolved and diluted to 2 mM in DMSO. A 15-fold molar excess of DBCO-NHS ester was added to the antibody, and the reaction was incubated for 45 minutes at RT protected from light. 1M Tris-HCl pH 8 was added to a final concentration of 30-100 mM, and the reaction was incubated for 5 min at RT. A 0.5 mL Zeba™ Spin Desalting Column 7K MWCO, (Thermo Scientific cat. no 89882) equilibrated to DPBS was used according to manufacturer's instructions to remove unreacted DBCO-NHS ester. A 2.5-fold molar excess of azide-modified DNA oligonucleotide was added to the antibody activated with DBCO. The reaction was incubated in a fridge (2-8° C.) for at least 60 hours. Successful conjugation was verified with polyacrylamide gel electrophoresis, staining conjugates with SYBR Gold Nucleic Acid Gel stain (S11494, Invitrogen) and InstantBlue Coomassie Protein Stain (Abcam, ab119211). Antibody-oligonucleotide conjugates were diluted to 0.15 µg/µl in DPBS with 0.1% BSA and 0.02% $NaN_3$.

Tissue preparation: Tissue microarrays with cores from FFPE blocks were sectioned in 4 µm thick sections, and placed on TOMO glass slides (Matsunami). After baking, the slides were deparaffinized in xylene (2 times for 5 min) and hydrated in a series of graded ethanol to deionized water. Endogenous peroxidases were blocked with 3% $H_2O_2$ in PBS for 10 min at RT. The slides were rinsed 1 time in PBS. For antigen retrieval Antigen Retrieval Buffer, Citrate Buffer, pH 6.0 [Abcam, ab93678] was used for 50 min at 98° C. The slides were rinsed 1 time in PBS. A barrier was created by drawing with an ImmEdge™ hydrophobic barrier pen. Finally, the slides were rinsed in TBS with 0.05% Tween-20.

Staining: The avidin blocking buffer was prepared as follows: 1×TBS, 0.05% Tween-20, 0.25 mg/ml BSA, 0.5 mg/ml salmon sperm DNA (Sigma), avidin 5 µg/ml.

Avidin blocking buffer was applied to cover the TMA and the slides were incubated for 1 h at RT in a humidity chamber. Finally, 2 washes of 2 min in TBS with 0.05% Tween-were performed.

The biotin blocking buffer was prepared as follows: 1×TBS, 0.05% Tween-20, 0.25 mg/ml BSA, 0.5 mg/ml salmon sperm DNA (Sigma), biotin 12.5 µg/ml, 10 mg/ml dextran sulfate.

Biotin blocking buffer was applied to cover the TMA and the slides were incubated for 1 h at RT in a humidity chamber.

The Keratin-18 antibody was diluted in biotin blocking solution to 0.75 ng/µl. Then it was applied to cover the TMA and the slides incubated for 1 h at RT in a humidity chamber. Finally, 3 washes of 5 min in TBS with 0.05% Tween-20 at 45° C. were performed.

Once more, biotin blocking buffer was applied to cover the TMA and the slides were incubated for 1 h at RT in a humidity chamber.

The hybridization buffer was prepared as follows: 10 mM tris acetate, 10 mM magnesium acetate, 50 mM potassium acetate, 0.5 mg/ml BSA, 250 mM NaCl, 0.05% Tween-20, water to final volume.

The DNA oligo (22 bp, biotinylated and with fluorophore) was diluted in hybridization buffer to 50 nM and incubated on the TMA for 30 min at 37° C. in a humidity chamber. Finally, 3 washes of 5 min in TBS with 0.05% Tween-20 at 45° C. were performed. Glass cover slip avidin coating: Glass cover slip: 200 nm biotin derivatized linear polycarboxylate hydrogel, medium charge density (XanTec bioanalytics GmbH).

The cover slip was rinsed 1 time with PBS and incubated for 1 h at RT in 0.1 mg/ml avidin (in PBS). Then it was wash 3 times in PBS.

Transfer: The tissue slide and cover slip were incubated in 10 mM NaAc pH 5.5 solution for 15 min. The two glasses were aligned and put together without creating air bubbles and then incubated at 60° C. for 75 min in a humidity chamber. Finally, the cover slip was carefully separated from the glass slide.

Mounting: The transferred cover slip was incubated with biotinylated fluorescent 1 µm beads for 5 min at RT (for focus proposes). Then it was washed 3 times for 2 min in TBS with 0.05% Tween-20. Finally, the tissue slide, and the transferred cover slip were separately mounted with EverBrite Hardset Mounting Medium.

Imaging: The slides were imaged in a 3D Histech slide scanner according to the manufacturer's instructions.

Figure 7:
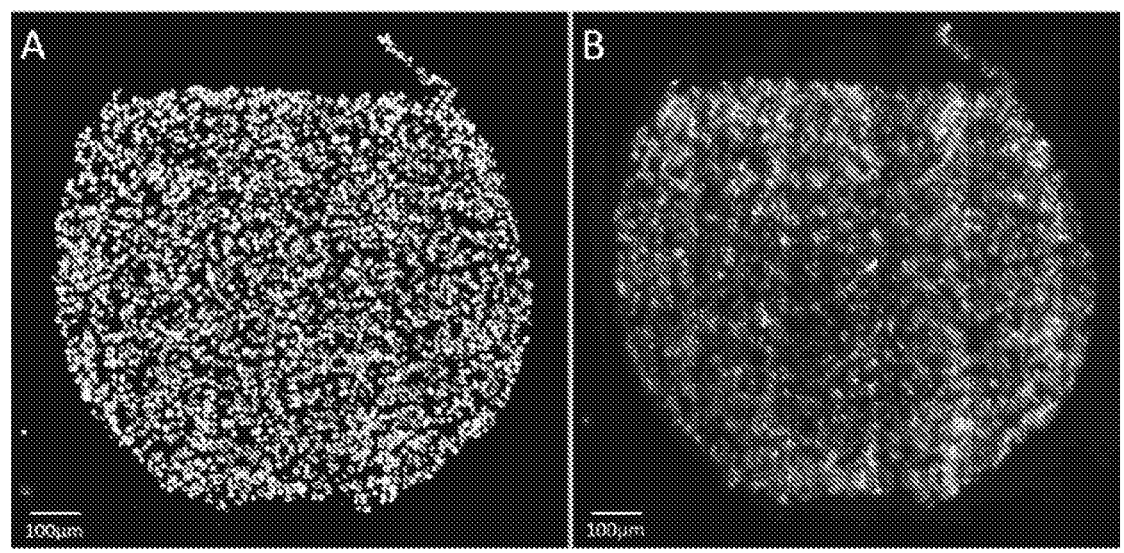

Results:

The assay was designed to target Keratin-18 in a sample with 1 mm microarray features of the FFPE fixed cell line MCF7. Cells can be visualized on the originating tissue slide (FIG. 7A) and individual cells imprints (product of the transfer of ssDNA fluorescent oligos) are also visible on the capture surface (FIG. 7B) demonstrating transfer with retained spatial resolution of the sample.

Example 4

Detection of PLA-Generated Reporter Probes by Hybridization Chain Reaction (HCR) on the Capture Surface Following Transfer Antibody and tissue preparation: As described above.

Figure 8:
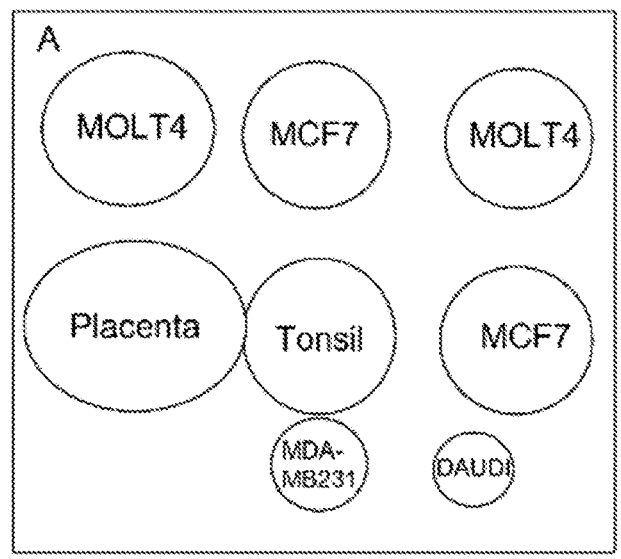
FIG. 8 Illustration of TMA describing locations of different cell lines and tissue types.

TMA with human tonsil, human placenta, MCF7 cells and MOLT4 cells, and 0.6 mm cores of FFPE DAUDI cells and MDA-MB231 described in FIG. 8.

Proximity Ligation Assay (PLA)

Tissue blocking: The avidin blocking buffer was prepared as follows: TBS, 0.05% Tween-20, 0.25 mg/ml BSA, 0.5 mg/ml salmon sperm DNA (Sigma), avidin 5 µg/ml.

Avidin blocking buffer was applied to cover the TMA section and the slides were incubated for 1 h at RT. Finally, 2 washes of 2 min in TBS with 0.05% Tween-20 were performed.

The biotin blocking buffer was prepared as follows: TBS, 0.05% Tween-20, 0.25 mg/ml BSA, 0.5 mg/ml salmon sperm DNA (Sigma), biotin 12.5 µg/ml.

Biotin blocking buffer was applied to cover the TMA and the slides were incubated for 30 min at RT. The slides were rinsed once with in TBS with 0.05% Tween-20.

Antibody incubation: A pair of antibody-oligonucleotide conjugates were diluted to 1 µg/ml of each antibody in biotin blocking buffer. The diluted conjugates were applied to the slides. The slides were incubated at 4° C. overnight. Slides were washed 2 times for 5 min in TBS with 0.05% Tween-20.

Proximity ligation assay (PLA) to generate ligated reporter probes: The two target oligonucleotides were ligated by adding 125 nM splint, 0.04 U/µl T4 DNA ligase (ThermoScientific), 10 mM tris acetate, 10 mM magnesium acetate, 50 mM potassium acetate, 0.5 mg/ml BSA, 200 mM NaCl, and 0.05% Tween-20. The reaction was incubated for 30 min at 37° C. in a humidity chamber. This splint templated ligation step was omitted for the no ligation negative control. The slides were washed 2 times for 5 min in TBS with 0.05% Tween-20.

Reporter oligonucleotides, one with a biotin and one with Alexa647, were diluted to 33 nM in 10 mM tris acetate, 10 mM magnesium acetate, 50 mM potassium acetate, 0.5 mg/ml BSA, 250 mM NaCl, and 0.05% Tween-20, and then added to the slides to hybridize to the first ligation products. The hybridization reaction was incubated for 30 min at 37° C. in a humidity chamber. The slides were then washed 2 times for 5 min in TBS with 0.05% Tween-20. The reporter oligonucleotides were then ligated by adding 0.04 U/µl T4 DNA ligase (ThermoScientific), 10 mM tris acetate, 10 mM magnesium acetate, 50 mM potassium acetate, 0.5 mg/ml BSA, 200 mM NaCl, and 0.05% Tween-20, during a 30 min incubation at 37° C. in a humidity chamber. The slides were washed 2 times for 2 min in TBS with 0.05% Tween-20.

Unligated reporter oligonucleotides were digested, and ligated reaction products/reporter probes were prepared for release with a nuclease mix containing 0.01 U/µl USER (New England Biolabs), 0.1 U/µl Lambda exonuclease (New England Biolabs), 1× rCutSmart buffer (New England Biolabs) and 0.05% Tween-20. The slides were washed 2 times for 5 min in TBS with 0.05% Tween-20.

Glass cover slip coating: As described above.

Transfer: The tissue slide and cover slip were incubated in 10 mM NaAc pH 5.5 solution for 15 min. The two glasses were aligned and put together without creating air bubbles and then incubated at 60° C. for 60 min in a humidity chamber. Finally, the cover slip was carefully separated from the glass slide.

HCR detection of reporter molecules on cover slips: The area where transfer should have occurred was delineated with an ImmEdge pen (Vector Laboratories). Cover slips were incubated with (Biotin-Labeled micropspheres, 0.2 µM, yellow-green fluorescent (505/515) in 2×SSC (Sigma) for 15 min at RT. The cover slips were washed 3 times for 2 min with 2×SSC with 0.1% Tween-20. Probes with HCR initiator sequences, recognizing the reaction products/reporter probes were diluted to 10 nM in 4×SSC with 20% ethylene carbonate and 0.1% Tween-20, and added to the cover slips. The cover slips were incubated for 1 hour in a humidity chamber at RT. The cover slips were washed 2 times for 5 min in 2×SSC with 0.1% Tween-20. HCR was performed as previously described by Choi, Beck and Pierce 2014 (ACS Nano 2014, 8, 5, 4284-4294). Briefly HCR hairpin probes with ATTO565 were individually diluted to 0.5 µM in 40 µl 5×SSC, incubated at 95° C. for 5 min, and then allowed to cool down at RT for 10 min. Thereafter the two hairpin probes were mixed and diluted to 10 nM in 5×SSC with 0.1% Tween-20. The HCR hairpin probe mix was applied to the cover slips, and the reaction was allowed to proceed for 3 h at RT protected from light in a humidity chamber. The cover slips were washed once with 2×SSC with 0.1% Tween-20 and once with TBS. The cover slips were mounted with SlowFade Diamond Antifade Mountant (Invitrogen) and TOMO glass slides (Matsunami).

Figure 9:
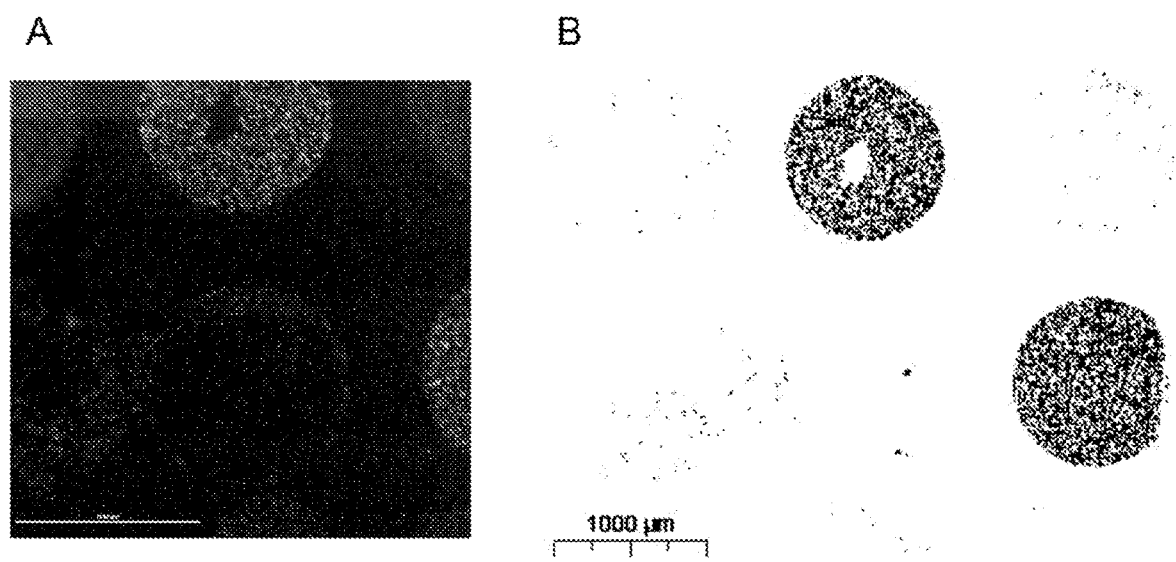
FIG. 9 panel A; Reporter molecules generated by proximity ligation assay were detected by HCR after transfer to a functionalized cover slip. Panel B: Remaining reporter molecules are chromogenically stained in the tissue TMA, here showing only the DAB staining after color deconvolution. Scale bars are 1 mm in both images.

Imaging: A 2.5×2.5 mm area of the cover slips was imaged with epifluorescence microscopy. Beads were imaged in FITC with exposure time of 25 ms (data not shown), and HCR detection of reporter probes was imaged in TRITC with exposure time of is (FIG. 9).

Results: The PLA assay was performed using one antibody targeting keratin 8 and one antibody targeting keratin 18. The assay was used to analyze a tissue microarray comprising 6 features of with two shown to be clearly positive (FIG. 9). The result is in accordance with reference literature.

Example 5

Detection of Keratin 8 and 18 Using PLA and, Readout Following Transfer of Reporter Probes to the Capture Surface Using Flow-Cell Single Molecule Sequencing Antibody and tissue preparation: As described above.

TMA with human tonsil, human placenta, MCF7 cells and MOLT4 cells, and 0.6 mm cores of FFPE DAUDI cells and MDA-MB231 described in FIG. 8.

Proximity ligation assay: As described above.

Glass cover slip avidin coating: As described above.

Transfer: The tissue slide and cover slip were incubated in 10 mM NaAc pH 5.5 solution for 15 min. The two glasses were aligned and put together without creating air bubbles and then incubated at 60° C. for 75 min in a humidity chamber. Finally, the cover slip was carefully separated from the glass slide.

Flow cell mounting: The cover slip was rinsed two times in ultra-pure water and then mounted in a Bioptechs FCS2 chamber according to the manufacturer's instructions.

Sequencing: Sequencing was performed by repeatedly introducing labeling oligonucleotides through a flow cell. The present chemistry required three different oligo solutions to be introduced sequentially in each cycle: bridging probes, labeling probes, followed by fluorescently labeled detection probes. Washing was performed between each oligo mix. The sequencing imaged a ~0.5 $cm^2$ area in each cycle.

In this set up a Fluigent fluidic system (Flow EZ™ 2000) was used to flow reagents in a controlled manner across the flow-cell and transferred surface. All reagents were injected at a flowrate of 200 µl/min. The flowrate for all washing steps was set to 800 µl/min.

Beads for field-of-view (FOV) alignment (Biotin-Labeled micropspheres, 0.2 µM, yellow-green fluorescent (505/515)) were diluted 1:20,000 in 2×SSC from the original 1% stock suspension, added manually, and incubated for at least 10 min prior starting the fluidic system.

Beads were imaged in FITC with exposure time of 100 ms, and reporter molecules, if labeled with Alexa647N, imaged in Cy5 with exposure time of 1000 ms.

Following imaging the beads, nonspecific binding was minimized by incubation at RT for 30 min with 400 µl blocking buffer (1% biotinylated bovine serum albumin (BSA), 2×SSC). Excess BSA was removed by washing with washing buffer containing salt and detergent using a continuous flow.

Bridging-oligo pairs were incubated at a final concentration of 10 nM, unless otherwise noted, at RT for minimum 1 h in 400 µl hybridization buffer (4×SSC, 0.1% Tween, 30% ethylene carbonate). The hybridization reaction was stopped by washing for 5 minutes with 4 ml washing buffer containing salt and detergent using a continuous flow.

A mix of up to five labeling probes were hybridized for 30 min at a final concentration of 10 nM each probe in hybridization buffer (30% ethylene carbonate, 0.1% Tween, 4×SSC) at RT. The hybridization reaction was stopped by washing for 5 minutes with 4 ml washing buffer containing salt and detergent using a continuous flow.

Next, fluorescently labeled detection probes were hybridized to the labeling probes for 15 min in hybridization buffer (30% ethylene carbonate, 0.1% Tween, 4×SSC) at RT. Then the surface was washed for 5 min with 4 ml washing buffer containing salt and detergent using a continuous flow to remove unbound/unspecific oligos and probes.

Signal is detected by imaging the surface in a channel matching the fluorescence of the detection probes.

Following signal detection, stripping was performed using an organic solvent or ionic compound (e.g., DMSO or NaOH) under continuous flow for minimum 10 minutes. Following stripping, the surface was washed with 4 ml washing buffer containing salt and detergent for 5 minutes using a continuous flow.

Sequencing hardware: The sequencing system was built around an inverted microscope (Nikon Ti2-E) equipped for widefield epi-fluorescence imaging, and a pressure driven flow control system (Fluigent Flow EZ 2000 and Fluigent FLOW UNIT L) with two 11-port rotary valves (Fluigent M-SWITCH) connected in series.

The two systems were controlled using custom scripts running on the proprietary software associated with each system. Synchronization of the two systems was obtained using a bidirectional TTL interface.

The microscope was equipped with a 60× oil immersion objective (Nikon CFI Plan Apochromat Lambda D 60× Oil) and an sCMOS camera (Hamamatsu ORCA-Flash4.0 LT). Three fluorescence filter sets were used for imaging in the describe experiments: Semrock LED-Cy5-A (here called Cy5) for imaging Alexa 647N and ATTO647N, Semrock LED-TRITC-A (here called TRITC) for imaging ATTO 565, and LED-FITC-A (here called FITC) for imaging the fiducial beads. The used light source was a CoolLED pE-800 with the 550 and 635 nm LED switched on and 100% for imaging with the TRITC and Cy5 channel respectively, and with the 470 nm LED switched on at 1% for imaging the fiducial beads using the FITC channel.

Figure 10:
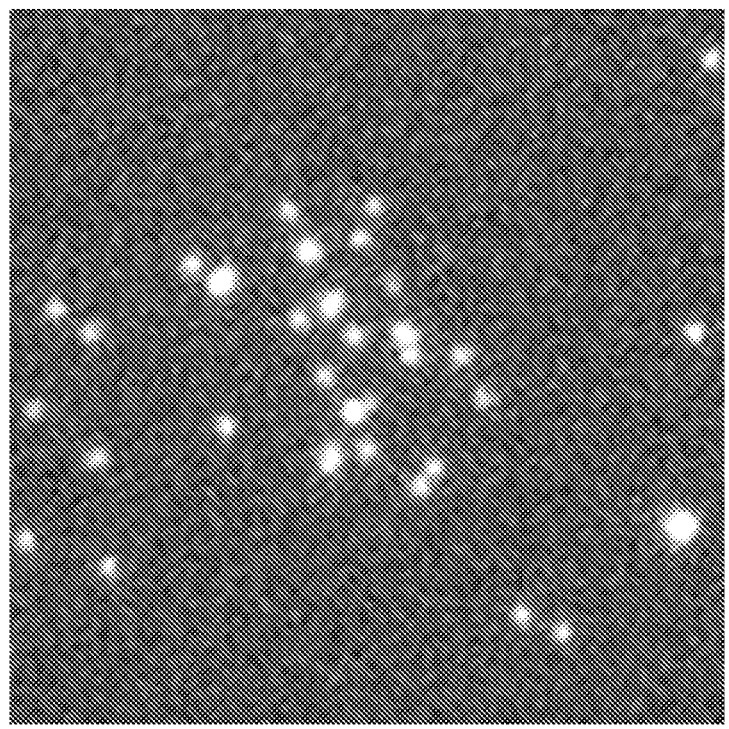
FIG. 10 shows sequencing image data obtained as bright spots on dark background.

Image analysis: The sequencing image data appears as diffraction limited bright spots on dark background for several cycles of imaging, as shown in FIG. 10. There are three sets of images acquired, corresponding to Cy5, TRITC and FITC imaging channels. The Cy5 and TRITC channels contain sequencing spots and FITC contains reference beads for image alignment. The image analysis method to detect fluorescent barcode information consisted of several steps. First, the spots in Cy5 and TRITC channel, and beads in FITC channel are detected and segmented. To segment spots and beads, a circle detection algorithm, which is tuned to the size of a spot is used. The beads detected for all different cycles are used to align the cyclic data. The spot images are preprocessed to correct for non-uniformities in foreground and background illumination. After correcting the non-uniform illumination, spot features such as position, fluorophore count and others are extracted. The alignment information obtained using the beads is used to align spots in the corresponding image cycle. The barcode information, i.e., the on or off, of a molecule over all different imaging cycles is detected using a neighborhood search of a spot through the aligned spot data. The barcode information for Cy5 and TRITC are combined to obtain the barcode in two channels of imaging. The barcode information is exported in feather format using Pandas software to be processed in the later part of analysis. In addition to the barcode information, other auxiliary information to check the quality of data and analysis such as alignment quality metric etc. are obtained. The entire analysis is done in Python software using image and data analysis libraries such as Numpy, Scipy, OpenCV etc.

Data analysis: The summary table obtained in the previous step (feather format file), which contains the information on the fluorescent spots identified in each field-of-view and in every cycle, was imported into R via the arrow and data.table packages, and the downstream analysis was performed within the R environment. The graphical representations of the results were performed using the ggplot package.

Figure 11:
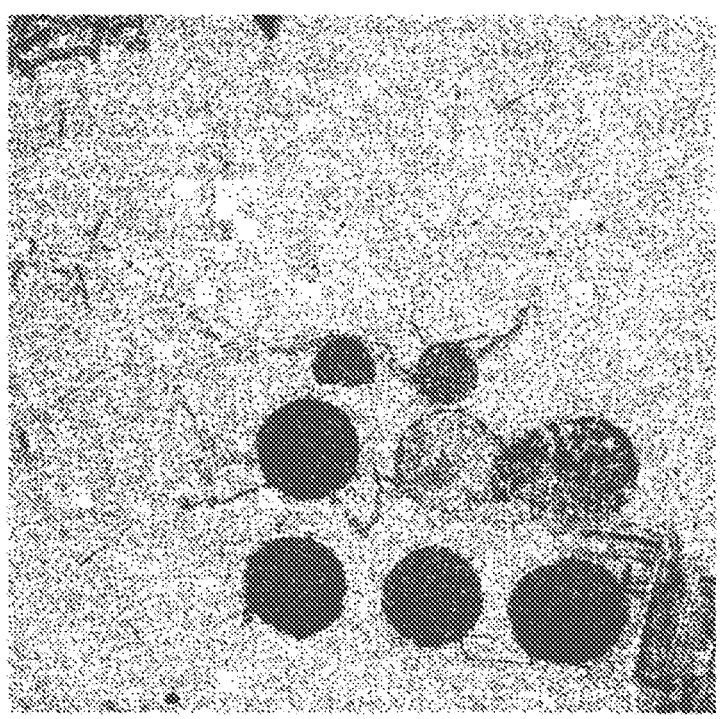
FIG. 11 shows transferred reporter molecules. Each reporter molecule is represented by a single dot. The 8 circles in the lower part of the image correspond to the TMA.

The analysis was divided into two main tasks: i) identification of the transferred reporter molecules and ii) evaluation of their detections using probes targeting their reporter sites. The former was carried out by visualizing across the sample area the distribution of spots corresponding to the fluorophores directly conjugated to each reporter molecule (FIG. 11).

Figure 12:
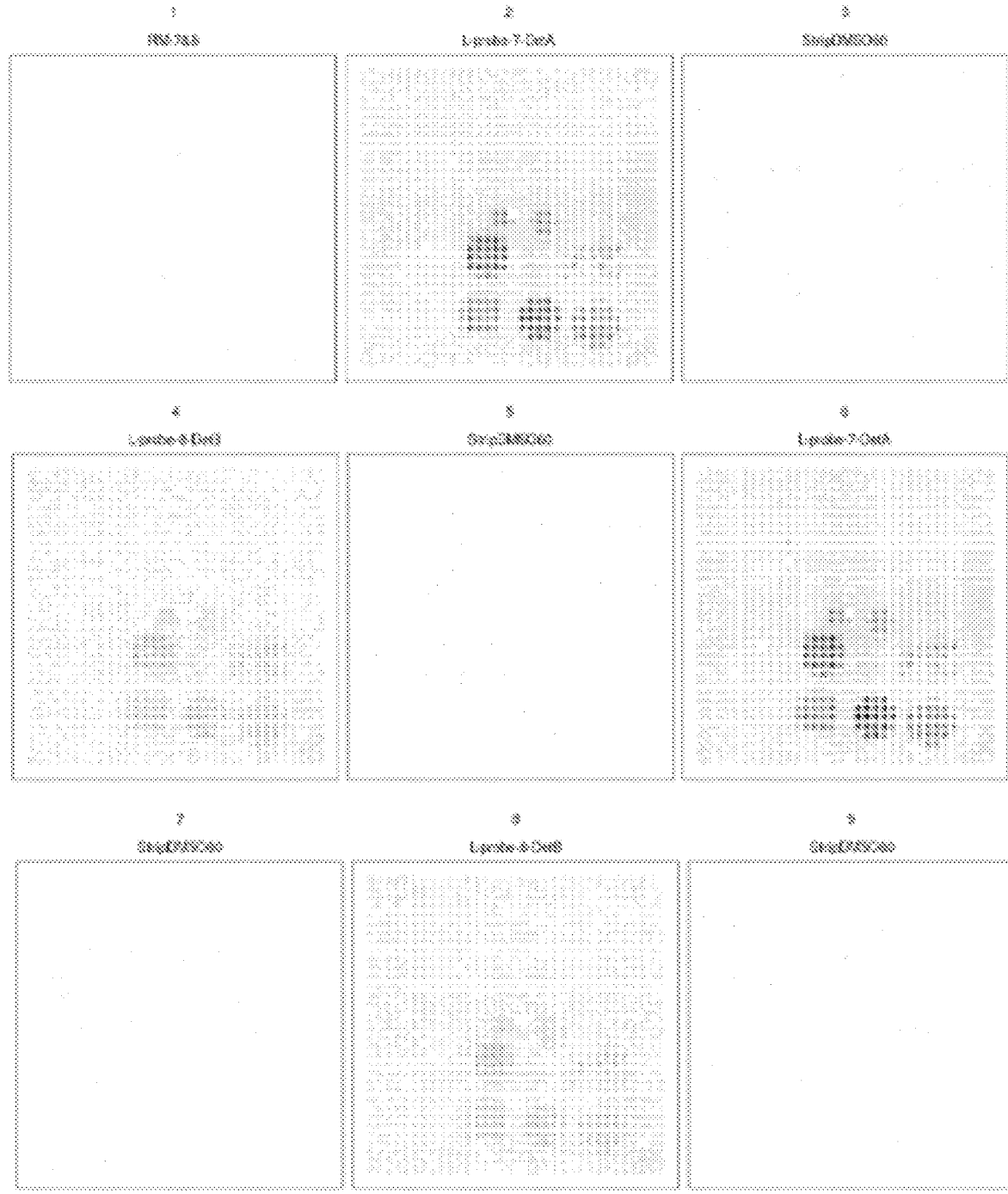
FIG. 12. shows cyclic reporter molecules detection. The detection systems are employed in cycles 2, 4, 6, and 8, with cycles 3, 5, 7, and 9 representing the stripping, or cleaning, cycles. Cycle 1 shows the sample area before the injection of any detection system.

The second part of the analysis consisted in the detection of the reference reporter molecules using sets of oligonucleotide sequences, or probes, carrying many fluorophores; each reporter molecule harbors two distinct stretches of nucleotides that are the hybridization targets of the detection system 1 and 2, separately. Since the experiment was performed alternating the injections of the detection systems, and 'stripping' cycles that were aimed at removing the probes of one system before adding those from the other, we were able to visualize which target region of the reporter molecules was detected in every cycle (FIG. 12).

To further investigate the reporter molecules detection, we carried out the analysis of the individual images that are constituting the entire sample area. Specifically, we focused on a set of four neighboring field-of-views (FoVs) overlapping one of the tissue samples. Across these FoVs, we extracted the spots detected with system 1 (FIG. 13A; detection rate=0.166) and 2 (FIG. 13B; detection rate=0.284), and co-detected with both systems (FIG. 13C; detection rate=0.098), and compared the latter to the reference reporter molecule spots (

FIG. 13D; N=1173).

Figure 13D:
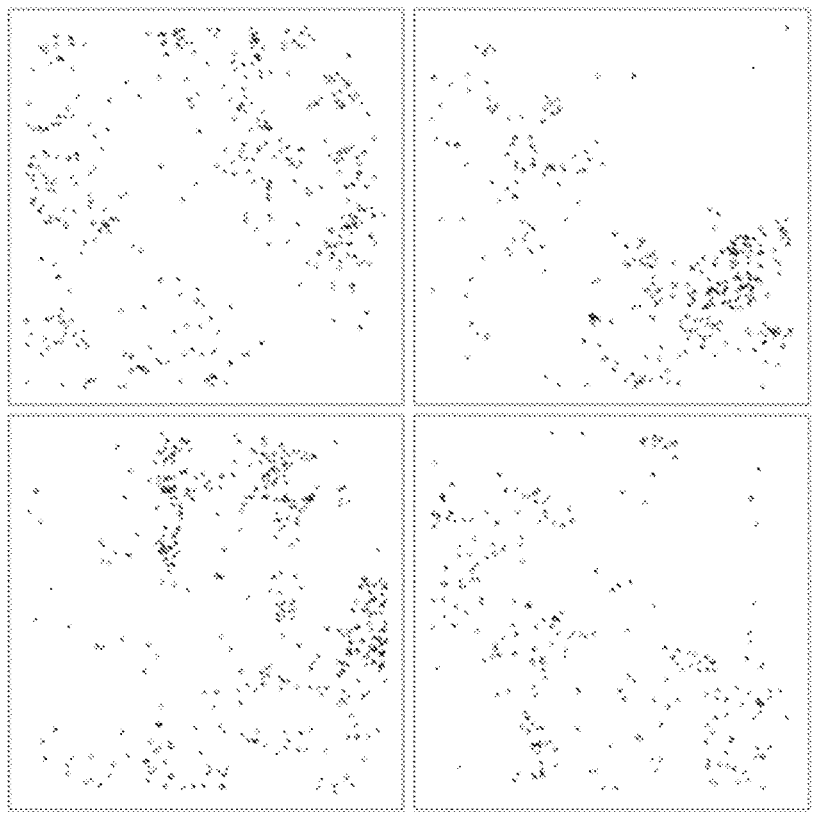
Figure 13C:
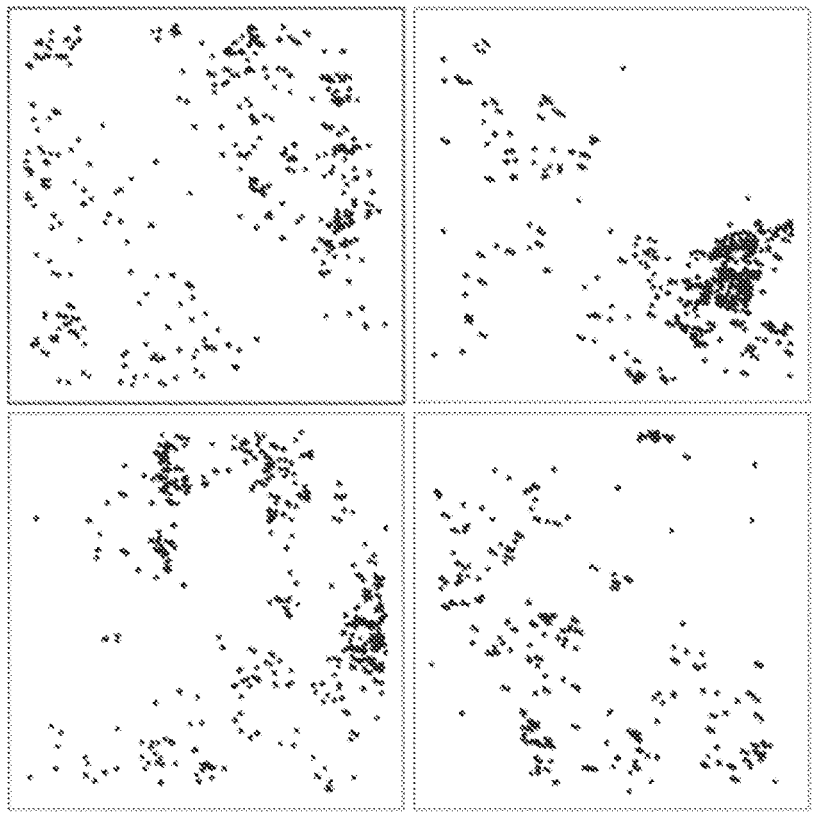

Results: As explained above, the first aim of the analysis was to confirm that we were able to transfer the molecules, which carried a fluorophore, to the surface that we then used for detection. FIG. 11 clearly shows that the reporter molecules were correctly transferred to the surface, and at the expected locations. The second aim was to demonstrate that we were able to detect these molecules using a cyclic detection system. FIG. 12 shows that the areas where the reporter molecules density is higher are also the ones that produce higher signal intensity from the detection system in the detection cycles (cycles 2, 4, 6, and 8). In addition, FIG. 13 shows that both detection systems 1 and 2 are capable of hybridizing to their target sites (FIG. 13A-B), and that the overlap between the two (FIG. 13C) specifically localizes where the majority of the reporter molecules can be found (FIG. 13D. Collectively, this demonstrate the i) a sufficient number of molecules has been transferred from the tissue to the surface and that ii) the approach is capable of detecting the presence of these molecules with high confidence.

Example 6

Oligonucleotide Design

The following oligonucleotides may be used in some embodiments of the method:

```
Left target oligonucleotide (conjugate arm):
                                            (SEQ ID NO: 1)
/5AzideN/TTTUUUCGTUTACGACCUCUAAGGCCACGAUAGCGT Right target oligonucleotide (conjugate arm):
                                            (SEQ ID NO: 2)
/5Phos/ATGCUAACCGC*A*G*A*C*CACTAGGCGAATACGTTTTTT/
3AzideN/

Splint:
                                            (SEQ ID NO: 3)
/5Phos/CGGTTAGCATACGCTATCGT Left reporter oligonucleotide:
                                            (SEQ ID NO: 4)
/5Phos/GGCCTTAGAGGTCGTAAACGTTTGAAGCAATCCGTGGGCGGG
CGCAAACGTTTGTCGACA/3Bio/

Right reporter oligonucleotide:
                                            (SEQ ID NO: 5)
A*A*T*GTTTCGCGTGCATCCGGCTCCACCGGATTTGCAGCTTCGTATT
CGCCTAGTGGTCTG
```

The modifications of this oligonucleotides are described below.
/5AzideN/: Azide modification attached via NHS ester
/5Phos/: Phosphorylation
U Deoxyuridine

* Phosphorothioate bond
/3AzideN/ Azide modification attached via NHS ester
/3Bio/ Biotin In this embodiment, the left and right target oligonucleotides are joined to antibodies via their azide groups, and the antibodies are bound to the sample. After binding, the sample is incubated with a ligase and the splint oligonucleotide. Target oligonucleotides that are proximal become ligated to each other in a ligation that is mediated by the splint oligonucleotide. In the next step, the left and right reporter oligonucleotides are hybridized to the sample with the splint still hybridized to the ligation product. The left and right reporter oligonucleotides hybridize to sites in the ligation product that are adjacent to the splint and the reporter oligonucleotides become ligated to the splint to produce a reporter molecule. After the reporter molecule has been produced, the sample is treated with UDG or USER to cleave the ligation products at the uracils or remove the uracils. This lowers the Tm of the interaction between the reporter molecule and the underlying ligation product, which allows the reporter molecule to be readily released. This embodiment is illustrated in FIG. 2B.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An in vitro method for analyzing a sample, comprising:
   (a) contacting an oligonucleotide or a conjugate comprising the same with a planar biological sample that is a tissue section under conditions by which the oligonucleotide or conjugate specifically binds to sites in or on the tissue section;
   (b) performing one or more steps to release and/or extend the oligonucleotide in situ, to produce a reporter probe;
   (c) transferring all or a part of the reporter probe from the tissue section to a planar support that does not comprise oligonucleotides, wherein the transferring is done by placing the tissue section on the support and transferring the reporter probe onto the surface of the support by diffusion such that the spatial relationship of the reporter probe in the tissue section is preserved, wherein the planar support is glass; and
   (d) detecting the reporter probe on the glass support by microscopy,
   wherein step (d) comprises hybridizing one or more labeled oligonucleotides, directly or indirectly, to the reporter probe and then detecting the binding pattern of the labeled oligonucleotides by microscopy, and
   wherein the method is free of any nucleic acid amplification on the planar support.

2. The method of claim 1, wherein:
   step (a) comprises hybridizing oligonucleotides with the tissue section under conditions by which the oligonucleotides hybridize to endogenous RNA or DNA in the tissue section; and
   step (b) comprises joining together any oligonucleotides that are hybridized to adjacent sites in the RNA or DNA via a ligation or gap-fill/ligation.

3. The method of claim 1, wherein the tissue section comprises ligation products from a proximity ligation assay; and
   step (a) comprises hybridizing oligonucleotides with the tissue section under conditions by which the oligonucleotides hybridize to the ligation products; and
   step (b) comprises joining together any oligonucleotides that are hybridized to adjacent sites in the ligation products via a ligation or gap-fill/ligation reaction.

4. The method of claim 1, wherein the oligonucleotides that are hybridized to the reporter probe in step (d) are exonuclease-sensitive but the reporter probe is exonuclease-resistant, optionally wherein the method further comprises treating the tissue section with an exonuclease between steps (b) and (c).

5. The method of claim 1, wherein;
   step (a) comprises contacting the tissue section with antibody-oligonucleotide conjugates under conditions by which the antibodies bind to sites in or on the tissue section; and
   step (b) comprises releasing the oligonucleotides or an extension product thereof from the conjugates antibodies to produce the reporter probe.

6. The method of claim 1, wherein the reporter probe is produced via a ligation or gap-fill reaction, or wherein the reporter probe is produced via primer extension reaction.

7. The method of claim 1, wherein the releasing is done by contacting the tissue section with the support after step (a) and then heating the tissue section.

8. The method of claim 1, wherein sets of probes are hybridized and washed away in repeated cycles to decode individual reporter molecules.

9. The method of claim 1, wherein the tissue section comprises mammalian cells.

10. An in vitro method for analyzing a planar biological sample, comprising:
    (a) performing a proximity assay on one or more pairs of binding agent-oligonucleotide conjugates that are bound to the sample, in situ, to produce proximity assay reaction products;
    (b) transferring the nucleic acid reaction products onto a planar support that does not comprise oligonucleotides, wherein the transferring is done by placing the sample on the support and transferring the proximity assay reaction products onto the surface of the support by diffusion such that the spatial relationship of the proximity assay reaction products in the sample is preserved, wherein the planar support is glass; and
    (c) detecting the proximity assay reaction products on the glass support by:
        (i) labeling the proximity assay reaction products on the glass support; and
        (ii) imaging the glass support to produce an image of the sites to which the proximity assay reaction products are bound to the support,
    wherein the method is free of any nucleic acid amplification on the planar support.

11. The method of claim 10, wherein the proximity assay comprises any combination of a ligation, a primer extension, and a gap-fill/ligation reaction involving the oligonucleotides of the binding agent-oligonucleotide conjugates.

12. The method of claim 10, wherein step (c) comprises: hybridizing one or more labeled oligonucleotides, directly or indirectly, to the nucleic acid reaction products.

13. The method of claim 12, wherein in step (c) the proximity assay reaction products are detected by hybridization to a defined nucleic acid structure composed of a predetermined number of oligonucleotides and a predetermined number of labeled oligonucleotides.

14. The method of claim 13, wherein the structure is nucleated by at least two hybridization events to the proximity assay reaction products.

15. The method of claim 14, wherein the at least two hybridization events comprise a first hybridization to a first sequence in a proximity assay reaction product and a second hybridization to a second sequence in the proximity assay reaction product.

16. The method of claim 10, wherein the method comprises comparing the image produced in step (c) with an image of the sample, optionally wherein the image of the sample is produced via staining the sample with a microscopy stain.

17. The method of claim 10, further comprising removing the sample from the support between steps (b) and (c).

18. The method of claim 10, wherein the biological sample is a tissue section.

19. The method of claim 18, wherein the tissue section is a formalin-fixed paraffin embedded (FFPE) tissue section.

20. The method of claim 10, wherein the binding agents of step (a) are oligonucleotide probes, antibodies, or aptamers.

21. The method of claim 1, wherein the diffusion is aided by electrostatic, electric or magnetic forces.

22. The method of claim 1, wherein the planar support is modified and/or functionalized glass.

* * * * *